(12) United States Patent
Seeberger et al.

(10) Patent No.: US 10,588,962 B2
(45) Date of Patent: Mar. 17, 2020

(54) CARBOHYDRATE-GLYCOLIPID CONJUGATE VACCINES

(71) Applicants: Max-Planck-Gesellschaft zur Förderung der Wissenschaften e.V., Munich (DE); UNIVERSITÄTSSPITAL BASEL, Basel (CH)

(72) Inventors: Peter H. Seeberger, Berlin (DE); Pierre Stallforth, Cambridge, MA (US); Gennaro De Libero, Bottmingen (CH); Marco Cavallari, Münchenstein (CH)

(73) Assignees: Max-Planck-Gesellschaft zur Förderung der Wissenschaften e.V., Munich (DE); UNIVERSITÄTSSPITAL BASEL, Basel (CH)

( * ) Notice: Subject to any disclaimer, the term of this patent is extended or adjusted under 35 U.S.C. 154(b) by 26 days.

(21) Appl. No.: 14/385,948

(22) PCT Filed: Mar. 19, 2013

(86) PCT No.: PCT/EP2013/055719
§ 371 (c)(1),
(2) Date: Sep. 17, 2014

(87) PCT Pub. No.: WO2013/139803
PCT Pub. Date: Sep. 26, 2013

(65) Prior Publication Data
US 2015/0238597 A1    Aug. 27, 2015

(30) Foreign Application Priority Data

Mar. 19, 2012  (EP) .................. PCT/EP2012/054848
May 26, 2012  (EP) .................. PCT/EP2012/002277

(51) Int. Cl.
| | | |
|---|---|---|
| A61K 39/39 | (2006.01) | |
| A61K 39/09 | (2006.01) | |
| C07K 16/12 | (2006.01) | |
| A61K 39/00 | (2006.01) | |

(52) U.S. Cl.
CPC ............ *A61K 39/39* (2013.01); *A61K 39/092* (2013.01); *C07K 16/1275* (2013.01); *A61K 2039/55572* (2013.01); *A61K 2039/6087* (2013.01); *A61K 2039/627* (2013.01); *Y02A 50/407* (2018.01); *Y02A 50/41* (2018.01); *Y02A 50/412* (2018.01); *Y02A 50/423* (2018.01); *Y02A 50/466* (2018.01); *Y02A 50/47* (2018.01); *Y02A 50/489* (2018.01); *Y02A 50/49* (2018.01); *Y02A 50/492* (2018.01)

(58) Field of Classification Search
CPC .. C07K 16/1275; A61K 39/39; A61K 39/092; A61K 2039/627; A61K 2039/6087; A61K 2035/55572

USPC ...................... 424/194.1; 536/17.9
See application file for complete search history.

(56) References Cited

U.S. PATENT DOCUMENTS

| | | | | |
|---|---|---|---|---|
| 8,273,357 B2 * | 9/2012 | Hacohen | .......... | A61K 47/48192 424/193.1 |
| 2012/0021050 A1 | 1/2012 | Zhou | | |

FOREIGN PATENT DOCUMENTS

| | | | |
|---|---|---|---|
| JP | 2005-500336 A | 1/2005 | |
| JP | 2008-511634 A | 4/2008 | |
| JP | 2011-510910 A | 4/2011 | |
| WO | 02/056893 A1 | 7/2002 | |
| WO | 03/009812 A2 | 2/2003 | |
| WO | WO 03/009812 A2 * | 2/2003 | |
| WO | 2006/026389 A2 | 3/2006 | |
| WO | 2006/027685 A2 | 3/2006 | |
| WO | WO 2006/027685 A2 * | 3/2006 | ......... A61K 31/7032 |
| WO | 2007/051004 A2 | 5/2007 | |
| WO | WO 2007/051004 A2 * | 5/2007 | ............ A61K 39/39 |
| WO | 2008/128062 A1 | 10/2008 | |
| WO | 2008/133801 A1 | 11/2008 | |
| WO | 2009/060305 A2 | 5/2009 | |
| WO | 2010/083728 A1 | 9/2010 | |

OTHER PUBLICATIONS

Kinjo et al, Chemistry & Biology, 2008, 15, Jul. 21, 654-664.*
Devi et al, Infection and Immunity, 1997, 65(3), 1045-52.*
Leadbetter et al, PNAS, 2008, 105(24), 8339-8344.*
Cadedddu et al, Organic & Biomolecular Chemistry, 2011, 9, 3080-3104.*
Korean Office Action dated Dec. 10, 2015, in connection with corresponding KR Application No. 10-2014-7029250 (11 pgs., including English translation).
Q. Wang, et al., "Carbohydrate-Monophosphoryl Lipid A Conjugates are Fully Synthetic Self-Adjuvanting Cancer Vaccines Eliciting Robust Immune Responses in the Mouse", in ACS Chemical Biology, vol. 7, 2012, pp. 235-240 (6 pgs.).

(Continued)

*Primary Examiner* — Ganapathy Krishnan
(74) *Attorney, Agent, or Firm* — Maier & Maier, PLLC

(57) ABSTRACT

The present invention relates to the field of synthesizing and biologically evaluating of a novel class of carbohydrate-based vaccines. The new vaccines consist of a multi-modular structure which allows applying the vaccine to a whole variety of pathogenes. This method allows preparing vaccines against all pathogens expressing immunogenic carbohydrate antigens. As conjugation of antigenic carbohydrates to proteins is not required the conjugate vaccine is particularly heat stable. No refrigeration is required, a major drawback of protein-based vaccines.

12 Claims, 9 Drawing Sheets
Specification includes a Sequence Listing.

(56) References Cited

OTHER PUBLICATIONS

International Search Report dated May 22, 2013 from corresponding International Patent Application No. PCT/EP2013/055719; 4 pgs.
Masakazu Fujio, et al., "Structure-Based Discovery of Glycolipids for CD1d-Mediated NKT Cell Activation: Tuning the Adjuvant versus Immunosuppression Activity", in J. Am. Chem. Soc., vol. 128, 2006, pp. 9022-9023 (2 pgs.).
Kazuhiro Motoki, et al., "Immunostimulatory and Antitumor Activities of Monoglycosylceramides Having Various Sugar Moieties", in Biol. Pharm. Bull, vol. 18, No. 11, 1995, pp. 1487-1491 (5 pgs.).
Natacha Veerapen, et al., "Synthesis and biological activity of α-galactosyl ceramide KRN7000 and galactosyl (α1→2J) galactosyl ceramide", in Bioorganic & Medicinal Chemistry Letters, vol. 19, No. 15, Aug. 1, 2009, pp. 4288-4291 (12 pgs.).
Yuki Kinjo, et al., "Invariant natural killer T cells recognize glycolipids from pathogenic Gram-positive bacteria", in Nature Immunology, Advance Online Publication, Sep. 4, 2011, 10 pgs.
Shin-ichiro Fujii, et al., Activation of Natural Killer T Cells by α-Galactosylceramide Rapidly Induces the Full Maturation of Dendritic Cells In Vivo and Thereby Acts as an Adjuvant for Combined CD4 and CD8 T Cell Immuinity to a Coadministered Protein, in The Journal of Experimental Medicine, vol. 198, No. 2, Jul. 21, 2003, pp. 267-279 (13 pgs.).
Aline Banchet-Cadeddu, et al., "The stimulating adventure of KRN 7000", in Organic & Biomolecular Chemistry, 2011, 25 pgs.
Shenglou Deng, et al., "Impact of Sugar Stereochemistry on Natural Killer T Cell Stimulation by Bacterial Glycolipids", in Org. Biommol. Chem., vol. 9, No. 22, Oct. 26, 2011, pp. 7659-7662 (10 pgs.).
Dong Jae Back, et al., "The 3-Deoxy Analogue of α-GalCer: Disclosing the Role of the 4-Hydroxyl Group for CD1d-Mediated NKT Cell Activation", in ACS Medicinal Chemistry Letters, vol. 2, 2011, pp. 544-548 (5 pgs).
Rachel M. Ndonye, et al., "Synthesis and Evaluation of Sphinganine Analogues of KRN7000 and OCH", in J. Org. Chem., vol. 70, 2005, pp. 10260-10270 (11 pgs.).
Sung-Youl Ko, et al., "α-Galactosylceramide Can Act As a Nasal Vaccine Adjuvant Inducing Protective Immune Responses against Viral Infection and Tumor", in The Journal of Immunology, vol. 175, 2005, pp. 3309-3317 (10 pgs.).
Russian Office Action dated Jan. 30, 2017, in connection with corresponding RU Application No. 2014142043 (12 pgs., including English translation).

\* cited by examiner

Figure 6

| Hybridoma | Heavy chain | CDR1 | CDR2 | CDR3 | Mutations (aa/nuc)* |
|---|---|---|---|---|---|
| 6C2 | γ1 | GYSITSGYS | I--HY---SGYT | ARSANYGPM------DYWGQG | 4/6 |
| 2F4 | γ1 | GFSLTS-YG | I---W-SDGST | ARHSKLGQF------AYWGQG | 0/1 |
| 1B4 | γ1 | GYSITSGYS | I--HY---SGYT | ARSANYGPM------DYWGQG | 4/6 |
| 12F10 | γ1 | GYSITSGYS | I--HY---SGST | ARSANYGPM------DYWGQG | 2/5 |
| 2B5 | γ2a | GFSLTS-YG | I---W-SGGST | VRNGVYRDF------AYWGQG | 0/0 |
| 26D2 | γ3 | GFSLTS-YG | I---W-GDGST | AKIYYYGRN--YAMDYWGQG | 1/2 |
| 26H11 | μ | GYTFTS-YY | I-IYPGNVNT | ARGGNYYYY---AMDYWGQG | 0/0 |
| 10B4 | μ | GYSFTG-YN | IDPY--YGGT | ARSTGTAWF------AYWGQG | 0/0 |
| 5H3 | μ | GFTFSS-YG | I-S-SGGSYT | ARLYD-GYY-VAWFAYWGQG | 0/0 |
| 14D3 | μ | GFSLTS-YG | I---W-SGGST | ARNSGTGWY------FDVWGAG | 0/0 |
| 18E4 | μ | GFSLTS-YG | I---W-SGGST | ARNGNRAWF------AYWGQG | 0/0 |
| 16D9 | μ | GYTFT-DYA | ISTY--YGNT | AR------GDW------EDYWGQG | 4/9 |
| 3E10 | μ | GFSLTS-YG | I---W-SGGST | ARDGYPAWF------AYWGQG | 0/0 |
| 26F3 | μ | GYTFTS-YW | I---NPSTGYT | ARGRN--HY------FDYWGQG | 0/1 |
| 25B7 | μ | GFSLTD-YG | I---W-GGGST | AKQGNWADY--YAMDYWGQG | 0/0 |
| 25A8 | μ | GYTFSR-YW | I--LPGSGTT | ARLLR---Y------FDYWGQG | 3/5 |
| 21B6 | μ | GYSFTG-YN | IDPY--YGGT | ARS-NWTYY--YAMDYWGQG | 0/0 |
| 18G6 | μ | GYSFTG-YN | IDPY--YGGT | AR------GY---AMDYWGQG | 0/0 |
| 18G6 | μ | GYSITSDYA | I-SY--SGST | ARSL-YGNYGDYAMDYWGQG | 0/0 |

CARBOHYDRATE-GLYCOLIPID CONJUGATE VACCINES

The present invention relates to the field of synthesizing and biologically evaluating of a novel class of carbohydrate-based vaccines. The new vaccines consist of a multi-modular structure which allows applying the vaccine to a whole variety of pathogenes. This method allows preparing vaccines against all pathogens expressing immunogenic carbohydrate antigens. As conjugation of antigenic carbohydrates to proteins is not required the conjugate vaccine is particularly heat stable. No refrigeration is required, a major drawback of protein-based vaccines.

BACKGROUND OF THE INVENTION

High prevalence of many infectious diseases, such as invasive pneumococcal disease (IPD) and increasing antibiotic resistance of the related pathogens requires urgent development of protective vaccines. Especially as existing vaccines exhibit major drawbacks such as variable immunogenicity and the lack of development of immunological memory.

Vaccines have traditionally consisted of live attenuated pathogens, whole inactivated organisms or inactivated toxins. In many cases, these approaches have been successful at inducing immune protection based on antibody mediated responses. However, certain pathogens, e.g., HIV, HCV, TB, and malaria, require the induction of cell-mediated immunity (CMI). Non-live vaccines have generally proven ineffective in producing CMI. In addition, although live vaccines may induce CMI, some live attenuated vaccines may cause disease in immunosuppressed subjects.

In contrast to older vaccines which were typically based on live attenuated or non-replicating inactivated pathogens, modern vaccines are composed of synthetic, recombinant, or highly purified subunit antigens. Subunit-vaccines are designed to include only the antigens required for protective immunization and are believed to be safer than whole inactivated or live-attenuated vaccines. However, the purity of the subunit antigens and the absence of the self-adjuvanting immunomodulatory components associated with attenuated or killed vaccines often result in weaker immunogenicity.

The immunogenicity of a relatively weak antigen can be enhanced by the simultaneous or more generally conjoined administration of the antigen with an "adjuvant", usually a substance that is not immunogenic when administered alone, but will evoke, increase and/or prolong an immune response to an antigen. In the absence of adjuvant, reduced or no immune response may occur, or worse the host may become tolerized to the antigen.

Adjuvants can be found in a group of structurally heterogeneous compounds (Gupta et al., 1993, Vaccine, 11: 293-306). Classically recognized examples of adjuvants include oil emulsions (e.g., Freund's adjuvant), saponins, aluminium or calcium salts (e.g., alum), non-ionic block polymer surfactants, lipopolysaccharides (LPS), mycobacteria, tetanus toxoid, and many others. Theoretically, each molecule or substance that is able to favor or amplify a particular situation in the cascade of immunological events, ultimately leading to a more pronounced immunological response can be defined as an adjuvant.

A galactosylceramide (α-GalCer) is a glycolipid, more specifically a glycosylceramide, originally isolated from Okinawan marine sponges (Natori et al., Tetrahedron, 50: 2771-2784, 1994), or its synthetic analog KRN7000 [(2S, 3S,4R)-1-O-(α-D-galactopyranosyl)-2-(N-hexacosanoylamino)-1,3,4-octadecanetriol], which can be obtained from Pharmaceutical Research Laboratories, Kirin Brewery (Gumna, Japan) or synthesized as described previously (see, e.g., Kobayashi et al., 1995, Oncol. Res., 7:529-534; Kawano et al., 1997, Science, 278: 1626-9; Burdin et al., 1998, J. Immunol., 161:3271; Kitamura et al., 1999, J. Exp. Med., 189:1121; U.S. Pat. No. 5,936,076).

It was shown that α-GalCer can stimulate natural killer (NK) activity and cytokine production by natural killer T (NKT) cells and exhibits potent antitumor activity in vivo (Kawano et al., 1998, Proc. Natl Acad. Sci. USA, 95:5690). After intake by antigen presenting cell (APC), which is represented by dendritic cell (DC) and the like, α-galactosylceramide is presented on the cellular membrane by a CD1d protein similar to major histocompatible complex (MHC) class I molecule. NKT cells are activated by recognition using TCR (T cell receptor) of the thus-presented complex of CD1d protein and α-galactosylceramide, which triggers various immune reactions. Invariant Natural Killer T cells have been also shown to induce B cell activation, enhancing B cell proliferation and antibody production (Galli et al, *Vaccine*, 2003, 21: 2148-S2154; Galli et al, *J Exp. Med*, 2003, 197: 1051-1057).

These studies open the possibility that α-GalCer may play an equally important role in bridging not only innate immunity mediated by NKT cells, but also adaptive immunity mediated by B cells, T helper (Th) cells and T cytotoxic (Tc) cells. Recently, α-GalCer has been shown to act as an adjuvant for a variety of co-administered protein antigens and saccharide antigens (WO03/009812).

The development so far exhibits the simultaneous use of the vaccine and an adjuvant that produces the desired immunogenicity. A major drawback of protein-based vaccines, where a conjugation of antigenic carbohydrates to proteins is required, is that the vaccine is particularly heat unstable and a refrigeration of the vaccine is required. Moreover the use of at least two components to achieve a sufficient vaccination is also a significant drawback, since the procedure of administration is rather complex, e.g. the point in time where the adjuvant is administered is essential to achieve the desired immunogenicity (WO003009812).

DESCRIPTION OF THE INVENTION

To fulfill these requirements and to overcome the disadvantages of current vaccines the invention exhibits a new type of conjugate vaccine, wherein the carbohydrate antigen is covalently bound to the glycolipid adjuvant.

Protection against an infectious disease is provided by neutralization of virulence factors or opsonizing antibodies. The antibodies (Abs.) have to be directed against the carbohydrate antigen of the pathogen, e.g from capsules composed of polysaccharides or viral glycoproteins. Therefore, an ideal efficient vaccine has to induce high affinity and complement-fixing anti-carbohydrate antibodies. This is actually fulfilled by the conjugates of the present invention.

The novel carbohydrate-glycolipid conjugate derivatives according to the present invention are represented by the following general formula (I). It was surprisingly found that extraordinary potent and stable vaccine can be derived when a polysaccharide antigen is bound via a linker and a carbohydrate moiety to a ceramide moiety. Thus the present invention relates to compounds of the general formula (I)

$$A[L-CH-CA]_p \qquad (I)$$

wherein

A represents a carbohydrate antigen of 1 to 10.000 carbohydrate monomers, wherein the carbohydrate monomers of the carbohydrate antigen are optionally modified to carry amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties, p is the number of residues -L-CH—CA which are bound to the carbohydrate antigen A, and p is an integer defined as follows:
p is 1 or 2 if u is 1
p is 1, 2, 3 or 4 if u is 2
p is 1, 2, 3, 4, 5 or 6 if u is 3
p is 1, 2, 3, 4, 5, 6, 7 or 8 if u is 4
$1 \leq p \leq 10$ if $5 \leq u \leq 10$
$2 \leq p \leq 50$ if $11 \leq u \leq 100$
$20 \leq p \leq 200$ if $101 \leq u \leq 1000$
$50 \leq p \leq 400$ if $1001 \leq u \leq 10000$ u is the number of carbohydrate monomers of the carbohydrate antigen A L represents $-L^1-L^2-$, $-L^2-$, $-L^2-L^3-$ or $-L^1-L^2-L^3-$;

$L^1$ represents one of the following residues:

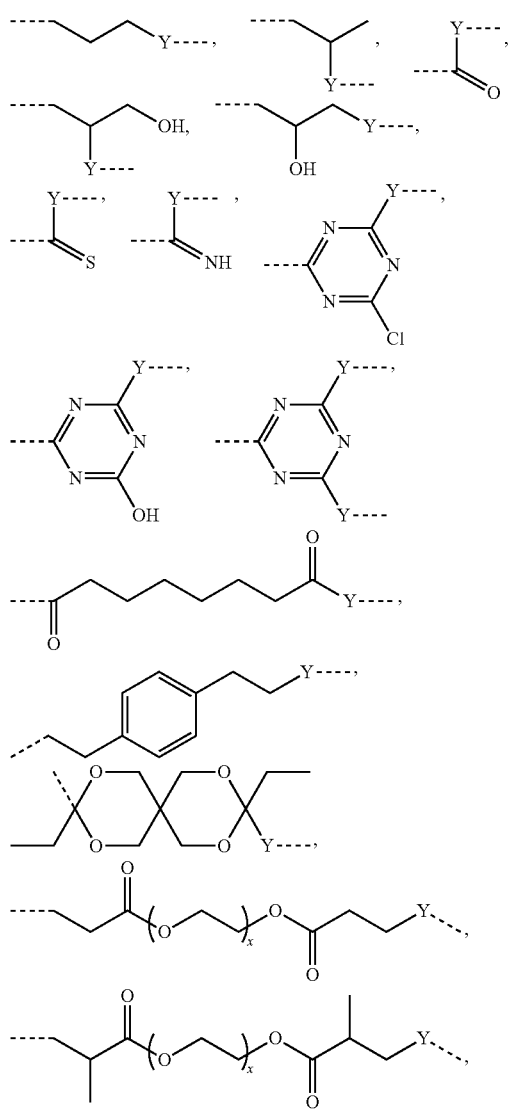

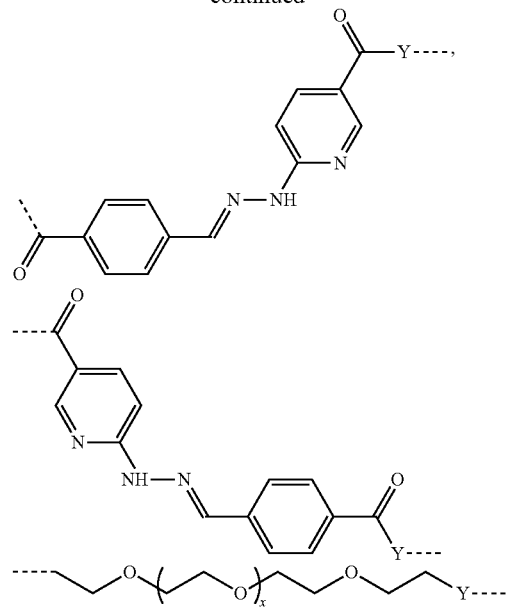

wherein x is in integer from 1 to 60;

Y represents a bond, —NH—, —O—, —S—;

$L^2$ represents —$CH_2$—, —$C_2H_4$—, —$C_3H_6$—, —$C_4H_8$—, —$C_5H_{10}$—, —$C_6H_{12}$—, —$C_7H_{14}$—, —$C_8H_{16}$—, —$C_9H_{18}$—, —$C_{10}H_{20}$—, —$CH(CH_3)$—, —$C[(CH_3)_2]$—, —$CH_2$—$CH(CH_3)$—, —$CH(CH_3)$—$CH_2$—, —$CH(CH_3)$—$C_2H_4$—, —$CH_2$—$CH(CH_3)$—$CH_2$—, —$C_2H_4$—$CH(CH_3)$—, —$CH_2$—$C[(CH_3)_2]$—, —$C[(CH_3)_2]$—$CH_2$—, —$CH(CH_3)$—$CH(CH_3)$—, —$C[(C_2H_5)(CH_3)]$—, —$CH(C_3H_7)$—, —$(CH_2-CH_2-O)_n$—$CH_2$—$CH_2$—, —CO—$CH_2$—, —CO—$C_2H_4$—, —CO—$C_3H_6$—, —CO—$C_4H_8$—, —CO—$C_5H_{10}$—, —CO—$C_6H_{12}$—, —CO—$C_7H_{14}$—, —CO—$C_8H_{16}$—, —CO—$C_9H_{18}$—, —CO—$C_{10}H_{20}$—, —CO—$CH(CH_3)$—, —CO—$C[(CH_3)_2]$—, —CO—$CH_2$—$CH(CH_3)$—, —CO—$CH(CH_3)$—$CH_2$—, —CO—$CH(CH_3)$—$C_2H_4$—, —CO—$CH_2$—$CH(CH_3)$—$CH_2$—, —CO—$C_2H_4$—$CH(CH_3)$—, —CO—$CH_2$—$C[(CH_3)_2]$—, —CO—$C[(CH_3)_2]$—$CH_2$—, —CO—$CH(CH_3)$—$CH(CH_3)$—, —CO—$C[(C_2H_5)(CH_3)]$—, —CO—$CH(C_3H_7)$—, —CO—$(CH_2-CH_2-O)_n$—$CH_2$—$CH_2$—;

n represents an integer from 1 to 60;

$L^3$ represents —CO—, —O—CO—, —NH—CO—, —NH(C=NH)—, —$SO_2$—, —O—$SO_2$—;

CH represents a monosaccharide, a disaccharide or a trisaccharide;

CA represents or

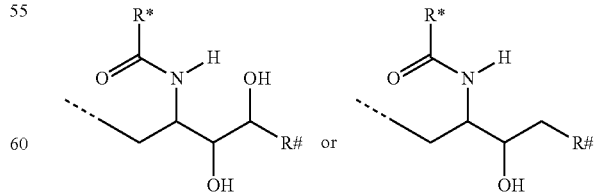

R* and R# represent independently of each other a linear or branched or cyclic, substituted or unsubstituted, saturated or unsaturated carbon residue consisting of 1 to 30 carbon atoms;

and enantiomers, stereoisomeric forms, mixtures of enantiomers, diastereomers, mixtures of diastereomers, prodrugs, hydrates, solvates, tautomers, and racemates of the above mentioned compounds and pharmaceutically acceptable salts thereof.

Antigen

A represents a carbohydrate antigen consisting of 1 to 10.000 carbohydrate monomers.

The term "antigen" as used herein refers to a substance which cause after introduction into the organism of humans and animals, a specific immune response. This manifests itself either in the formation of antibodies (humoral response) and the development of cell-mediated immunity (cellular immune response) or a specific immune tolerance. Depending on whether the formation of the immune response involving T-lymphocytes (T cells) is required, it is called thymus-dependent or -independent antigen. A prerequisite for an immune response (for the immunogenicity of the antigen) is that the antigen is recognized as foreign by the organism, that it has a molecular weight of at least 1000 and that it belongs to the class of proteins or polysaccharides, rare deoxyribonucleic acids or lipids. More complex structures such as bacteria, viruses, or erythrocytes (particulate antigens) are generally more effective antigens. At the molecular level, an antigen is characterized by its ability to be "bound" at the antigen-binding site of an antibody.

Foreign substances that do not stimulate an immune response by themselves, but by the chemical binding to immunogenic macromolecules, are called haptens. For the efficacy of immunogenic antigens the route of administration (single or multiple dose, dose intradermally or intravenously, with or without adjuvant) is determining. Repeated attacks by the same antigens accelerate the immune response and may result in the worst case of a specific hypersensitivity (allergy, where the antigens are often called allergens). In the presence of large amounts of antigen or chronic persistent amounts of antigen the formation of soluble immune complexes may occur, which can cause anaphylaxis.

An immunogen is a specific type of antigen. An immunogen is a substance that is able to provoke an adaptive immune response if injected on its own. An immunogen is able to induce an immune response, whereas an antigen is able to combine with the products of an immune response once they are made. Immunogenicity is the ability to induce a humoral and/or cell-mediated immune response The term "antigen" may shortly be described as a substance, belonging to the class of proteins or polysaccharides, generally comprising parts (coats, capsules, cell walls, flagella, fimbrae, and toxins) of bacteria, viruses, and other microorganisms, and also rare deoxyribonucleic acids or lipids, smaller molecules or ions (haptens), which are recognized as foreign by the organism of humans and animals and which may cause after introduction into the organism of humans and animals, a specific immune response, which comprises a humoral and/or or a cellular immune response, which leads to the formation of antibodies (humoral response) and/or the development of cell-mediated immunity (cellular response), wherein the mentioned antibodies may lead to a specific binding of the antigen.

Specifically, the term "antigen" can be described as a substance, which is recognized as foreign by the organism of humans and animals and which may cause after introduction into the organism of humans and animals, a specific immune response, which comprises a humoral and/or or a cellular immune response.

Preferably A represents an isolated, a semi-synthetic or a synthetic carbohydrate antigen. The isolated carbohydrate antigen consists of 1 to 10,000 carbohydrate monomers, preferably of 10 to 5,000 carbohydrate monomers, and more preferably of 20 to 3,000. The semi-synthetic carbohydrate antigen preferably consists of 1 to 1.000 carbohydrate monomers, more preferably of 5 to 900 and still more preferably of 10 to 800 carbohydrate monomers and the synthetic carbohydrate antigen preferably consists of 1 to 1.000 carbohydrate monomers, more preferably of 5 to 900 and still more preferably of 10 to 800 carbohydrate monomers.

The antigens and especially the isolated antigens are normally mixtures of antigens having a certain range of carbohydrate monomers so that the term "antigen consisting of 500 carbohydrate monomers" refers to a mixture of antigens having in average the number of 500 carbohydrate monomers. Such a mixture might contain 10% of the antigens with 450 to 470 carbohydrate monomers, 10% of the antigens with 530 to 550 carbohydrate monomers, 20% of the antigens with 471 to 490 carbohydrate monomers, 20% of the antigens with 510 to 529 carbohydrate monomers and 40% of the antigens with a number of 491 to 509 carbohydrate monomers.

Preferably the carbohydrate monomers belong to heptoses, hexoses, pentoses, tetroses or sialic acids, wherein the carbohydrate monomers are connected to each other via α/β glycosidic bonds which belong to the group consisting of 1,2; 1,3; 1,4; 1,5; 1,6; 2,2; 2,3; 2,4; 2,5; or 2,6 glycosidic bonds. Also, the carbohydrate monomers can be more specifically derivatives of peptidoglycanes such as N-acetyl-muramic acid, N-acetyl-D-glocosamine or N-acetyl talosaminuronic acid.

Some of the hydroxyl groups (—OH) of the carbohydrate monomers of the antigen A can independently of each other optionally be substituted with the following substituents —$CH_3$, —$C_2H_5$, —$SO_3H$, —$SO_3^-$, —$CH_2$—COOH, —$CH_2$—$COO^-$, —$C_2H_4$—COOH, —$C_2H_4$—$COO^-$ or some of the hydroxyl groups (—OH) of the carbohydrate monomers can be replaced by the following moieties:

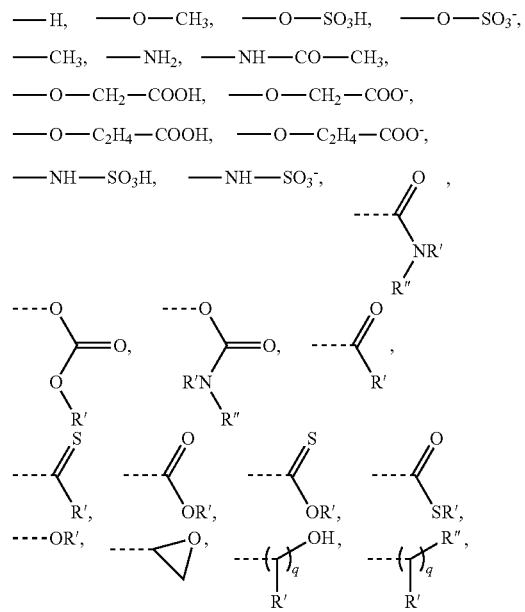

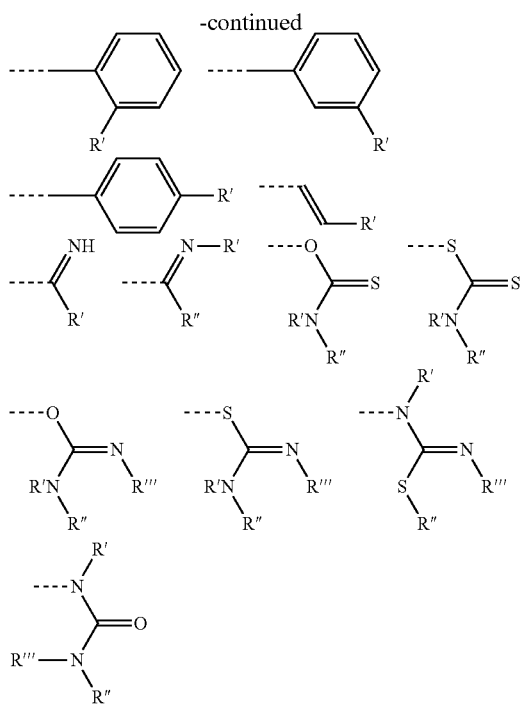

wherein
q is an integer from 1 to 4, and
R', R" and R"' independently of each other represent one of following residues: —H, —CH$_3$, —C$_2$H$_5$, —C$_3$H$_7$, -cyclo-C$_3$H$_5$, —CH(CH$_3$)$_2$, —C(CH$_3$)$_3$, —C$_4$H$_9$, -Ph, —CH$_2$-Ph, —CH$_2$—OCH$_3$, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_6$—OPh, —CH$_2$—OCH$_2$-Ph, —C$_2$H$_4$—OCH$_2$-Ph, —C$_3$H$_6$—OCH$_2$-Ph.

These groups are naturally occurring substituents which can be present in the carbohydrate antigens.

The carbohydrate monomers of the carbohydrate antigen can therefore be optionally modified or can be modified to carry amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties.

The term "hydroxylalkyl" refers preferably to linear or branched C$_1$-C$_4$ hydroxyalkyl residues which consist in total of 1 to 4 carbon atoms including the carbon atoms of the branches wherein one of the hydrogen atoms is substituted by a hydroxyl group such as —CH$_2$OH, —C$_2$H$_4$OH, —CHOHCH$_3$, —CH$_2$CH$_2$CH$_2$OH, —CH$_2$CHOHCH$_3$, —CHOHCH$_2$CH$_3$, -cyclo-C$_3$H$_4$OH, —COH(CH$_3$)$_2$, —CH(CH$_3$)CH$_2$OH, —CH$_2$CH$_2$CH$_2$CH$_2$OH, —CH$_2$CH$_2$CHOHCH$_3$, —CH$_2$CHOHCH$_2$CH$_3$, —CHOHCH$_2$CH$_2$CH$_3$, —C(CH$_3$)$_2$CH$_2$OH, —CHOH—CH(CH$_3$)$_2$, —CH(CH$_3$)—CHOHCH$_3$, —CCH$_3$OH—C$_2$H$_5$, —CH$_2$—C(CH$_3$)$_2$OH.

As used herein, the term alkenyl refers preferably to "linear or branched C$_2$-C$_8$-alkenyl" such as —CH=CH$_2$, —CH$_2$—CH=CH$_2$, —C(CH$_3$)=CH$_2$, —CH=CH—CH$_3$, —C$_2$H$_4$—CH=CH$_2$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH$_2$—CH=CH$_2$, —CH$_2$—CH=CH—CH$_3$, —CH(CH$_3$)—C$_2$H$_4$—CH=CH$_2$, —C$_2$H$_4$—CH=C(CH$_3$)$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —C(C$_4$H$_9$)=CH$_2$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —CH(CH$_3$)—CH$_2$—C(CH$_3$)=CH$_2$, —CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$(C$_2$H$_5$))—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_3$H$_7$)=CH—CH$_3$, —C(C$_2$H$_5$)=CH—C$_2$H$_5$, —C(C$_2$H$_5$)=C(CH$_3$)$_2$, —C[C(CH$_3$)$_3$]=CH$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —CH$_2$—CH=CH—CH$_2$—CH=CH$_2$, —CH=CH—C$_2$H$_4$—CH=CH$_2$, —CH$_2$—CH=CH—CH=CH—CH$_3$, —CH=CH—CH=CH—C$_2$H$_5$, —CH$_2$—CH=CH—C(CH$_3$)=CH$_2$, —CH$_2$—CH=C(CH$_3$)—CH=CH$_2$, —CH$_2$—C(CH$_3$)=CH—CH=CH$_2$, —CH(CH$_3$)—CH=CH—CH=CH$_2$, —CH=CH—CH$_2$—C(CH$_3$)=CH$_2$, —CH=CH—CH(CH$_3$)—CH=CH$_2$, —CH=C(CH$_3$)—CH$_2$—CH=CH$_2$, —C(CH$_3$)=CH—CH$_2$—CH=CH$_2$, —CH$_2$—CH=CH$_2$, —CH=CH—CH=C(CH$_3$)$_2$, —CH=CH—C(CH$_3$)=CH—CH$_3$, —CH=C(CH$_3$)—CH=CH—CH$_3$, —C(CH$_3$)=CH—CH=CH—CH$_3$, —CH=C(CH$_3$)—C(CH$_3$)=CH$_2$, —C(CH$_3$)=CH—C(CH$_3$)=CH$_2$, —C(CH$_3$)=C(CH$_3$)—CH=CH$_2$, —CH=CH—CH=CH—CH=CH$_2$, —C$_5$H$_{10}$—CH=CH$_2$, —C$_4$H$_8$—CH=CH—CH$_3$, —C$_3$H$_6$—CH=CH—C$_2$H$_5$, —C$_2$H$_4$—CH=CH—C$_3$H$_7$, —CH$_2$—CH=CH—C$_4$H$_9$, —C$_4$H$_8$—C(CH$_3$)=CH$_2$, —C$_3$H$_6$—CH(CH$_3$)—CH=CH$_2$, —C$_2$H$_4$—CH(CH$_3$)—CH$_2$—CH=CH$_2$, —CH$_2$—CH(CH$_3$)—C$_2$H$_4$—CH=CH$_2$, —C$_3$H$_6$—CH=C(CH$_3$)$_2$, —C$_3$H$_6$—C(CH$_3$)=CH—CH$_3$, —C$_2$H$_4$—CH(CH$_3$)—CH=CH—CH$_3$, —CH$_2$—CH(CH$_3$)—CH$_2$—CH=CH—CH$_3$, —C$_2$H$_4$—CH=CH—CH(CH$_3$)$_2$, —C$_2$H$_4$—C(CH$_3$)=CH—C$_2$H$_5$, —C$_2$H$_4$—CH=C(CH$_3$)—C$_2$H$_5$, —CH$_2$—CH(CH$_3$)—CH=CH—C$_2$H$_5$, —CH$_2$—CH=CH—CH$_2$—CH(CH$_3$)$_2$, —CH$_2$—CH=CH—CH(CH$_3$)—C$_2$H$_5$, —CH$_2$—CH=C(CH$_3$)—C$_3$H$_7$, —CH$_2$—C(CH$_3$)=CH—C$_3$H$_7$, —C$_2$H$_4$—CH(CH$_3$)—C(CH$_3$)=CH$_2$, —CH$_2$—CH(CH$_3$)—CH$_2$—C(CH$_3$)=CH$_2$, —CH$_2$—CH(CH$_3$)—CH(CH$_3$)—CH=CH$_2$, —C$_2$H$_4$—C(CH$_3$)$_2$—CH=CH$_2$, —CH$_2$—C(CH$_3$)$_2$—CH$_2$—CH=CH$_2$, —C$_2$H$_4$—C(CH$_3$)=C(CH$_3$)$_2$, —CH$_2$—CH(CH$_3$)—CH=C(CH$_3$)$_2$, —CH$_2$—C(CH$_3$)$_2$—CH=CH—CH$_3$, —CH$_2$—CH(CH$_3$)—C(CH$_3$)=CH—CH$_3$, —CH$_2$—CH=C(CH$_3$)—CH(CH$_3$)$_2$, —CH$_2$—C(CH$_3$)=CH—CH(CH$_3$)$_2$, —CH$_2$—C(CH$_3$)=C(CH$_3$)—C$_2$H$_5$, —CH$_2$—CH=CH—C(CH$_3$)$_3$, —CH$_2$—C(CH$_3$)$_2$—C(CH$_3$)=CH$_2$, —CH$_2$—CH(C$_2$H$_5$)—C(CH$_3$)=CH$_2$, —CH$_2$—C(CH$_3$)(C$_2$H$_5$)—CH=CH$_2$, —CH$_2$—CH(CH$_3$)—C(C$_2$H$_5$)=CH$_2$, —C$_2$H$_4$—C(C$_3$H$_7$)=CH$_2$, —C$_2$H$_4$—C(C$_2$H$_5$)=CH—CH$_3$, —CH$_2$—CH(C$_2$H$_5$)—CH=CH—CH$_3$, —CH$_2$—C(C$_4$H$_9$)=CH$_2$, —CH$_2$—C(C$_3$H$_7$)=CH—CH$_3$, —CH$_2$—C(C$_2$H$_5$)=CH—C$_2$H$_5$, —CH$_2$—C(C$_2$H$_5$)=C(CH$_3$)$_2$, —CH$_2$—C[C(CH$_3$)$_3$]=CH$_2$, —CH$_2$—C[CH(CH$_3$)(C$_2$H$_5$)]=CH$_2$, —CH$_2$—C[CH$_2$—CH(CH$_3$)$_2$]=CH$_2$, —C$_3$H$_6$—CH=CH—CH=CH$_2$, —C$_2$H$_4$—CH=CH—CH$_2$—CH=CH$_2$, —CH$_2$—CH=CH—C$_2$H$_4$—CH=CH$_2$, —C$_2$H$_4$—CH=CH—CH=CH—CH$_3$, —CH$_2$—CH=CH—CH$_2$—CH=CH—CH$_3$, —CH$_2$—CH=CH—CH=CH—C$_2$H$_5$, —C$_2$H$_4$—CH=CH—C(CH$_3$)=CH$_2$, —C$_2$H$_4$—CH=C(CH$_3$)—CH=CH$_2$, —C$_2$H$_4$—C(CH$_3$)=CH—CH=CH$_2$, —CH$_2$—CH(CH$_3$)—CH=CH—CH=CH$_2$, —CH$_2$—CH=CH—CH(CH$_3$)—CH=CH$_2$, —CH$_2$—CH=C(CH$_3$)—CH$_2$—CH=CH$_2$, —CH$_2$—C(CH$_3$)=CH—CH$_2$—CH=CH$_2$, —CH$_2$—CH=CH—CH=C(CH$_3$)$_2$, —CH$_2$—CH=CH—C(CH$_3$)=CH—CH$_3$, —CH$_2$—CH=C(CH$_3$)—CH=CH—CH$_3$, —CH$_2$—C(CH$_3$)=CH—CH=CH—CH$_3$, —CH$_2$—CH=C(CH$_3$)—C(CH$_3$)=CH$_2$, —CH$_2$—C(CH$_3$)=CH—C(CH$_3$)=CH$_2$, —CH$_2$—C(CH$_3$)=C(CH$_3$)—CH=CH$_2$, —CH$_2$—CH=CH—CH=CH—CH=CH$_2$, —C$_6$H$_{12}$—CH=CH$_2$, —C$_5$H$_{10}$—CH=CH—CH$_3$, —C$_4$H$_8$—CH=CH—C$_2$H$_5$, —C$_3$H$_6$—CH=CH—C$_3$H$_7$, —C$_2$H$_4$—CH=CH—C$_4$H$_9$, —C$_5$H$_{10}$—C(CH$_3$)=CH$_2$, —C$_4$H$_8$—CH(CH$_3$)—CH=CH$_2$, —C$_3$H$_6$—CH(CH$_3$)—CH$_2$—CH=CH$_2$, —C$_2$H$_4$—CH(CH$_3$)—C$_2$H$_4$—CH=CH$_2$, —C$_4$H$_8$—CH=C(CH$_3$)$_2$, —C$_4$H$_8$—C(CH$_3$)=CH—CH$_3$, —C$_3$H$_6$—CH(CH$_3$)—CH=CH—CH$_3$, —C$_2$H$_4$—CH(CH$_3$)—CH$_2$—CH=CH—CH$_3$, —C$_3$H$_6$—CH=CH—CH(CH$_3$)$_2$, —C$_3$H$_6$—CH=C(CH$_3$)—C$_2$H$_5$, —C$_3$H$_6$—C(CH$_3$)=CH—C$_2$H$_5$, —C$_2$H$_4$—CH(CH$_3$)—CH=CH—C$_2$H$_5$, —C$_2$H$_4$—CH=CH—CH$_2$—CH(CH$_3$)$_2$, —C$_2$H$_4$—CH=CH—CH(CH$_3$)—C$_2$H$_5$, —C$_2$H$_4$—CH=C(CH$_3$)—C$_3$H$_7$, —C$_2$H$_4$—C(CH$_3$)=CH—C$_3$H$_7$, —C$_3$H$_6$—CH(CH$_3$)—C(CH$_3$)=CH$_2$, —C$_2$H$_4$—CH(CH$_3$)—CH$_2$—C(CH$_3$)=CH$_2$, —C$_2$H$_4$—CH(CH$_3$)—CH(CH$_3$)—CH=CH$_2$, —C$_3$H$_6$—C(CH$_3$)$_2$—CH=CH$_2$, —C$_2$H$_4$—C(CH$_3$)$_2$—CH$_2$—CH=CH$_2$, —C$_3$H$_6$—C(CH$_3$)=C(CH$_3$)$_2$, —C$_2$H$_4$—CH(CH$_3$)—CH=C(CH$_3$)$_2$, —C$_2$H$_4$—C(CH$_3$)$_2$—CH=CH—CH$_3$, —C$_2$H$_4$—CH(CH$_3$)—C(CH$_3$)=CH—CH$_3$, —C$_2$H$_4$—CH=C(CH$_3$)—CH(CH$_3$)$_2$, —C$_2$H$_4$—C(CH$_3$)=CH—CH(CH$_3$)$_2$, —C$_2$H$_4$—C(CH$_3$)=C(CH$_3$)—C$_2$H$_5$, —C$_2$H$_4$—CH=CH—C(CH$_3$)$_3$, —C$_2$H$_4$—C(CH$_3$)$_2$—C(CH$_3$)=CH$_2$, —C$_2$H$_4$—CH(C$_2$H$_5$)—C(CH$_3$)=CH$_2$, —C$_2$H$_4$—C(CH$_3$)(C$_2$H$_5$)—CH=CH$_2$, —C$_2$H$_4$—CH(CH$_3$)—C(C$_2$H$_5$)=CH$_2$, —C$_3$H$_6$—C(C$_3$H$_7$)=CH$_2$, —C$_3$H$_6$—C(C$_2$H$_5$)=CH—CH$_3$, —C$_2$H$_4$—CH(C$_2$H$_5$)—CH=CH—CH$_3$, —C$_2$H$_4$—C(C$_4$H$_9$)=CH$_2$, —C$_2$H$_4$—C(C$_3$H$_7$)=CH—CH$_3$, —C$_2$H$_4$—C(C$_2$H$_5$)=CH—C$_2$H$_5$, —C$_2$H$_4$—C(C$_2$H$_5$)=C(CH$_3$)$_2$, —C$_2$H$_4$—C[C(CH$_3$)$_3$]=CH$_2$, —C$_2$H$_4$—C[CH(CH$_3$)(C$_2$H$_5$)]=CH$_2$, —C$_2$H$_4$—C[CH$_2$—CH(CH$_3$)$_2$]=CH$_2$, —C$_4$H$_8$—CH=CH—CH=CH$_2$, —C$_3$H$_6$—CH=CH—CH$_2$—CH=CH$_2$, —C$_2$H$_4$—CH=CH—C$_2$H$_4$—CH=CH$_2$, —C$_3$H$_6$—CH=CH—CH=CH—CH$_3$, —C$_2$H$_4$—CH=CH—CH$_2$—CH=CH—CH$_3$, —C$_2$H$_4$—CH=CH—CH=CH—C$_2$H$_5$, —C$_3$H$_6$—CH=CH—C(CH$_3$)=CH$_2$, —C$_3$H$_6$—CH=C(CH$_3$)—CH=CH$_2$, —C$_3$H$_6$—C(CH$_3$)=CH—CH=CH$_2$, —C$_2$H$_4$—CH(CH$_3$)—CH=CH—CH=CH$_2$, —C$_2$H$_4$—CH=CH—CH$_2$—C(CH$_3$)=CH$_2$, —C$_2$H$_4$—CH=CH—CH(CH$_3$)—CH=CH$_2$, —C$_2$H$_4$—CH=C(CH$_3$)—CH$_2$—CH=CH$_2$, —C$_2$H$_4$—C(CH$_3$)=CH—CH$_2$—CH=CH$_2$, —C$_2$H$_4$—CH=CH—CH=C(CH$_3$)$_2$, —C$_2$H$_4$—CH=CH—C(CH$_3$)=CH—CH$_3$, —C$_2$H$_4$—CH=C(CH$_3$)—CH=CH—CH$_3$, —C$_2$H$_4$—C(CH$_3$)=CH—CH=CH—CH$_3$, —C$_2$H$_4$—CH=C(CH$_3$)—C(CH$_3$)=CH$_2$, —C$_2$H$_4$—C(CH$_3$)=CH—C(CH$_3$)=CH$_2$, —C$_2$H$_4$—C(CH$_3$)=C(CH$_3$)—CH=CH$_2$ and —C$_2$H$_4$—CH=CH—CH=CH—CH=CH$_2$, As used herein, the term alkylenyl refers to preferably "linear or branched C$_1$-C$_4$-alkylenyl" such as

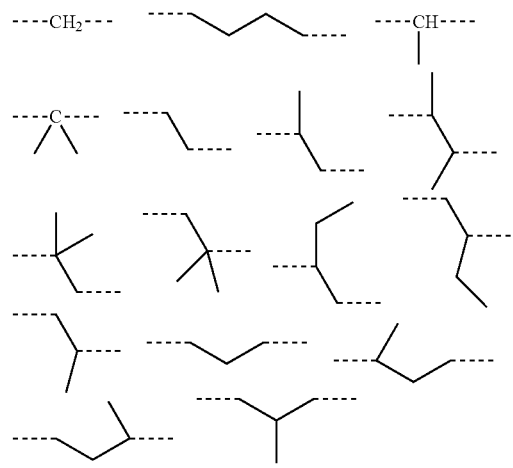

Preferred examples of modified hydroxylgroups of carbohydrate monomers of the carbohydrate antigen A are

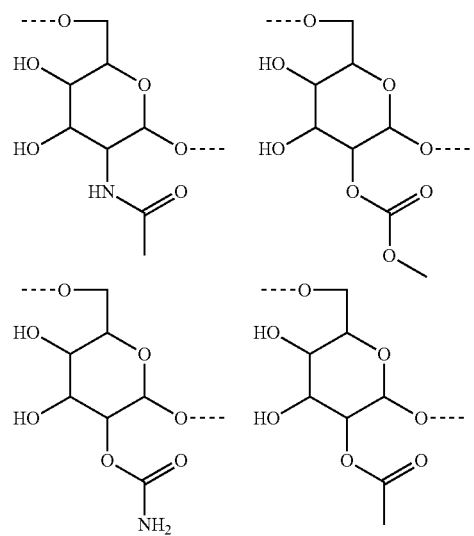

-continued

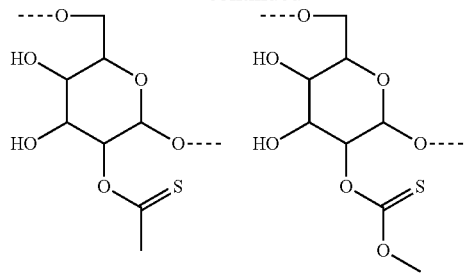
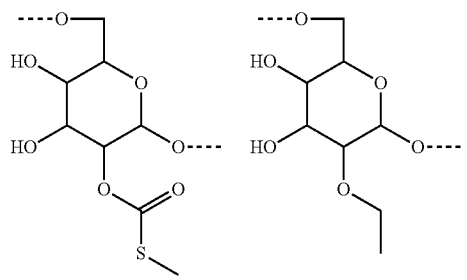
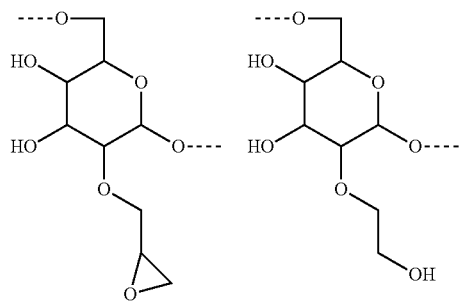
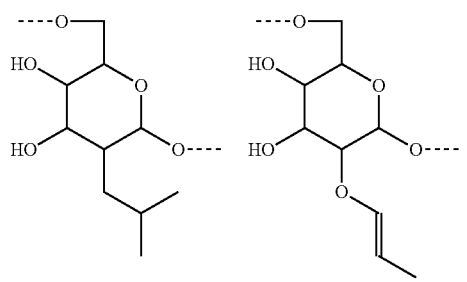
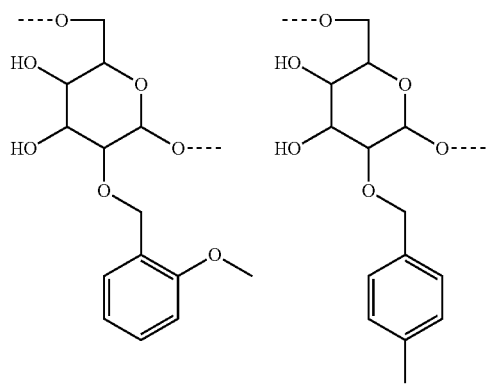

-continued

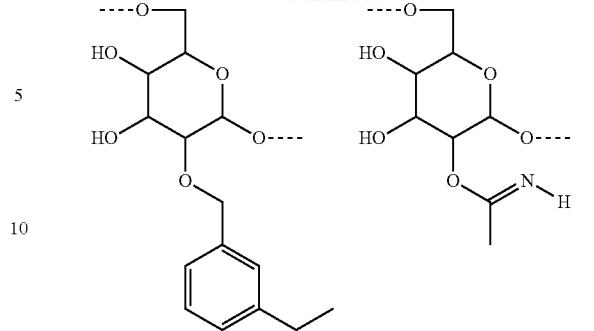
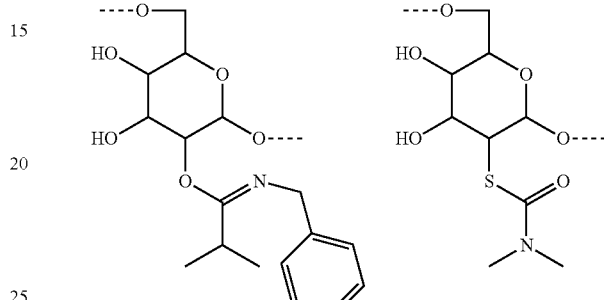
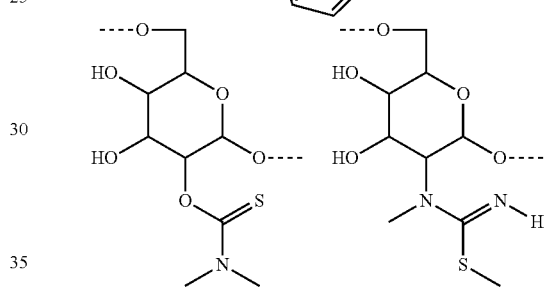
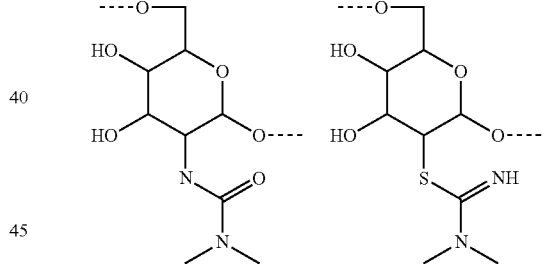

Modified hydroxylgroups of carbohydrate monomers of the carbohydrate antigen A may be formed by the activation of the carbohydrate antigen in order to couple the residues -L-CH—CA to the carbohydrate antigen. Since not all activated groups of the carbohydrate antigen are thereafter coupled to one of the residues -L-CH—CA, activated groups of the carbohydrate antigen remain which are not converted to an antigen linker (A-L) linkage. Such activated but not converted groups of the carbohydrate antigen are normally hydrolyzed during work-up of the $A[L-CH—CA]_p$ complex and remain on the carbohydrate antigen A as amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties.

That means, in case the carbohydrate antigen A is activated to form the covalent bond to the residues -L-CH—CA, the originally isolated or synthesized antigen is modified to bear such amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties.

Only in case the residue -L-CH—CA is activated at the L-terminus to form the covalent bond to the carbohydrate antigen A, the functional groups of the carbohydrate antigen A which are not linked to the residues -L-CH—CA remain unaltered.

Generally the carbohydrate antigen consists of a plurality of carbohydrate monomers, wherein each carbohydrate monomer has further more than one functionality which could be used for a covalent linkage of the residue -L-CH—CA, thus more than one residue -L-CH—CA and generally a larger number of residues -L-CH—CA is bound to the carbohydrate antigen A. It is clear to a skilled person that the more residues -L-CH—CA can be bound to one carbohydrate antigen the more carbohydrate monomers are contained in said carbohydrate antigen. For instance, a carbohydrate antigen consisting of 2 (u=2) carbohydrate monomers can bear 1, 2, 3 or 4 residues -L-CH—CA, while a carbohydrate antigen consisting of 50 (u=50) carbohydrate monomers might bear between 2 and 50 residues -L-CH—CA, and a carbohydrate antigen consisting of 3,000 (u=3000) carbohydrate monomers might have between 50 and 400 residues -L-CH—CA.

The bonding mode is represented by the integer p. p is the number of residues -L-CH—CA which are bound to the carbohydrate antigen A.

p represents an integer from 1 to ($\Phi$*u), wherein $\Phi$ represents the following integers: $\Phi$=2 (if u is 1 to 4); $\Phi$=1 (if u is 5 to 10); $\Phi$=0.5 (if u is 11 to 100); $\Phi$=0.2 (if u is 101 to 1000); $\Phi$=0.04 (if u is 1001 to 10000); wherein u is the number of carbohydrate monomers of the carbohydrate antigen A.

In another preferred embodiment of the invention p is an integer and is defined as follows:
p is 1 or 2 if u is 1
p is 1, 2, 3 or 4 if u is 2
p is 1, 2, 3, 4, 5 or 6 if u is 3
p is 1, 2, 3, 4, 5, 6, 7 or 8 if u is 4
$1 \leq p \leq 10$ if $5 \leq u \leq 10$
$2 \leq p \leq 50$ if $11 \leq u \leq 100$
$20 \leq p \leq 200$ if $101 \leq u \leq 1000$
$50 \leq p \leq 400$ if $1001 \leq u \leq 10000$
wherein u is the number of carbohydrate monomers of the carbohydrate antigen A.

In a preferred embodiment of this invention p is an integer falling within the range from $0.02 \, u \leq p \leq (0.7 \, u+3)$ with the proviso that $p \geq 1$, wherein u is an integer from 1 to 10000, representing the total number of carbohydrate monomers within the carbohydrate antigen A.

In order to connect the linker L or respectively the moiety -L-CH—CA to the carbohydrate antigen, two ways are possible. On the one hand the antigen could be activated and than reacted with the linker L or the moiety -L-CH—CA or on the other hand the linker L could be activated and than reacted with the antigen.

In case the linker L is activated in order to form a covalent bond with the carbohydrate antigen the number p of -L-CH—CA moieties present in the carbohydrate antigen depends on the molar equivalents of the moieties -L-CH—CA in regard to the number u of carbohydrate monomers present in the carbohydrate antigen. Thus, if u=100, i.e. the carbohydrate antigen A consists of 100 carbohydrate monomers, one molar equivalent of the moiety -L-CH—CA means that each carbohydrate antigen A bears only one moiety -L-CH—CA, while 50 molar equivalents of the moiety -L-CH—CA means, that in average every second carbohydrate monomer of the carbohydrate antigen A has one moiety -L-CH—CA, while 200 molar equivalents means that in average each carbohydrate monomer of the carbohydrate antigen A has two moieties -L-CH—CA.

In case the carbohydrate antigen A is activated and not the linker L, the carbohydrate antigen normally comprises a larger number of activated groups which are theoretically all possible to form a covalent bond with the linker L or respectively with the moiety -L-CH—CA. Generally not all activated groups of the carbohydrate antigen A are reacted with the linker L or respectively with the moiety -L-CH—CA, thus several activated groups remain in the carbohydrate antigen after reaction with the linker L or respectively with the moiety -L-CH—CA. These remaining activated groups normally react during workup of the reaction product of the activated carbohydrate antigen with the linker L or respectively with the moiety -L-CH—CA. Thus during workup these remaining activated groups of the carbohydrate antigen A are, for instance, hydrolyzed, oxidized, isomerized, cyclized and/or crosslinked. During work up and especially during aqueous workup these remaining activated groups are, for instance, converted to amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties.

The activated groups which can be converted to the amide, carbonate, carbamate, carbonyl, thiocarbonyl, carboxy, thiocarboxy, ester, thioester, ether, epoxy, hydroxyalkyl, alkylene, phenylene, alkenyl, imino, imide, isourea, thiocarbamate, thiourea and urea moieties are, for instance, cyano, chloro, bromo, iodo, azido, imino groups, vinyl, styryl and allyl groups, anhydrides, oxiranes, cyanates, isocyanates, thiocyanates, isothiocyanates, triazines and especially 1,3,5-triazines, imidazoles, methoxy ethers as well as sulfonyl groups such as para-toluenesulfonyl (Ts-), trifluoromethanesulfonyl (Tf-, $CF_3SO_2$—), benzenesulfonyl ($C_6H_5SO_2$—) or methanesulfonyl (Ms-).

In the following more specific examples for such activated groups are given. The activation method comprising the modification of the functional groups of the carbohydrate monomers of the carbohydrate antigen may lead to the formation of activated moieties which are covalently bound to heteroatoms (N, O, S) of the functionalities of the carbohydrate antigen, wherein the activated moieties preferably belong to the following group comprising or consisting of:

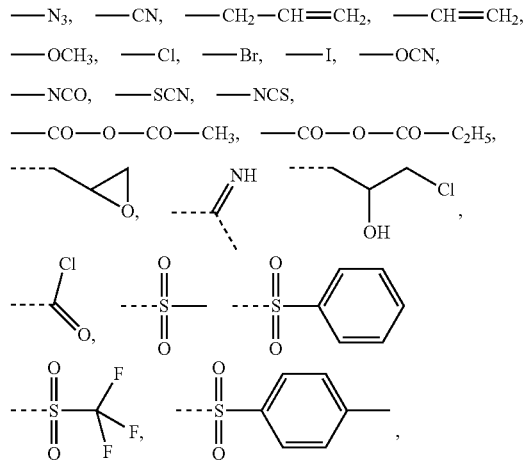

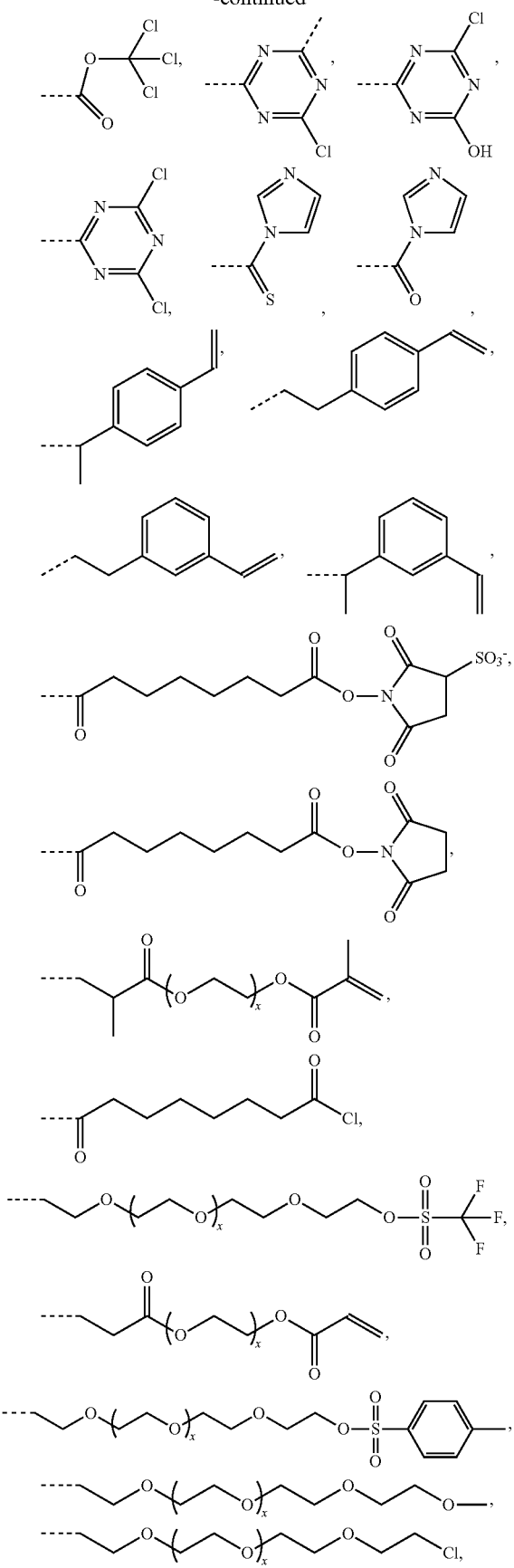
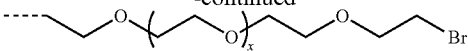

wherein x is in integer from 1 to 60.

Thus, the modification of the carbohydrate monomers of the carbohydrate antigen also implies that the carbohydrate monomers comprise or contain amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties. That means, that the modification of the carbohydrate monomers of the carbohydrate antigen A implies that the functional groups of the carbohydrate monomers are modified to amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties.

Therefore, the optional modification of the carbohydrate monomers of the carbohydrate antigen may be the result of an activation method which comprises the reaction of the carbohydrate functionalities with one activation agent or several activation agents and wherein the activation agent or the activation agents may form especially after hydrolysis, oxidation, isomerization, cyclization and/or crosslinking amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties.

The mentioned activation agent or agents can be used for the coupling of the carbohydrate antigen to the linker L or respectively to the residues -L-CH—CA and preferably belong to the group comprising:

allylbromide, allylchloride, bis-NHS-esters like bis[sulfosuccinimidyl] suberate, cyanogen bromide, 1,4-cyclohexanedimethanol divinyl ether, 1,1'-carbonyldiimidazole (CDI), N,N'-(1,2-dihydroxyethylene)bisacrylamide, divinylbenzene, epichlorhydrin (ECH), ethylene-glycol-di(meth)acrylates, ethylene-glycol-diacrylates, N-hydroxysuccinimide (NHS), N-(1-hydroxy-2,2-dimethoxyethyl)-acrylamide, methylenebisacrylamides, 4,4'-methylenebis(cyclohexylisocyanate), 1,4-phenylenediacryloylchloride, phosgene, diphosgene, triphosgene, polyethylene-glycol-di(meth)acrylates, polyethylene-glycol-diacrylates, tetraethylene glycol dimethyl ether, 1,1'-thiocarbonyldiimidazol (TCDI), thiophosgene, 2,4,6-trichlorotriazine (TCT).

In case the carbohydrate antigen A is activated, the activation method leads to a conversion of the functionalities of the carbohydrate monomers of the carbohydrate antigen into activated species which react with the residues -L-CH—CA in a further step.

Not all of the activated groups of the carbohydrate antigen A react with the residues -L-CH—CA and may therefore hydrolize, oxidize, isomerize, cyclize or crosslink with other sugar moieties of the carbohydrate antigen during workup to form hydrolized, oxidized, isomerized, cyclized or crosslinked residues. These hydrolized, oxidized, isomerized, cyclized or crosslinked residues derive from the activation agent itself and their chemistry due to hydrolysis, oxidation, isomerization, cyclization or crosslinking reactions. The hydrolized, oxidized, isomerized, cyclized or crosslinked residues are covalently bound to any hetero atom (N, O, S) of the functionalities of the carbohydrate monomers of the carbohydrate antigen, and belong preferably to the group comprising or consisting of:

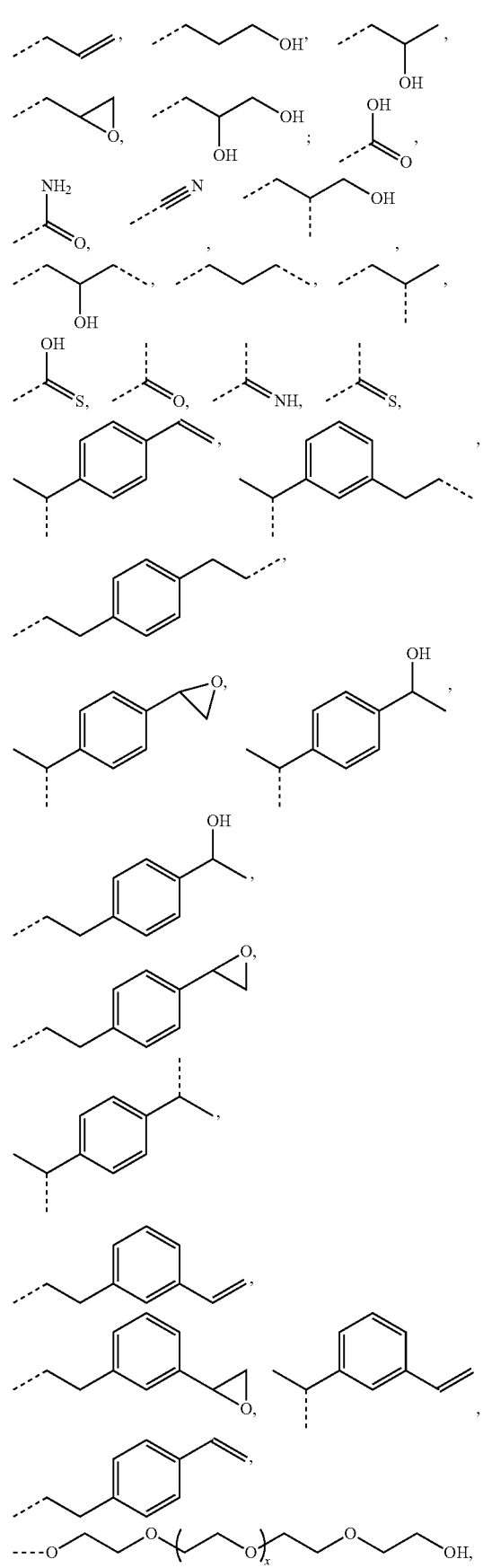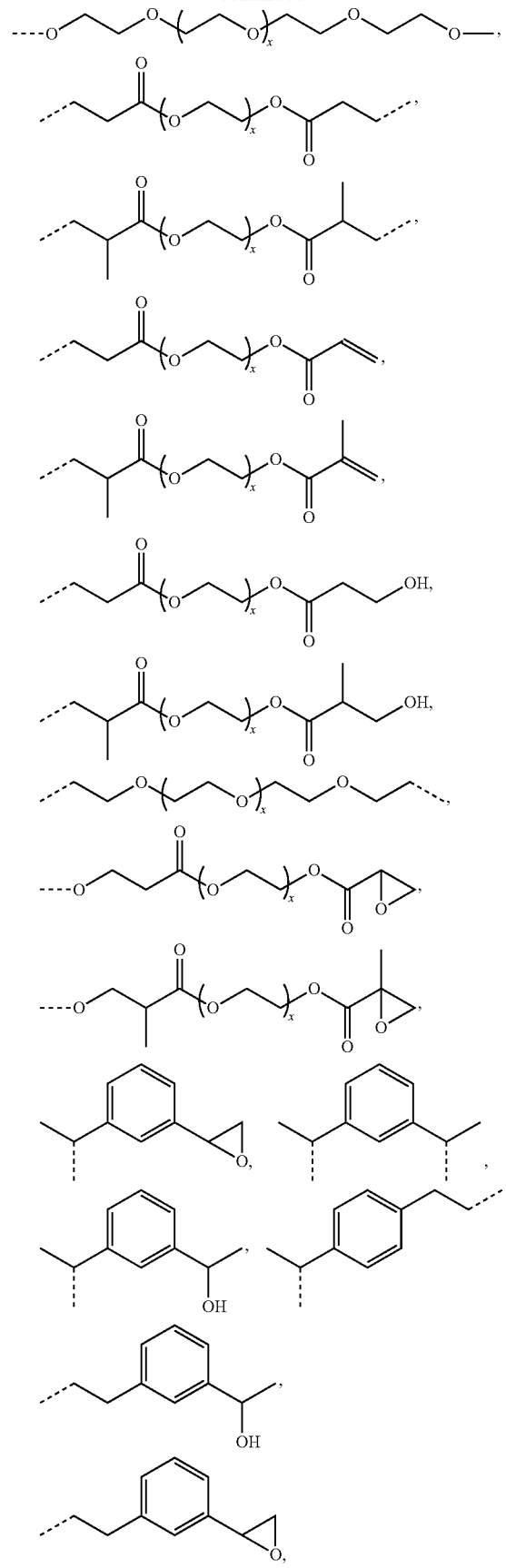

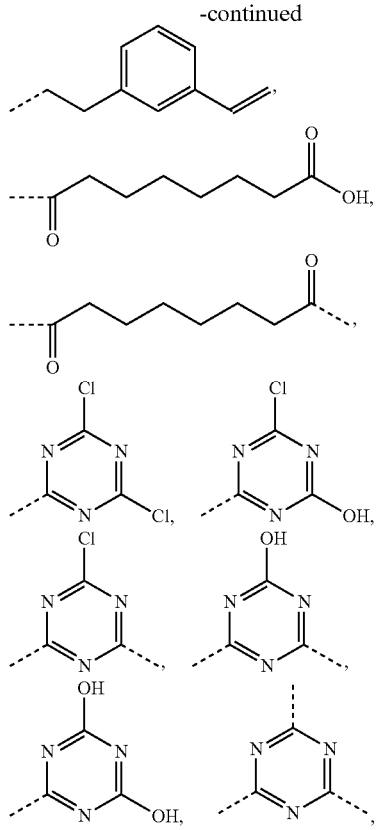

wherein x is in integer from 1 to 60.

The modification of the functionalities of the carbohydrate monomers of the carbohydrate antigen comprises the reaction of the functionalities of the carbohydrate monomers of the carbohydrate antigen with one activation agent or activation agents and/or with the activated linker L or respectively the activated linker L in -L-CH—CA or when the carbonhydrate monomers of the carbohydrate antigen with the non-activated linker to form a covalent bond between the hetero atom (N, O, S) of the functionality of the carbohydrate monomer or the modified carbohydrate monomer and the activation agent and/or with the activated or non-activated linker L. The formation of this covalent bond is accompanied by the cleavage of a N—H, O—H or S—H bond and the loss of a H-atom. Possible reactions for the formation of this covalent bond are belonging to the group comprising nucleophilic substitution, esterification, etherification, amidation, acylation.

The carbohydrate monomers of the carbohydrate antigen A preferably belong to hexoses, pentoses, tetroses or sialic acids.

In a preferred embodiment of the invention, the sialic acids belong to the group of N- or O-substituted derivatives of neuraminic acid of the following formula:

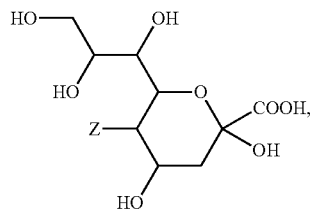

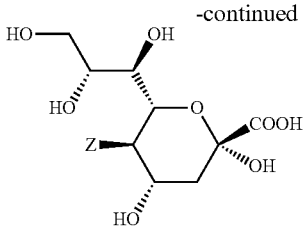

wherein Z represents —NH$_2$, —NHAc, or —OH.

In case such a sialic acid carbohydrate monomer is present in the carbohydrate antigen A, linkage to the subsequent carbohydrate monomer is achieved through a glycosidic bond (and replacement of the corresponding hydrogen atom at the glycosidic hydroxyl group) and/or through linkage of another carbohydrate monomer to one of the hydroxyl groups of the sialic acid by replacement of the corresponding hydrogen atom at this hydroxyl group.

In a preferred embodiment the sialic acid carbohydrate monomer represents within the building block A as follows:

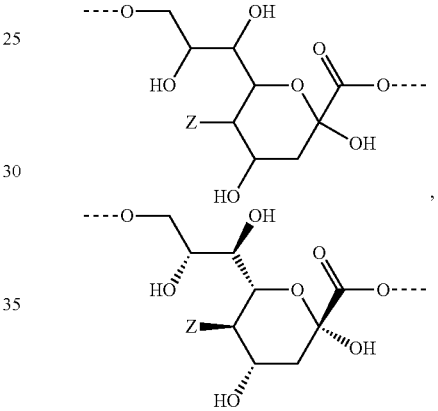

wherein Z represents —NH$_2$, —NHAc, or —OH.

In a preferred embodiment of the invention, the used carbohydrate monomers of the A-moiety belong to the following group of α- and β-D/L-carbohydrates comprising or consisting of:

α-D-ribopyranose, α-D-arabinopyranose, α-D-xylopyranose, α-D-lyxopyranose, α-D-allopyranose, α-D-altropyranose, α-D-glucopyranose, α-D-mannpyranose, α-D-glucopyranose, α-D-idopyranose, α-D-galactopyranose, α-D-talopyranose, α-D-psicopyranose, α-D-fructopyranose, α-D-sorbopyranose, α-D-tagatopyranose, α-D-ribofuranose, α-D-arabinofuranose, α-D-xylofuranose, α-D-lyxofuranose, α-D-Allofuranose, α-D-Altrofuranose, α-D-Glucofuranose, α-D-Mannofuranose, α-D-gulofuranose, α-D-idofuranose, α-D-galactofuranose, α-D-talofuranose, α-D-psicofuranose, α-D-fructofuranose, α-D-sorbofuranose, α-D-tagatofuranose, α-D-xylulofuranose, α-D-ribulofuranose, α-D-threofuranose, α-D-rhamnopyranose, α-D-erythrofuranose, α-D-glucosamine, α-D-glucopyranuronic acid, β-D-ribopyranose, β-D-arabinopyranose, β-D-xylopyranose, β-D-lyxopyranose, β-D-allopyranose, β-D-altropyranose, β-D-glucopyranose, β-D-mannpyranose, β-D-glucopyranose, β-D-idopyranose, β-D-galactopyranose, β-D-talopyranose, β-D-psicopyranose, β-D-fructopyranose, β-D-sorbopyranose, β-D-tagatopyranose, β-D-ribofuranose, β-D-arabinofuranose, β-D-xylofuranose, β-D-lyxofuranose, β-D-rhamnopyranose, β-D-allofuranose, β-D-altrofuranose, β-D-glucofuranose, β-D-mannofuranose, β-D-gulofuranose, β-D-idofuranose, β-D-galactofuranose, β-D-talofuranose, β-D-psicofuranose, β-D-fructofuranose, β-D-sorbofuranose, β-D-tagatofuranose, β-D-xylulofuranose, β-D-ribulofuranose, β-D-threofuranose, β-D-erythrofuranose, β-D-glucosamine, β-D-glucopyranuronic acid, α-L-ribopyranose, α-L-arabinopyranose, α-L-xylopyranose, α-L-lyxopyranose, α-L-allopyranose, α-L-altropyranose, α-L-glucopyranose, α-L-mannpyranose, α-L-glucopyranose, α-L-idopyranose, α-L-galactopyranose, α-L-talopyranose, α-L-psicopyranose, α-L-fructopyranose, α-L-sorbopyranose, α-L-tagatopyranose, α-L-rhamnopyranose, α-L-ribofuranose, α-L-arabinofuranose, α-L-xylofuranose, α-L-lyxofuranose, α-L-Allofuranose, α-L-Altrofuranose, α-L-Glucofuranose, α-L-Mannofuranose, α-L-gulofuranose, α-L-idofuranose, α-L-galactofuranose, α-L-talofuranose, α-L-psicofuranose, α-L-fructofuranose, α-L-sorbofuranose, α-L-tagatofuranose, α-L-xylulofuranose, α-L-ribulofuranose, α-L-threofuranose, α-L-erythrofuranose, α-L-glucosamine, α-L-glucopyranuronic acid, β-L-ribopyranose, β-L-arabinopyranose, β-L-xylopyranose, β-L-lyxopyranose, β-L-allopyranose, β-L-altropyranose, β-L-glucopyranose, β-L-mannpyranose, β-L-glucopyranose, β-L-idopyranose, β-L-galactopyranose, β-L-talopyranose, β-L-psicopyranose, β-L-fructopyranose, β-L-sorbopyranose, β-L-tagatopyranose, β-L-ribofuranose, β-L-arabinofuranose, β-L-xylofuranose, β-L-lyxofuranose, β-L-allofuranose, β-L-altrofuranose, β-L-glucofuranose, β-L-mannofuranose, β-L-gulofuranose, β-L-idofuranose, β-L-galactofuranose, β-L-talofuranose, β-L-psicofuranose, β-L-fructofuranose, β-L-sorbofuranose, β-L-tagatofuranose, β-L-xylulofuranose, β-L-ribulofuranose, β-L-threofuranose, β-L-erythrofuranose, β-L-glucosamine, β-L-glucopyranuronic acid, and β-L-rhamnopyranose.

In another preferred embodiment of the invention, the carbohydrate monomers of the A-moiety and the CH moiety are selected independently of each other from the group comprising or consisting of the following α- and β-D-carbohydrates:

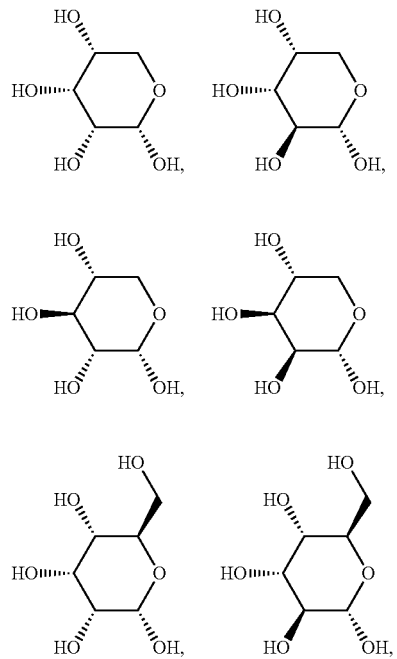

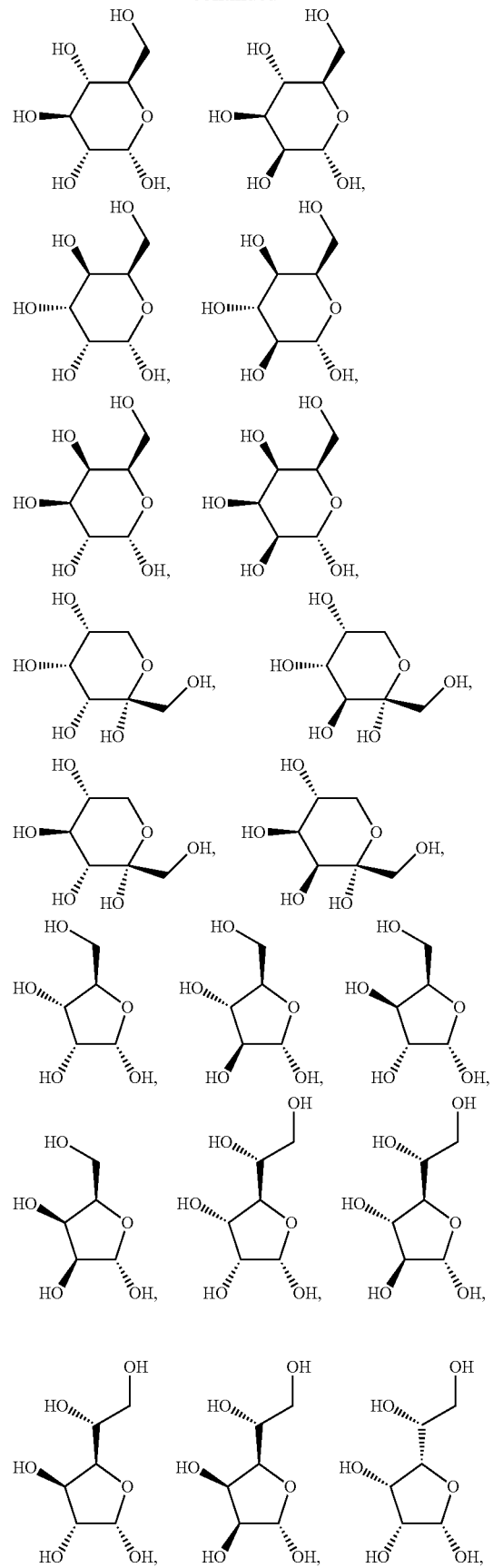

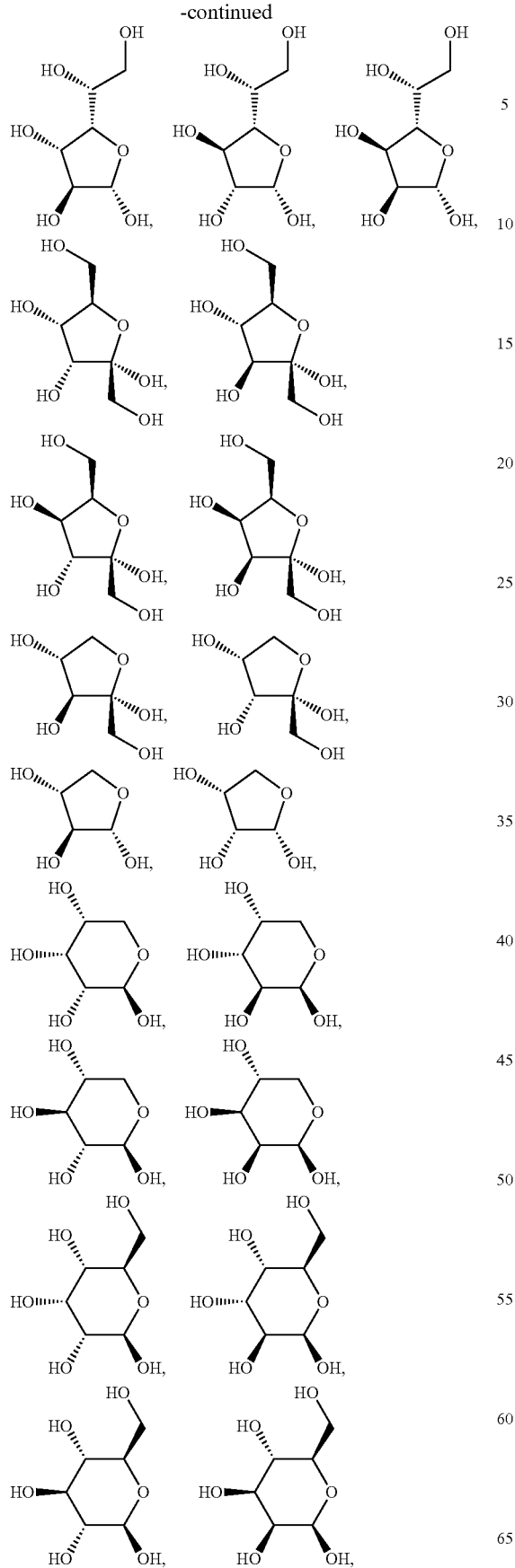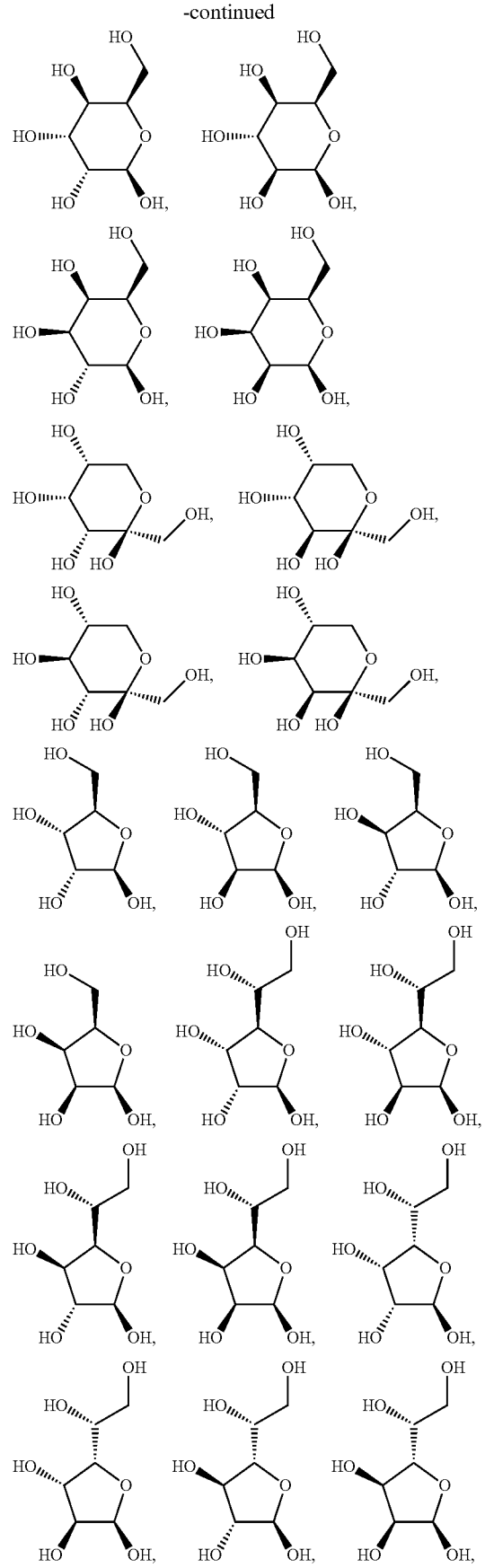

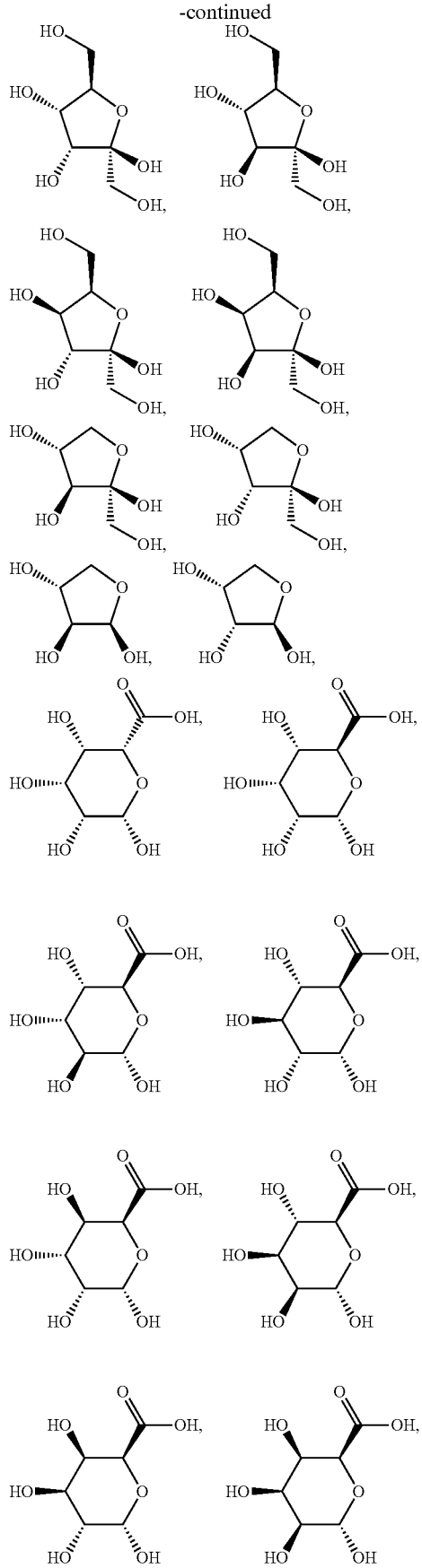
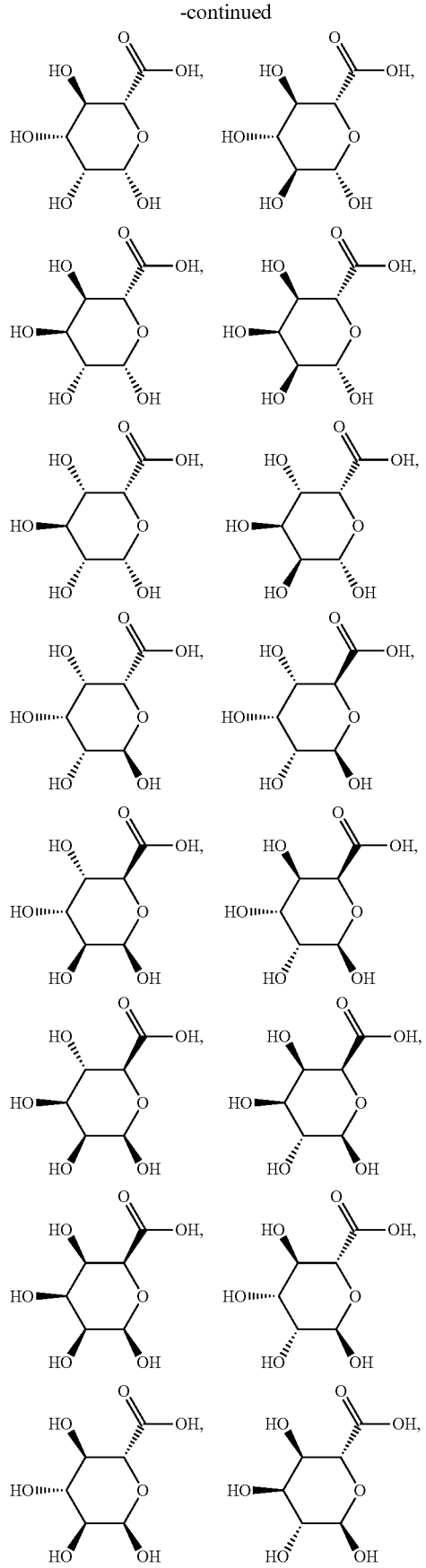

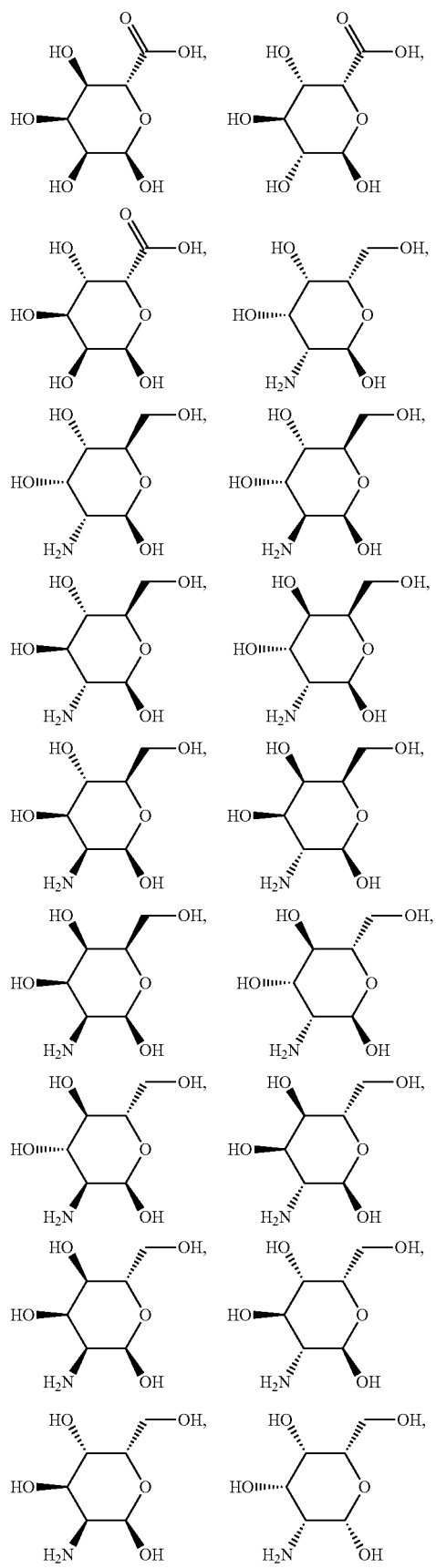
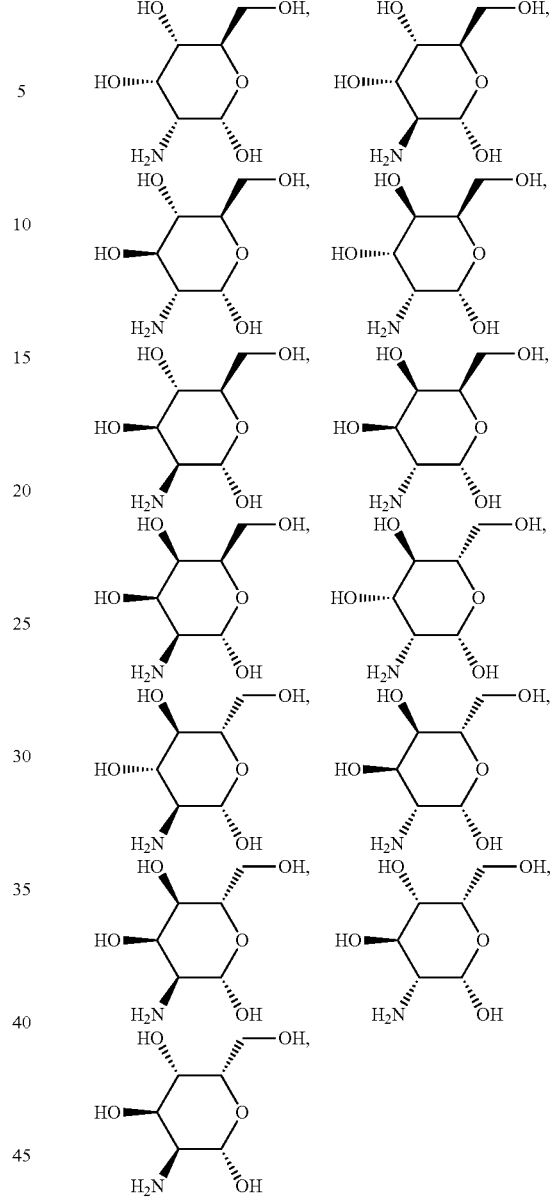

According to the present invention these carbohydrate monomers as defined herein are abundant in an antigen and occur as linking building block by deprotonation of two hydrogen atoms of different hydroxyl groups and formation of a bond to the rest of the molecule of the antigen A and to the moiety L, respectively.

L represents a linker moiety which is covalently bound to any atom, especially any hetero atom and most preferably any oxygen atom of a former hydroxyl group of the carbohydrate monomers of the carbohydrate antigen. Moreover the linker L is covalently bound to any hetero atom of CH and especially any oxygen atom of a hydroxyl group of CH. Thus, the linker molecule interconnects between the antigen A and the carbonhydrate moiety CH. Further, according to the present invention the interconnection between the antigen A and the carbonhydrate moiety CH occurs as described herein preferably by activation of the carbohydrate monomers of the carbohydrate antigen a and/or by activation of the linker molecule. Thereby, in a preferred embodiment of the present invention it is not merely connected the antigen A with the carbohydrate moiety CH via the linker L, but it is the interconnection between the antigen A and the carbohydrate moiety CH already bond to the ceramid CA forming the inventive compounds of the general formula (I)

$$A[L\text{-}CH\text{---}CA]_p \qquad (I).$$

The linker L can be subdivided into subunits -L$^1$-, -L$^2$- and -L$^3$- and can be formed of the subunits alone or of combinations thereof. Therefore, L may represent -L$^1$-L$^2$-, -L$^2$-, -L$^2$-L$^3$- or -L$^1$-L$^2$-L$^3$-. The preferred order of connectivity in the above cases with A and CH is as follows: A-L$^1$-L$^2$-CH—, A-L$^2$-CH—, A-L$^2$-L$^3$-CH— or A-L$^1$-L$^2$-L$^3$-CH—. However, it is also possible that the different fragments such as -L$^1$-L$^2$-, -L$^2$-, -L$^2$-L$^3$-, -L$^3$-L$^2$-L$^3$-, -L$^2$-L$^3$-L$^2$- or -L$^1$-L$^2$-L$^3$- are aligned in all possible orders as long as the connection between the different parts is chemically reasonable and possible.

The linker L may be bound to the carbohydrate moiety in such a manner that this bond can be cleaved in cell, e.g. a B help cell, a T help cell, in order to release the fragment A-L on the one hand and the fragment —CH—CA on the other hand.

L may include the functionality or a fragment of the functionality derived from the activation of the carbohydrate monomers of the carbohydrate antigen. L is preferably covalently bound to any hetero atom (N, O, S) of the carbohydrate monomers of the carbohydrate antigen A. L$^1$ if present is covalently bound to the linker subunit L$^2$ preferably through the moiety Y, which could also be a chemical bond. L$^1$ is preferably selected from the following residues:

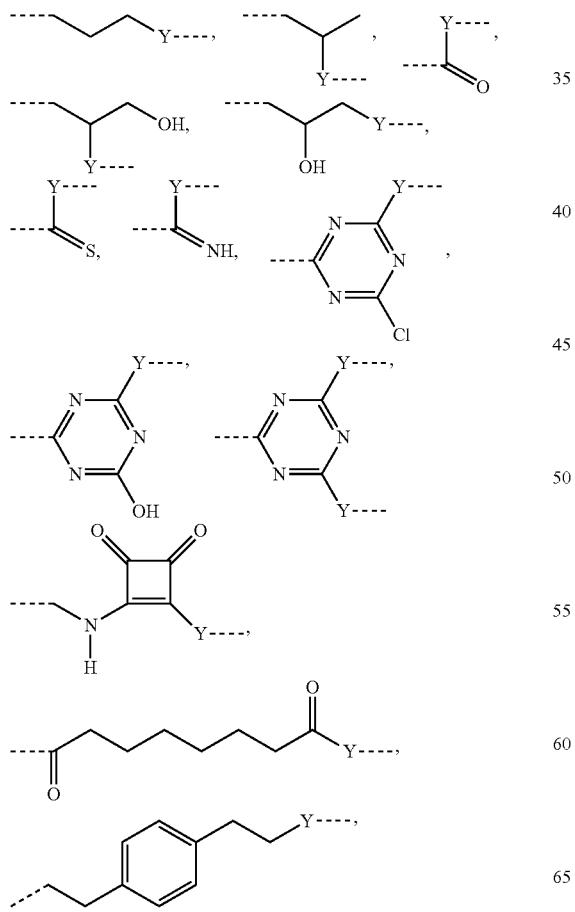

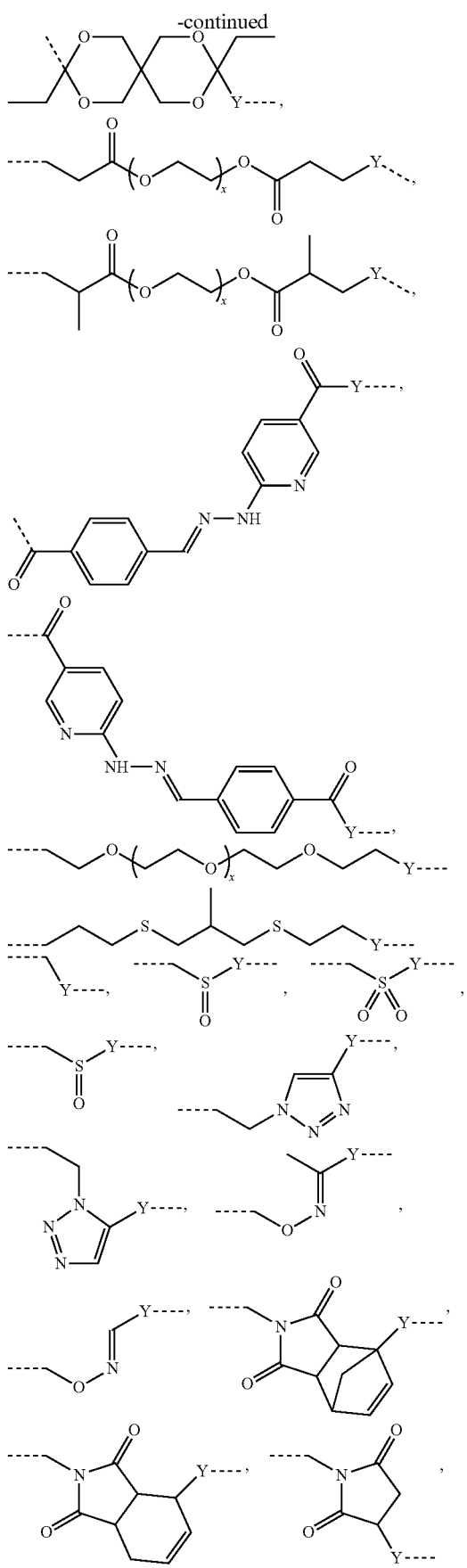

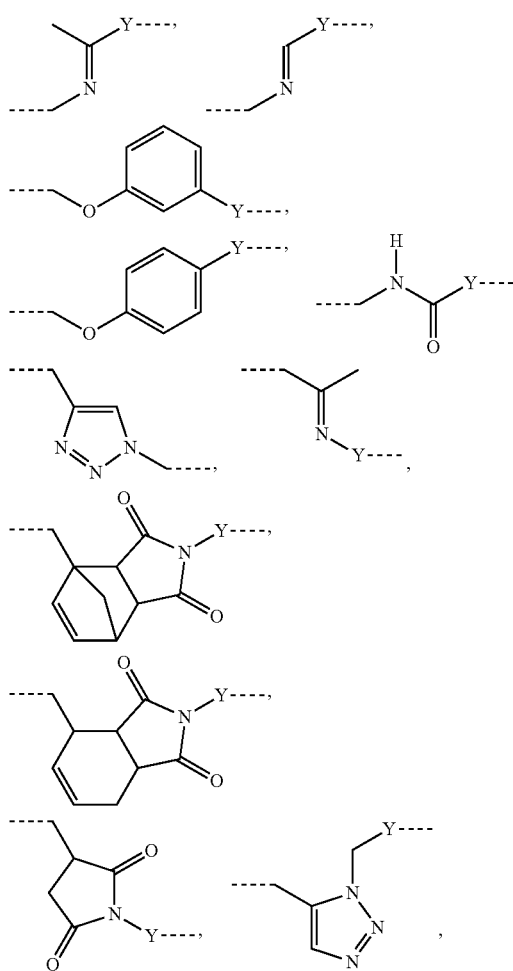

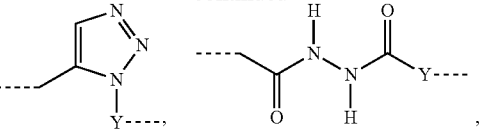

x is an integer from 1 to 60;
Y represents a bond, —NH—, —O—, —S—, —S—S—;
L² represents —CH₂—, —C₂H₄—, —C₃H₆—, —C₄H₈—, —C₅H₁₀—, —C₆H₁₂—, —C₇H₁₄—, —C₈H₁₆—, —C₉H₁₈—, —C₁₀H₂₀—, —CH(CH₃)—, —C[(CH₃)₂]—, —CH₂—CH(CH₃)—, —CH(CH₃)—CH₂—, —CH(CH₃)—C₂H₄—, —CH₂—CH(CH₃)—CH₂—, —C₂H₄—CH(CH₃)—, —CH₂—C[(CH₃)₂]—, —C[(CH₃)₂]—CH₂—, —CH(CH₃)—CH(CH₃)—, —C[(C₂H₅)(CH₃)]—, —CH(C₃H₇)—, —(CH₂—CH₂—O)ₙ—CH₂—CH₂—, —CO—CH₂—, —CO—C₂H₄—, —CO—C₃H₆—, —CO—C₄H₈—, —CO—C₅H₁₀—, —CO—C₆H₁₂—, —CO—C₇H₁₄—, —CO—C₈H₁₆—, —CO—C₉H₁₈—, —CO—C₁₀H₂₀—, —CO—CH(CH₃)—, —CO—C[(CH₃)₂]—, —CO—CH₂—CH(CH₃)—, —CO—CH(CH₃)—CH₂—, —CO—CH(CH₃)—C₂H₄—, —CO—CH₂—CH(CH₃)—CH₂—, —CO—C₂H₄—CH(CH₃)—, —CO—CH₂—C[(CH₃)₂]—, —CO—C[(CH₃)₂]—CH₂—, —CO—CH(CH₃)—CH(CH₃)—, —CO—C[(C₂H₅)(CH₃)]—, —CO—CH(C₃H₇)—, —CO—(CH₂—CH₂—O)ₙ—CH₂—CH₂—. L² is in case L³ is not present preferably linked to an oxygen atom of a former hydroxyl group of the carbohydrate residue CH.
n represents an integer from 1 to 60;
L³ represents —CO—, —O—CO—, —NH—CO—, —NH(C=NH)—, —SO₂—, —O—SO₂—, —NH—, —NH—CO—CH₂—. L³ if present is preferably linked to an oxygen atom of a former hydroxyl group of the carbohydrate residue CH.

Preferred examples for linker moieties L of the moiety A-L-CH—CA as at least one representative of all moieties in the compounds of the general formula (I) as defined herein are

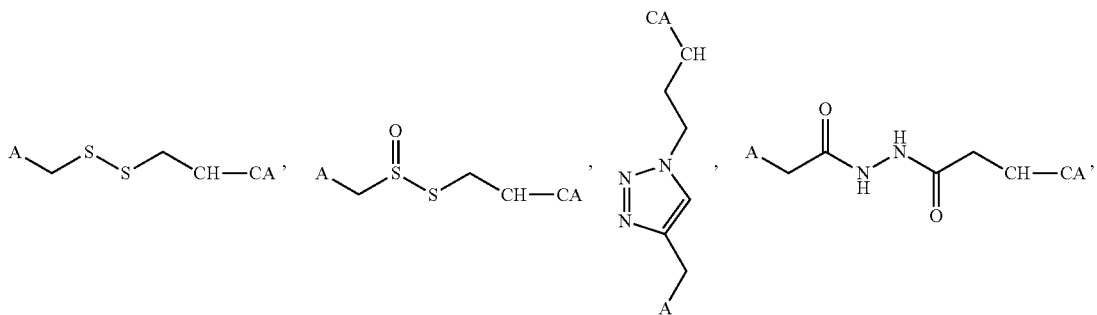

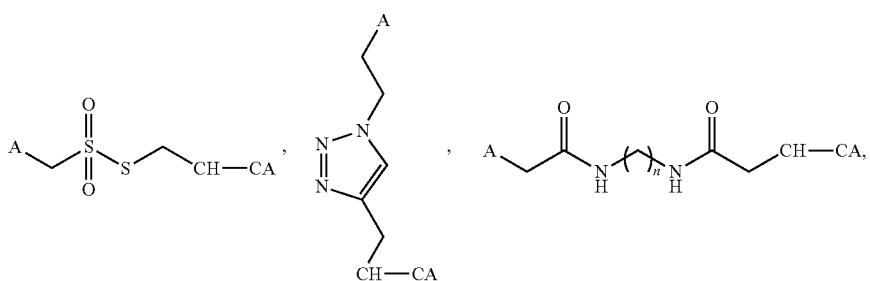

-continued

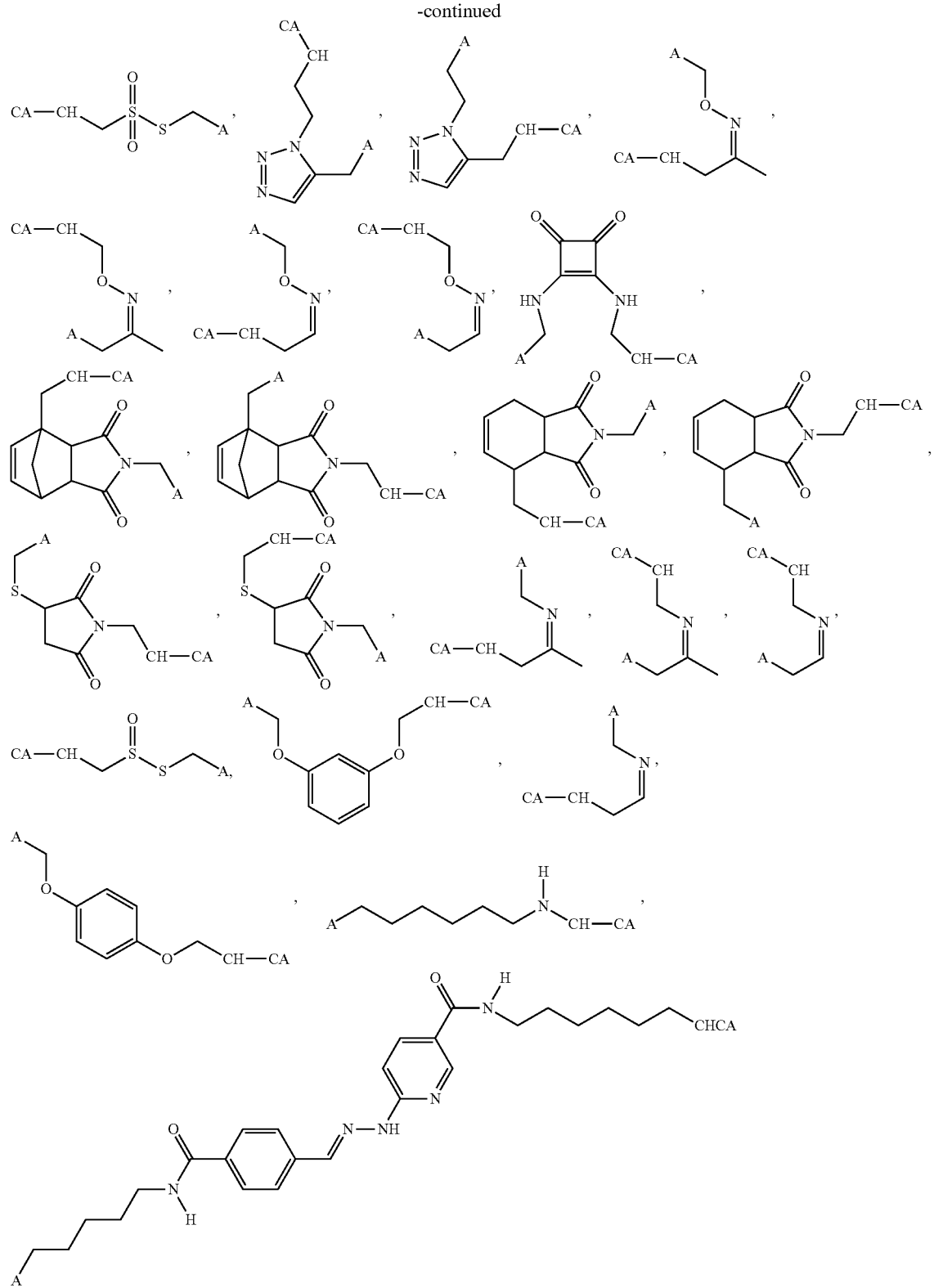

wherein n is as defined herein, and A, CH and CA represent an antigen, a carbohydrate moiety and a ceramid as defined herein.

The linker molecule L may optionally be further substituted with 1 to 3 of the substituents $Z^6$, $Z^7$, $Z^8$. However, it is clear to a skilled person that the term "can be substituted" refers to the replacement of a hydrogen atom by one of the substituents $Z^6$, $Z^7$, $Z^8$.

The substituents $Z^6$, $Z^7$ and $Z^8$ represent independently of each other —OH, —OCH$_3$, —OC$_2$H$_5$, —OC$_3$H$_7$, —O-cyclo-$C_3H_5$, —OCH($CH_3$)$_2$, —OC($CH_3$)$_3$, —O$C_4H_9$, —OPh, —O$CH_2$-Ph, —OCPh$_3$, —$CH_2$—O$CH_3$, —$C_2H_4$—O$CH_3$, —$C_3H_6$—O$CH_3$, —$CH_2$—O$C_2H_5$, —$C_2H_4$—O$C_2H_5$, —$C_3H_6$—O$C_2H_5$, —$CH_2$—O$C_3H_7$, —$C_2H_4$—O$C_3H_7$, —$C_3H_6$—O$C_3H_7$, —$CH_2$—O-cyclo-$C_3H_5$, —$C_2H_4$—O-cyclo-$C_3H_5$, —$C_3H_6$—O-cyclo-$C_3H_5$, —$CH_2$—OCH($CH_3$)$_2$, —$C_2H_4$—OCH($CH_3$)$_2$, —$C_3H_6$—OCH($CH_3$)$_2$, —$CH_2$—OC($CH_3$)$_3$, —$C_2H_4$—OC($CH_3$)$_3$, —$C_3H_6$—OC($CH_3$)$_3$, —$CH_2$—O$C_4H_9$, —$C_2H_4$—O$C_4H_9$, —$C_3H_6$—O$C_4H_9$, —$CH_2$—OPh, —$C_2H_4$—OPh, —$C_3H_6$—OPh, —$CH_2$—O$CH_2$-Ph, —$C_2H_4$—O$CH_2$-Ph, —$C_3H_6$—O$CH_2$-Ph, —$NO_2$, —F, —Cl, —Br, —CO$CH_3$, —CO$C_2H_5$, —CO$C_3H_7$, —CO-cyclo-$C_3H_5$, —COCH($CH_3$)$_2$, —COC($CH_3$)$_3$, —COOH, —COO$CH_3$, —COO$C_2H_5$, —COO$C_3H_7$, —COO-cyclo-$C_3H_5$, —COOCH($CH_3$)$_2$, —COOC($CH_3$)$_3$, —OOC—$CH_3$, —OOC—$C_2H_5$, —OOC—$C_3H_7$, —OOC-cyclo-$C_3H_5$, —OOC—CH($CH_3$)$_2$, —OOC—C($CH_3$)$_3$, —CON$H_2$, —CONH$CH_3$, —CONH$C_2H_5$, —CONH$C_3H_7$, —CONH-cyclo-$C_3H_5$, —CONH[CH($CH_3$)$_2$], —CONH[C($CH_3$)$_3$], —CON($CH_3$)$_2$, —CON($C_2H_5$)$_2$, —CON($C_3H_7$)$_2$, —CON(cyclo-$C_3H_5$)$_2$, —CON[CH($CH_3$)$_2$]$_2$, —CON[C($CH_3$)$_3$]$_2$, —NHCO$CH_3$, —NHCO$C_2H_5$, —NHCO$C_3H_7$, —NHCO-cyclo-$C_3H_5$, —NHCO—CH($CH_3$)$_2$, —NHCO—C($CH_3$)$_3$, —$NH_2$, —NHC$H_3$, —NH$C_2H_5$, —NH$C_3H_7$, —NH-cyclo-$C_3H_5$, —NHCH($CH_3$)$_2$, —NHC($CH_3$)$_3$, —N($CH_3$)$_2$, —N($C_2H_5$)$_2$, —N($C_3H_7$)$_2$, —N(cyclo-$C_3H_5$)$_2$, —N[CH($CH_3$)$_2$]$_2$, —N[C($CH_3$)$_3$]$_2$, —O$CF_3$, —$CH_2$—O$CF_3$, —$C_2H_4$—O$CF_3$, —$C_3H_6$—O$CF_3$, —O$C_2F_5$, —$CH_2$—O$C_2F_5$, —$C_2H_4$—O$C_2F_5$, —$C_3H_6$—O$C_2F_5$, —$CH_2$F, —CH$F_2$, —$CF_3$, —$CH_2$Cl, —$CH_2$Br, —$CH_2$—$CH_2$F, —$CH_2$—CH$F_2$, —$CH_2$—$CF_3$, —$CH_2$—$CH_2$Cl, —$CH_2$—$CH_2$Br.

The Carbohydrate Moiety CH

CH represents a monosaccharide, a disaccharide or a trisaccharide, wherein the carbohydrate monomers thereof preferably belong to hexoses, pentoses, tetroses. In case CH represents a monosaccharide, the carbohydrate monomer is identical to the monosaccharide. The disaccharide contains two carbohydrate monomers and the trisaccharide contains three carbohydrate monomers. In the disaccharide and trisaccharide the carbohydrate monomers are connected to each other via α/βglycosidic bonds which preferably belong to the group consisting of 1,2; 1,3; 1,4; 1,5; 1,6; 2,2; 2,3; 2,4; 2,5; or 2,6 glycosidic bonds.

The monosaccharide, the disaccharide and the trisaccharide CH are covalently bound to L and also to CA via a heteroatom (N, O, S) of the CH moiety and most preferably through an oxygen atom of a former hydroxyl group of CH.

As used herein the term "former hydroxyl group" means that the oxygen atom of a carbohydrate monomer which is now linked to L or CA was the oxygen atom of a hydroxyl group and linked to a hydrogen atom which is now replaced by the residue L or CA.

In a preferred embodiment of this invention, the monosaccharide, the disaccharide or the trisaccharide CH is covalently bound by one oxygen atom to L and through another oxygen atom to CA.

In another preferred embodiment of this invention, the monosaccharide, the disaccharide or the trisaccharide CH is covalently bound by one hydroxyl oxygen atom to L and through another hydroxyl oxygen atom to CA.

In another preferred embodiment of this invention, L or CA is bound to CH, i.e. to the monosaccharide, the disaccharide or the trisaccharide, by a glycosidic bond at C1 of the saccharide.

In a more preferred embodiment of this invention, L is bound by a glycosidic bond to C1 of the monosaccharide, the disaccharide or the trisaccharide and CA is bound by the oxygen at C6 of a hexose or by the oxygen at C5 of a pentose or by the oxygen at C4 of a tetrose.

In another more preferred embodiment of this invention, CA is bound by a glycosidic bond to C1 of the monosaccharide, the disaccharide or the trisaccharide and L is bound by the oxygen at C6 of a hexose or by the oxygen at C5 of a pentose or by the oxygen at C4 of a tetrose.

In a preferred embodiment of the invention, the monosaccharide, the disaccharide or the trisaccharide CH consists of one, two or respectively 3 carbohydrates selected from the following group comprising or consisting of the following α- and β-D/L-carbohydrates:

α-D-ribopyranose, α-D-arabinopyranose, α-D-xylopyranose, α-D-lyxopyranose, α-D-allopyranose, α-D-altropyranose, α-D-glucopyranose, α-D-mannpyranose, α-D-glucopyranose, α-D-idopyranose, α-D-galactopyranose, α-D-talopyranose, α-D-psicopyranose, α-D-fructopyranose, α-D-sorbopyranose, α-D-tagatopyranose, α-D-ribofuranose, α-D-arabinofuranose, α-D-xylofuranose, α-D-lyxofuranose, α-D-Allofuranose, α-D-Altrofuranose, α-D-Glucofuranose, α-D-Mannofuranose, α-D-gulofuranose, α-D-idofuranose, α-D-galactofuranose, α-D-talofuranose, α-D-psicofuranose, α-D-fructofuranose, α-D-sorbofuranose, α-D-tagatofuranose, α-D-xylulofuranose, α-D-ribulofuranose, α-D-threofuranose, α-D-erythrofuranose, α-D-glucosamine, α-D-glucopyranuronic acid, α-D-rhamnopyranose, β-D-ribopyranose, β-D-arabinopyranose, β-D-xylopyranose, β-D-lyxopyranose, β-D-allopyranose, β-D-altropyranose, β-D-glucopyranose, β-D-mannpyranose, β-D-glucopyranose, β-D-idopyranose, β-D-galactopyranose, β-D-talopyranose, β-D-psicopyranose, β-D-fructopyranose, β-D-sorbopyranose, β-D-tagatopyranose, β-D-ribofuranose, β-D-arabinofuranose, β-D-xylofuranose, β-D-lyxofuranose, β-D-allofuranose, β-D-altrofuranose, β-D-glucofuranose, β-D-mannofuranose, β-D-gulofuranose, β-D-idofuranose, β-D-galactofuranose, β-D-talofuranose, β-D-psicofuranose, β-D-fructofuranose, β-D-sorbofuranose, β-D-tagatofuranose, β-D-xylulofuranose, β-D-ribulofuranose, β-D-threofuranose, β-D-erythrofuranose, β-D-rhamnopyranose, β-D-glucosamine, β-D-glucopyranuronic acid, α-L-ribopyranose, α-L-arabinopyranose, α-L-xylopyranose, α-L-lyxopyranose, α-L-allopyranose, α-L-altropyranose, α-L-glucopyranose, α-L-mannpyranose, α-L-glucopyranose, α-L-idopyranose, α-L-galactopyranose, α-L-talopyranose, α-L-psicopyranose, α-L-fructopyranose, α-L-sorbopyranose, α-L-tagatopyranose, α-L-ribofuranose, α-L-arabinofuranose, α-L-xylofuranose, α-L-lyxofuranose, α-L-Allofuranose, α-L-Altrofuranose, α-L-Glucofuranose, α-L-Mannofuranose, α-L-gulofuranose, α-L-idofuranose, α-L-galactofuranose, α-L-talofuranose, α-L-psicofuranose, α-L-fructofuranose, α-L-sorbofuranose, α-L-tagatofuranose, α-L-xylulofuranose, α-L-ribulofuranose, α-L-rhamnopyranose α-L-threofuranose, α-L-erythrofuranose, α-L-glucosamine, α-L-glucopyranuronic acid, β-L-ribopyranose, β-L-arabinopyranose, β-L-xylopyranose, β-L-lyxopyranose, β-L-allopyranose, β-L-altropyranose, β-L-glucopyranose, β-L-mannpyranose, β-L-glucopyranose, β-L-idopyranose, β-L-galactopyranose, β-L-talopyranose, β-L-psicopyranose, β-L-fructopyranose, β-L-sorbopyranose, β-L-tagatopyranose, β-L-ribofuranose, β-L-arabinofuranose, β-L-xylofuranose, β-L-lyxofuranose, β-L-allofuranose, β-L-altrofuranose, β-L-glucofuranose, β-L-mannofuranose, β-L-gulofuranose, β-L-idofuranose, β-L-galactofuranose, β-L-talofuranose, β-L-psicofuranose, β-L-fructofuranose, β-L-sorbofuranose, β-L-tagatofuranose, β-L-xylulofuranose, β-L-ribulofuranose, β-L-threofuranose, β-L-erythrofuranose, β-L-glucosamine, β-L-glucopyranuronic acid, and β-L-rhamnopyranose.

In another preferred embodiment of the invention, the monosaccharide, the disaccharide or the trisaccharide CH consists of one, two or respectively 3 carbohydrates selected from the α- and β-D/L-carbohydrates as mentioned on pages 25-29 and as defined for the A-moiety.

The monosaccharide, the disaccharide or the trisaccharide CH according to the present invention may further be substituted at specific positions, preferably at hydroxyl groups not involved in the bonding to the moieties A and L, or at an amino group if present in the saccharide moiety. In a preferred embodiment of the present invention the monosaccharide, the disaccharide or the trisaccharide CH bear one of the following substituents, preferably instead of a hydrogen atom at a hydroxyl groups one of the following substituents:

—$CH_3$, —$C_2H_5$, —$C_3H_7$, -cyclo-$C_3H_5$, —$CH(CH_3)_2$, —$C(CH_3)_3$, —$C_4H_9$, -Ph, —$CH_2$-Ph, —$CH_2$—$OCH_3$, —$C_2H_4$—$OCH_3$, —$C_3H_6$—$OCH_3$, —$CH_2$—$OC_2H_5$, —$C_2H_4$—$OC_2H_5$, —$C_3H_6$—$OC_2H_5$, —$CH_2$—$OC_3H_7$, —$C_2H_4$—$OC_3H_7$, —$C_3H_6$—$OC_3H_7$, —$CH_2$—O-cyclo-$C_3H_5$, —$C_2H_4$—O-cyclo-$C_3H_5$, —$C_3H_6$—O-cyclo-$C_3H_5$, —$CH_2$—$OCH(CH_3)_2$, —$C_2H_4$—$OCH(CH_3)_2$, —$C_3H_6$—$OCH(CH_3)_2$, —$CH_2$—$OC(CH_3)_3$, —$C_2H_4$—$OC(CH_3)_3$, —$C_3H_6$—$OC(CH_3)_3$, —$CH_2$—$OC_4H_9$, —$C_2H_4$—$OC_4H_9$, —$C_3H_6$—$OC_4H_9$, —$CH_2$—OPh, —$C_2H_4$—OPh, —$C_3H_6$—OPh, —$CH_2$—$OCH_2$-Ph, —$C_2H_4$—$OCH_2$-Ph, —$C_3H_6$—$OCH_2$-Ph.

Preferred α- and β-D/L-carbohydrates for the moiety CH with indicated connectivity by the dotted lines are the following residues:

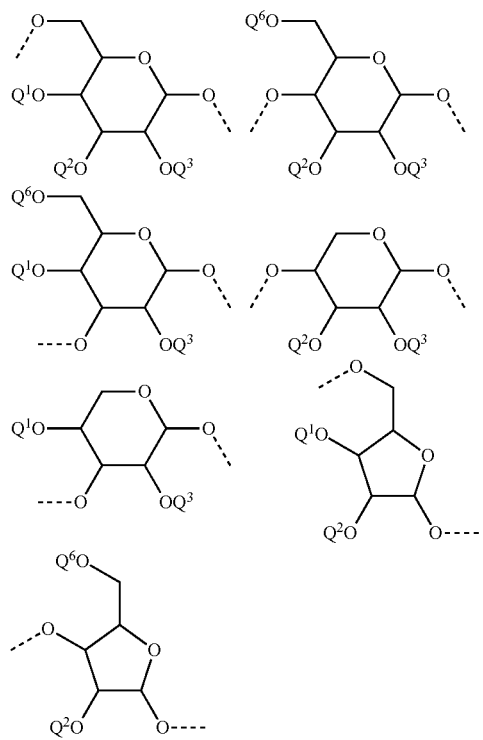

The substituents $Q^1$, $Q^2$, $Q^3$ and $Q^6$ have the meanings as defined herein.

In other preferred embodiments of the invention the CH moiety of the inventive carbohydrate-glycolipid conjugates has the following connectivity:

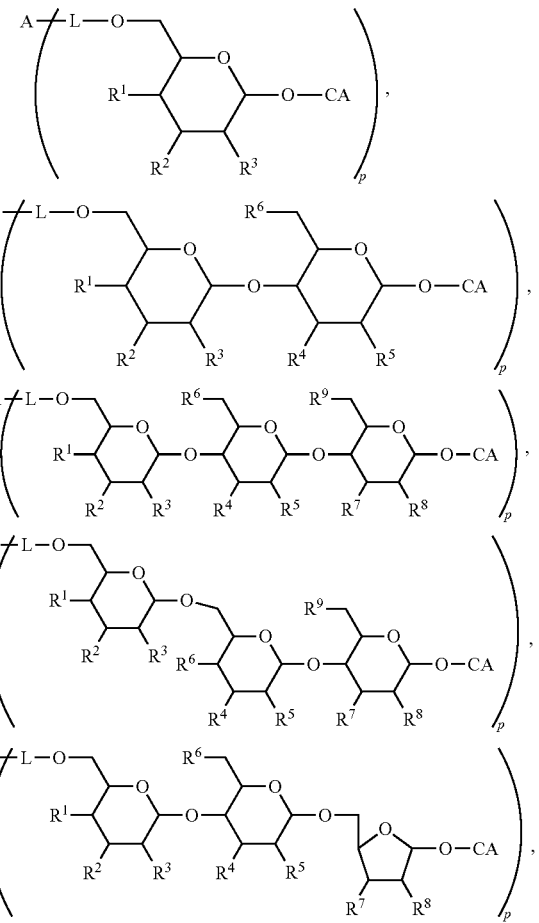

wherein the A, L, p and CA are defined as disclosed herein.

$R^1, R^2, R^3, R^4, R^5, R^6, R^7, R^8, R^9$ represent independently of each other:

—H, —OH, —$OCH_3$, —$OC_2H_5$, —$OC_3H_7$, —O—$SO_2$—$CH_3$, —O—$SO_2$—$C_2H_5$, —O—$SO_2$—$C_3H_7$, —O—$COOCH_3$, —$NHCOCH_3$, or —$NH_2$.

In more preferred embodiments of the invention the CH moiety of the inventive carbohydrate-glycolipid conjugates has the following connectivity as shown in the following preferred formula

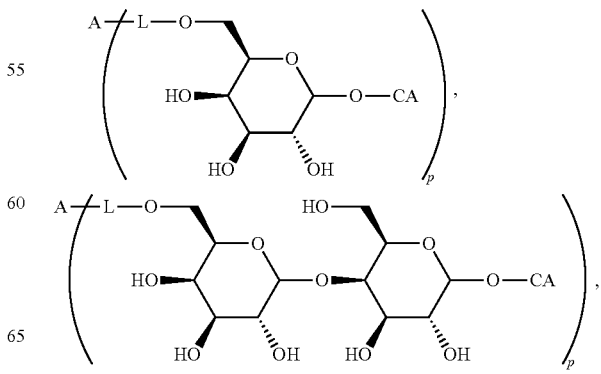

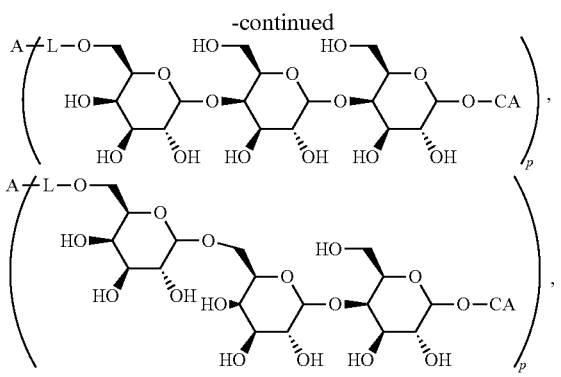

wherein the A, L, p and CA are defined as disclosed herein.

The glycosidic bonds within CH belong preferably to the group of glycosidic bonds wherein the hydroxyl function of the anomeric carbon is condensed with another hydroxyl function of another carbohydrate or of the CA moiety respectively. The glycosidic bond between two carbohydrates comprises the glycosidic bond between the anomeric carbon of one carbohydrate and the non-anomeric carbon of the other carbohydrate. Due to the stereochemistry of the anomeric carbon there is the possibility to form α or β-glycosidic bonds such as:

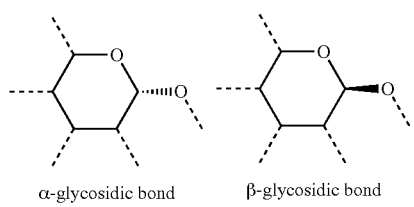

α-glycosidic bond     β-glycosidic bond

The Greek letters α and β are applicable only when the anomeric carbon atom has a lower locant than the anomeric reference atom. If this is not the case then the anomeric configuration is described by normal R/S-symbols.

The Ceramide Moiety CA

CA represents

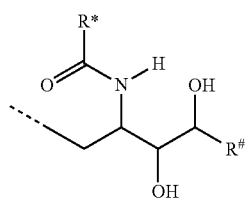

and more preferably

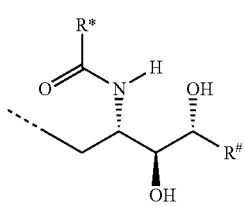

or
CA represents

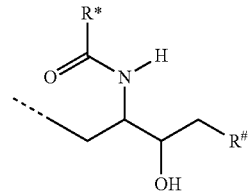

and more preferably

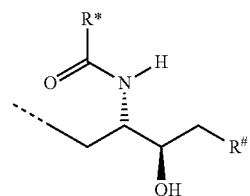

or
CA represents

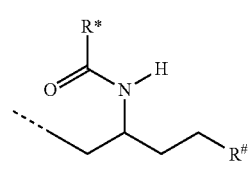

and more preferably

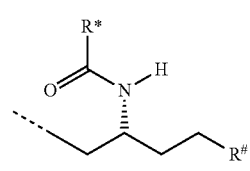

R* and R# represent independently of each other a linear or branched or cyclic, substituted or unsubstituted, saturated or unsaturated carbon residue consisting of 1 to 30 carbon atoms and up to 5 hetero atoms selected from N, O, S, F, Br and Cl.

Thus, R* and R# represent independently of each other a carbon residue of 1-30 carbon atoms, wherein the carbon residue may be a linear carbon chain or a branched carbon chain. The carbon residue may also contain carbocyclic structures or heterocyclic structures. The carbon residue may furthermore contain heteroatoms such as N, O, S and/or may have functional groups such as halogen like F, Cl and Br or functional groups containing the hetero atoms N, O, and/or S or functional groups such as double bonds and triple bonds.

The carbon residue or the carbon chain may contain one or more C═C double bonds and/or one or more C≡C triple bonds. The carbocyclic structures which might be present in the carbon residue or the carbon chain are, for instance, saturated 3-membered or 4-membered carbocyclic rings, saturated or unsaturated 5-membered carbocyclic rings or saturated, unsaturated or aromatic 6-membered carbocyclic rings which can be present as substituents on the carbon residue or carbon chain or can be incorporated into the carbon residue or carbon chain.

The heterocyclic structures which might be present in the carbon residue or the carbon chain are, for instance, saturated 3-membered or 4-membered heterocyclic rings containing one N or O atom, saturated or unsaturated 5-membered heterocyclic rings containing 1, 2, 3 or 4 N atoms or 1 or 2 S or O atoms or 1 O or S atom together with 1 or 2 N atoms or saturated, unsaturated or aromatic 6-membered heterocyclic rings containing 1, 2, 3 or 4 N atoms or 1 or 2 S or O atoms or 1 O or S atom together with 1 or 2 N atoms which can be present as substituents on the carbon residue or carbon chain or can be incorporated into the carbon residue or carbon chain.

The term "carbon residue of 1 to 30 carbon atoms" refers to one carbon atom or a chain of 2 to 30 carbon atoms which can be straight aligned (linear) by a suitable chemical bond or arranged in such an order that from 1 carbon atom two or three individual carbon atoms are bound (branched), and optionally proceed in different directions from the branching carbon atom. Further, the arrangement of the carbon atoms may also form a ring shape (cyclic). Also, any of the above mentioned arrangements of carbon atoms forming a carbon residue may include one or more double or triple bonds (unsaturated). In case the chain of carbon atoms does not include any double or triple bond the carbon residue is considered saturated. Optionally the "carbon residue of 1 to 30 carbon atoms" can be further substituted with 1 to 5 of the substituents $Z^1$, $Z^2$, $Z^3$, $Z^4$, $Z^5$. However it is clear to a skilled person that the term "can be substituted" refers to the replacement of a hydrogen atom by one of the substituents $Z^1$, $Z^2$, $Z^3$, $Z^4$, $Z^5$ each. In case the carbon residue of 1 to 30 carbon atoms does not contain any of the additional substituents $Z^1$, $Z^2$, $Z^3$, $Z^4$, $Z^5$ the residue is considered as unsubstituted.

More preferably R* and R# represent independently of each other linear or branched $C_1$-$C_{30}$-alkyl residue, a linear or branched $C_2$-$C_{30}$-alkenyl residue, a linear or branched $C_2$-$C_{30}$-alkynyl residue, a $C_3$-$C_{10}$-carbocycloalkyl residue, a $C_4$-$C_{30}$-alkylcycloalkyl, a $C_4$-$C_{30}$-alkylheterocycloalkyl residue, or a substituted $C_1$-$C_{30}$-carbon residue containing 1 to 5 of the substituents $Z^1$, $Z^2$, $Z^3$, $Z^4$, $Z^5$.

The substituents $Z^1$, $Z^2$, $Z^3$, $Z^4$, and $Z^5$ represent independently of each other —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —CH$_2$—OCH$_3$, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_6$—OPh, —CH$_2$—OCH$_2$-Ph, —C$_2$H$_4$—OCH$_2$-Ph, —C$_3$H$_6$—OCH$_2$-Ph, —NO$_2$, —F, —Cl, —Br, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —OCF$_3$, —CH$_2$—OCF$_3$, —C$_2$H$_4$—OCF$_3$, —C$_3$H$_6$—OCF$_3$, —OC$_2$F$_5$, —CH$_2$—OC$_2$F$_5$, —C$_2$H$_4$—OC$_2$F$_5$, —C$_3$H$_6$—OC$_2$F$_5$, —CH$_2$F, —CHF$_2$, —CF$_3$, —CH$_2$Cl, —CH$_2$Br, —CH$_2$—CH$_2$F, —CH$_2$—CHF$_2$, —CH$_2$—CF$_3$, —CH$_2$—CH$_2$Cl, —CH$_2$—CH$_2$Br.

The term "linear or branched $C_1$-$C_{30}$-alkyl residue" refers to a residue which is linked through a carbon atom and which consists in total of 1 to 30 carbon atoms including the carbon atoms of the branches. The same definition applies accordingly to the terms "linear $C_{20}$-$C_{30}$-alkyl residue", "linear $C_1$-$C_{10}$-alkyl residue" and "linear $C_{10}$-$C_{19}$-alkyl residue", The term "linear or branched $C_2$-$C_{30}$-alkenyl residue" refers to a residue which is linked through a carbon atom and which consists in total of 2 to 30 carbon atoms including the carbon atoms of the branches and which has at least one but not more than 15 double bonds. If branched, the longest carbon chain is the main chain while the side chains are the branches. The 1 to 15 C=C double bonds may be present in the main chain and/or the side chain(s).

The term "linear or branched $C_2$-$C_{30}$-alkynyl residue" refers to a residue which is linked through a carbon atom and which consists in total of 2 to 30 carbon atoms including the carbon atoms of the branches and which has at least one but not more than 15 triple bonds and preferably 1, 2 or 3 triple bonds. If branched, the longest carbon chain is the main chain while the side chains are the branches. The 1 to 15 C≡C triple bonds may be present in the main chain and/or the side chain(s).

The term "$C_3$-$C_{10}$-carbocycloalkyl residue" refers to a residue which is linked through a ring carbon atom and contains at least one carbocyclic ring and which consists in total of 3 to 10 carbon atoms including the carbon atoms of any alkyl, alkenyl or alkinyl substituent. The carbocyclic ring in the $C_3$-$C_{10}$-carbocycloalkyl residue can be saturated, partly unsaturated or fully unsaturated and might be aromatic. If the carbocyclic ring is part of a bicyclic ring or is connected to another ring, both carbocyclic rings may be saturated or unsaturated and might be aromatic or one ring is saturated and the second ring is partly or fully unsaturated.

Examples for preferred $C_3$-$C_{10}$-carbocycloalkyl residues to which it is also referred to as substituents $M^1$ are as follows:

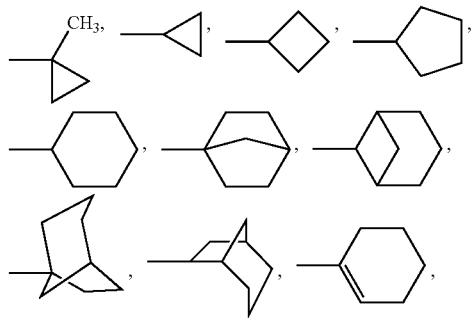

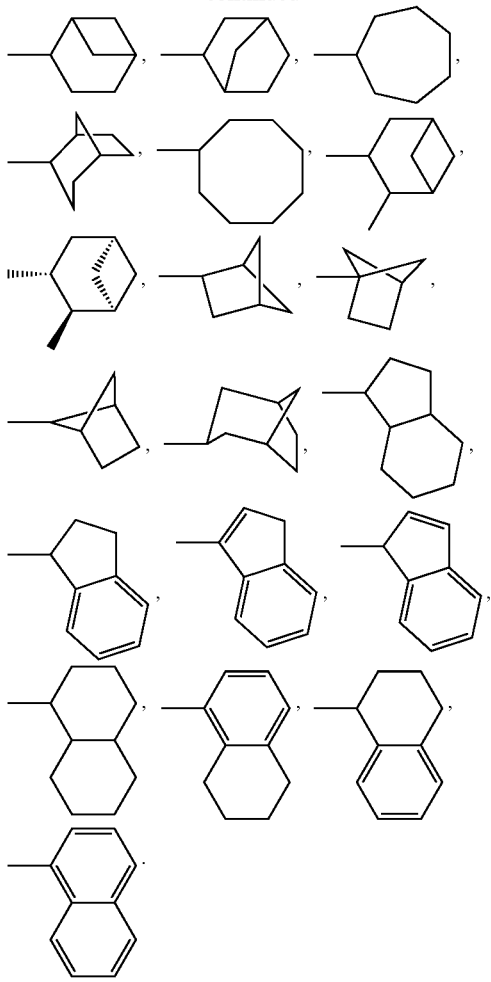

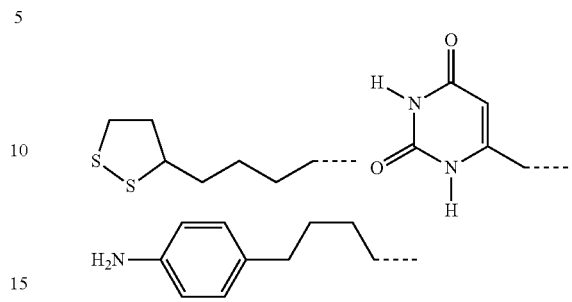

2 O atoms, 1 or 2 S atoms, 1, 2, 3, or 4 N atoms, 1 O and 1 or 2 N atoms or 1 S and 1 or 2 N atoms. Examples for such 0$C_4$-$C_{30}$-alkylheterocycloalkyl residues are:

The term "substituted $C_1$-$C_{30}$-carbon residue containing 1 to 5 of the substituents $Z^1$, $Z^2$, $Z^3$, $Z^4$, $Z^5$" refers to a residue which is linked through a carbon atom and which consists in total of 1 to 30 carbon atoms including the carbon atoms of any substituent such as alkyl, alkenyl, alkinyl, $Z^1$, $Z^2$, $Z^3$, $Z^4$, and/or $Z^5$ substituent. The residue bears 1 to 5 of the substituents $Z^1$, $Z^2$, $Z^3$, $Z^4$, $Z^5$ and can be linear or branched and saturated or unsaturated. Thus in addition to the at least one substituent $Z^1$, the residue may contain one or more C=C double bonds and/or one or more C≡C triple bonds. Moreover the substituted $C_1$-$C_{30}$-carbon residue may contain 1 to 10 hetero atoms N, O, S in the carbon chain or attached to the carbon chain. One or more oxygen atoms might be attached to the carbon chain thus forming one or more carbonyl groups. If branched, the longest chain is the main chain while the side chains are the branches. The carbonyl functionalities, the double bonds, the triple bonds as well as the substituents $Z^1$, $Z^2$, $Z^3$, $Z^4$, $Z^5$ can be present in or on the main chain and also in or on the side chain(s). Examples for such substituted $C_1$-$C_{30}$-carbon residue are:

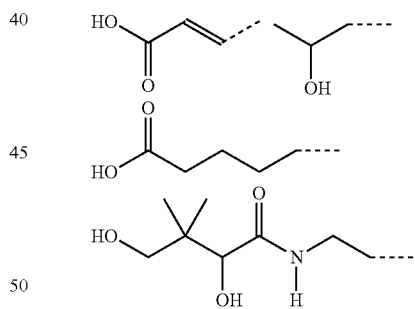

The term "$C_4$-$C_{30}$-alkylcycloalkyl" refers to a residue which is linked through a carbon atom not part of the carbocyclic ring and contains at least one carbocyclic ring and which consists in total of 4 to 30 carbon atoms including the carbon atoms of any alkyl, alkenyl or alkinyl substituent. The carbocyclic ring in the $C_4$-$C_{30}$-carbocycloalkyl residue can be saturated, partly unsaturated or fully unsaturated and might be aromatic. If the carbocyclic ring is part of a bicyclic ring or is connected to another ring, both carbocyclic rings may be saturated or unsaturated and might be aromatic or one ring is saturated and the second ring is partly or fully unsatured.

The term "$C_4$-$C_{30}$-alkylheterocycloalkyl residue" refers to a residue which is linked through a carbon atom not part of the heterocyclic ring and contains at least one heterocyclic ring and which consists in total of 4 to 30 carbon atoms including the carbon atoms of any alkyl, alkenyl or alkinyl substituent. The heterocyclic ring in the $C_4$-$C_{30}$-alkylheterocycloalkyl residue can be saturated, partly unsaturated or fully unsaturated and might be aromatic. 1 or 2 oxygen atoms can be attached to the heterocyclic ring thus forming one or two carbonyl groups. If the heterocyclic ring is part of a bicyclic ring or is connected to another ring which can be a carbocyclic or heterocyclic ring, both rings may be saturated or unsaturated and might be aromatic or one ring is saturated and the second ring is partly or fully unsatured and might be aromatic. The heterocyclic ring contains 1 or In a preferred embodiment of the invention the residues R* and R# represent independently of each other:
—$CH_3$, —$(CH_2)_r$—$CH_3$, —CH(OH)—$(CH_2)$—$CH_3$, —CH=CH—$CH_3$, —CH=CH—$(CH_2)_t$—$CH_3$, —CH(OH)—$(CH_2)_v$—CH$(CH_3)_2$, —CH(OH)—$(CH_2)_w$—CH$(CH_3)$—$CH_2$—$CH_3$, —$(CH_2)_a$—CH=CH—$(CH_2)_b$—$CH_3$, —$(CH_2)_c$—CH=CH—$(CH_2)_d$—CH=CH—$(CH_2)_e$—$CH_3$, —$(CH_2)_f$—CH=CH—$(CH_2)_g$—CH=CH—$(CH_2)_h$—CH=CH—$(CH_2)_i$—$CH_3$, —$(CH_2)_j$—CH=CH—$(CH_2)_k$—CH=CH—$(CH_2)_l$—CH=CH—$(CH_2)_o$—CH=CH$(CH_2)_q$$CH_3$, wherein a, b, c, d, e, f, g, h, i, j, k, l, o, q are integers from 1 to 26 with the proviso that: (a+b)≤27; (c+d+e)≤25; (f+g+h+i)≤23; (j+k+l+o+q)≤21; and wherein r is an integer from 1 to 29, s is an integer from 1 to 28, t is an integer from to 27, v is an integer from 1 to 26, and w is an integer from 1 to 25 and furthermore —(CH═CH—CH$_2$)$_q$—CH$_3$, —(CH$_2$—CH═CH)$_q$—CH$_3$, —(CH═CH)$_A$—CH$_3$, wherein q is an integer from 1 to 9, A is an integer from 1 to 14 and furthermore —(CH═CH—CH$_2$)$_B$—(CH$_2$)$_C$—CH$_3$, —(CH$_2$—CH═CH)$_B$—(CH$_2$)$_C$—CH$_3$, —(CH═CH)$_D$—(CH$_2$)$_E$—CH$_3$, —(CH$_2$)$_E$—(CH═CH)$_D$—CH$_3$, —(CH$_2$)$_F$—(CH═CH)$_G$—(CH$_2$)$_H$—CH$_3$, —(CH$_2$)$_J$—(CH═CH—CH$_2$)$_K$—(CH$_2$)$_N$—CH$_3$, —(CH$_2$)$_P$—(CH═CH)$_Q$—(CH$_2$)$_R$—(CH═CH)$_S$—(CH$_2$)$_T$—CH$_3$, —(CH$_2$)$_U$—(CH═CH—CH$_2$)$_V$—(CH$_2$)$_W$—(CH═CH—CH$_2$)$_X$—(CH$_2$)$_Y$—CH$_Z$, wherein B, C, D, E, F, G, H; I, J, K, L, M, N, P, Q, R, S, T, U, V, W, X, Y and Z represent independently from each other an integer between 1 and 26 with the proviso that the total number of carbon atoms of the afore-mentioned residues does not exceed 30.

In another preferred embodiment of the invention the residues R* and R# represent independently of each other:

ethyl, propyl, butyl, pentyl, hexyl, heptyl, octyl, nonyl, decyl, dodecyl, tetradecyl, cis-9-tetradecenyl, cis-9-hexadecenyl, cis-6-octadecenyl, cis-9-octadecenyl, cis-11-octadecenyl, cis-9-eicosenyl, cis-11-eicosenyl, cis-13-docosenyl, cis-15-tetracosenyl, trans-9-octadecenyl, trans-11-octadecenyl, trans-3-hexadecenyl, 9,12-octadecadienyl, 6,9,12-octadecatrienyl, 8,11,14-eicosatrienyl, 5,8,11,14-eicosatetraenyl, 7,10,13,16-docosatetraenyl, 4,7,10,13,16-docosapentaenyl, 9,12,15-octadecatrienyl, 6,9,12,15-octadecatetraenyl, 8,11,14,17-eicosatetraenyl, 5,8,11,14,17-eicosapentaenyl, 7,10,13,16,19-docosapentaenyl, 4,7,10,13,16,19-docosahexaenyl, 5,8,11-eicosatrienyl, 9c 11t 13t eleostearyl, 8t 10t 12c calendyl, 9c 11t 13c catalpyl, cis-9 tetradecenyl, cis-9-hexadecenyl, cis-6-octadecenyl, cis-9-octadecenyl, cis-11-octadecenyl, cis-9-eicosenyl, cis-11-eicosenyl, cis-13-docosenyl, cis-15-tetracosenyl, 9,12-octadecadienyl, 6,9,12-octadecatrienyl, 8,11,14-eicosatrienyl, 5,8,11,14-eicosatetraenyl, 7,10,13,16-docosatetraenyl, 4,7,10,13,16 docosapentaenyl, 9,12,15-octadecatrienyl, 6,9,12,15-octadecatetraenyl, 8,11,14,17-eicosatetraenyl, 5,8,11,14,17-eicosapentaenyl, 7,10,13,16,19-docosapentaenyl, 4,7,10,13,16,19-docosahexaenyl, 5,8,11-eicosatrienyl, 1,2-dithiolane-3-pentanyl, 6,8-dithiane octanyl, docosaheptadecanyl, eleostearyl, calendyl, catalpyl, taxoleyl, pinolenyl, sciadonyl, retinyl, 14-methyl pentadecanyl, pristanyl, phytanyl, 11,12-methyleneoctadecanyl, 9,10-methylenehexadecanyl, 9,10-epoxystearyl, 9,10-epoxyoctadec-12-enyl, 6-octadecynyl, t11-octadecen-9-ynyl, 9-octadecynyl, 6-octadecen-9-ynyl, t10-heptadecen-8-ynyl, 9-octadecen-12-ynyl, t7,t11-octadecadiene-9-ynyl, t8,t10-octadecadiene-12-ynyl, 5,8,11,14-eicosatetraynyl, 2-hydroxytetracosanyl, 2-hydroxy-15-tetracosenyl, 12-hydroxy-9-octadecenyl or 14-hydroxy-11-eicosenyl, 4,7,9,11,13,16,19-docosaheptadecanyl, 6-octadecynyl, t11-octadecen-9-ynyl, isopalmityl, 9,10-methylenhexadecyl, coronaryl, (R,S)-lipoyl, 6,8-bis(methylsulfanyl)-octanyl, 4,6-bis(methylsulfanyl)-hexanyl, 2,4-bis(methylsulfanyl)-butanyl, 1,2-dithiolanyl, cerebronyl, hydroxynervonyl, ricinyl, lesqueryl, brassylyl, thapsyl, dodecyl, hexadecyl, octadecyl, eicosanyl, docosanyl, tetracosanyl, cis-9-tetradecenyl, cis-9-hexadecenyl, cis-6-octadecenyl, cis-9-octadecenyl, cis-11-octadecenyl, cis-9-eicosenyl, cis-11-eicosenyl, cis-13-docosenyl, cis-15-tetracosenyl, 9,12-octadecadienyl, 6,9,12-octadecatrienyl, 8,11,14-eicosatrienyl, 5,8,11,14-eicosatetraenyl, 7,10,13,16-docosatetraenyl, 4,7,10,13,16-docosapentaenyl, 9,12,15-octadecatrienyl, 6,9,12,15-octadecatetraenyl, 8,11,14,17-eicosatetraenyl, 5,8,11,14,17-eicosapentaenyl, 7,10,13,16,19-docosapentaenyl, 4,7,10,13,16,19-docosahexaenyl, 5,8,11-eicosatrienyl, 1,2-dithiolane-3-pentanyl, 6,8-dithiane octanyl, docosaheptadecanyl, eleostearyl, calendyl, catalpyl, taxoleyl, pinolenyl, sciadonyl, retinyl, 14-methyl pentadecanyl, pristanyl, phytanyl, 11,12-methyleneoctadecanyl, 9,10-methylenehexadecanyl, 9,10-epoxystearyl, 9,10-epoxyoctadec-12-enyl, 6-octadecynyl, t11-octadecen-9-ynyl, 9-octadecynyl, 6-octadecen-9-ynyl, t10-heptadecen-8-ynyl, 9-octadecen-12-ynyl, t7,t11-octadecadiene-9-ynyl, t8,t10-octadecadiene-12-ynyl, 5,8,11,14-eicosatetraynyl, 2-hydroxytetracosanyl, 2-hydroxy-15-tetracosenyl, 12-hydroxy-9-octadecenyl, and 14-hydroxy-11-eicosenyl.

In another preferred embodiment of the invention the residues R* and R# are independently of each other substituted with a phenyl ring, preferably an unsubstituted phenyl ring. Further, it is preferred that said phenyl ring is positioned at the residues R* and R# at the opposite end where the residues R* and R# are bond to the rest of the moiety CA.

Also, in a preferred embodiment of the present invention the residues R* and R# are the same, preferably a linear alkyl residue, and more preferably a linear $C_{10}$-$C_{30}$-alkyl residue, and most preferably a linear —$C_{14}H_{29}$.

In another preferred embodiment of the present invention the residues R* and R# are different from each other and represent different linear alkyl residues, preferably the residue R* represents a linear $C_{20}$-$C_{30}$-alkyl residue and the residue R# represents a linear $C_{10}$-$C_{19}$-alkyl residue, and more preferably R* represents a linear —$C_{25}H_{51}$ residue and the residue R# represents a linear —$C_{14}H_{29}$ residue.

In another preferred embodiment of the present invention the residues R* and R# are different from each other and represent different linear alkyl residues, preferably the residue R* represents a linear $C_1$-$C_{10}$-alkyl residue and the residue R# represents a linear $C_{10}$-$C_{19}$-alkyl residue, and more preferably R* represents a linear —$C_4H_9$ residue and the residue R# represents a linear —$C_{14}H_{29}$ residue.

Yet, in another preferred embodiment of the present invention the residues R* and R# are different from each other and represent different linear alkyl residues, wherein the residues R* is further substituted with a phenyl ring, preferably the residue R* represents a phenyl-substituted linear $C_1$-$C_{10}$-alkyl residue and the residue R# represents a linear $C_{10}$-$C_{19}$-alkyl residue, and more preferably R* represents a linear —$C_6H_{12}$-Ph residue and the residue R# represents a linear —$C_{14}H_{29}$ residue. In another preferred embodiment of the present invention the residues R* and R# are different from each other and represent different linear alkyl residues, preferably the residue R* represents a linear $C_{20}$-$C_{30}$-alkyl residue and the residue R# represents a linear $C_1$-$C_{10}$-alkyl residue, and more preferably R* represents a linear —$C_{25}H_{51}$ residue and the residue R# represents a linear —$C_5H_{11}$ residue.

The following formulas (II, III, IV and V) of the general formula (I) are preferred:

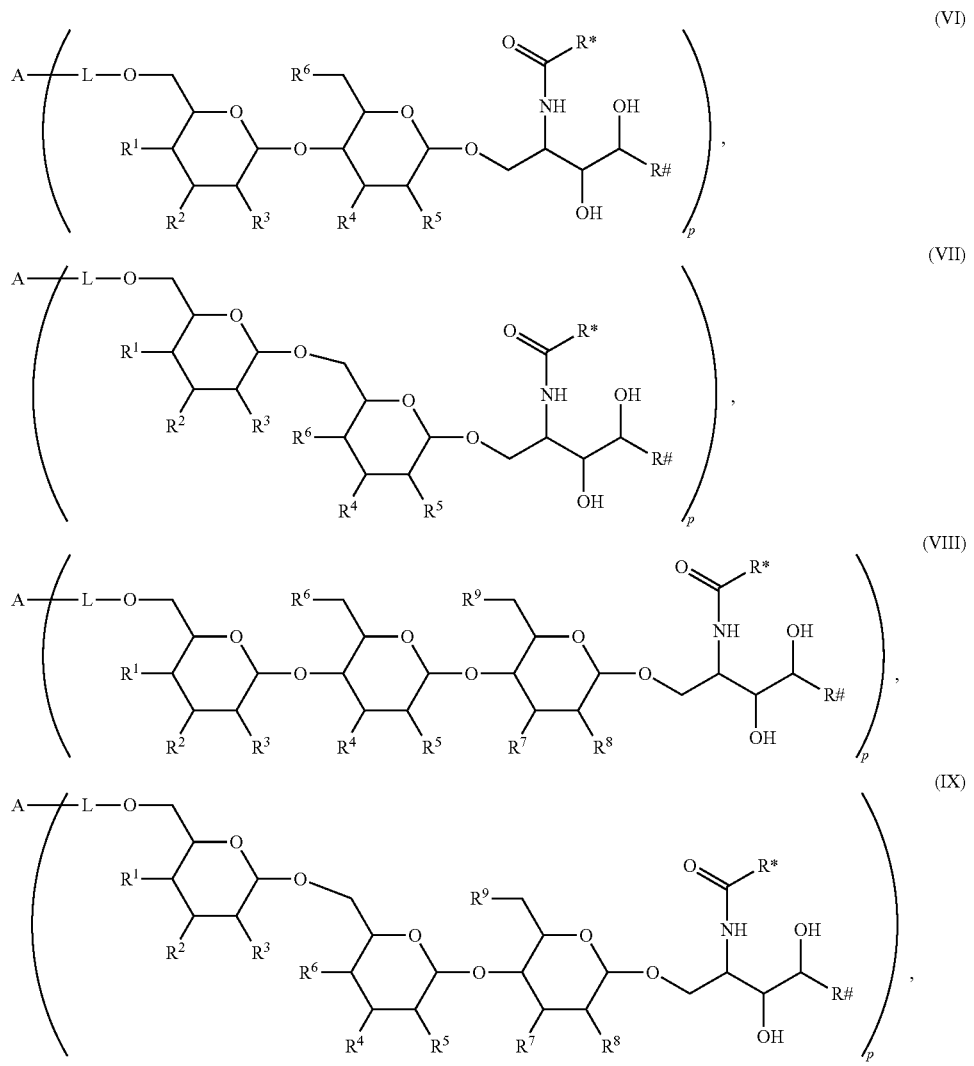

wherein
A, L, R*, R# and p have the meanings as defined herein.
$R^1$, $R^2$, $R^3$ represent independently of each other: —H, —OH, —OCH$_3$, —OC$_2$H$_5$, —OC$_3$H$_7$, —O—SO$_2$—CH$_3$, —O—SO$_2$—C$_2$H$_5$, —O—SO$_2$—C$_3$H$_7$, —O—COOCH$_3$, —NHCOCH$_3$, —NH$_2$, Furthermore, the following formulas (VI, VII, VIII, IX) of the general formula (I) are preferred:

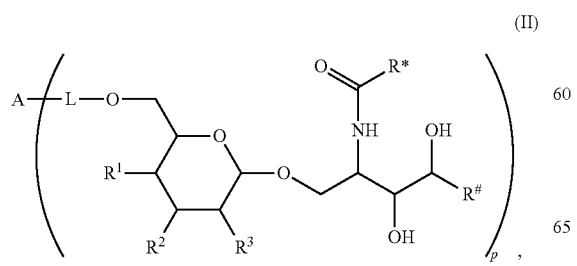

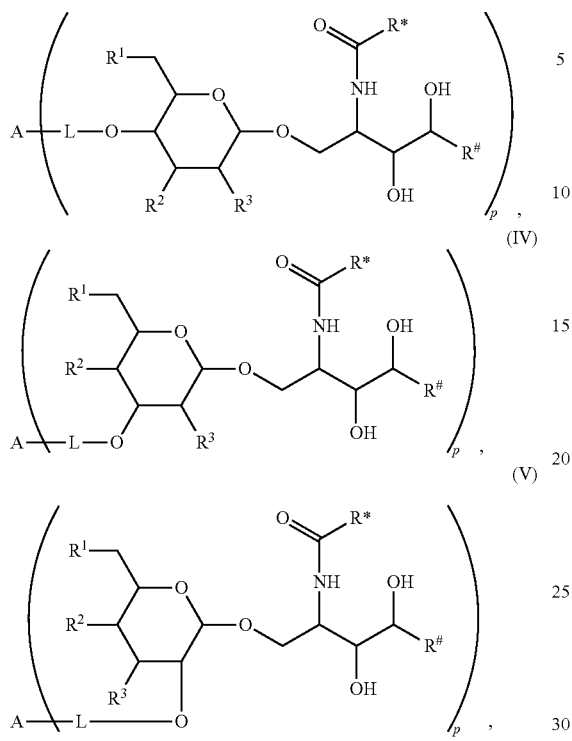

(III)

(IV)

(V)

wherein
A, L, R*, R# and p have the meanings as defined herein.
R¹, R², R³, R⁴, R⁵, R⁶, R⁷, R⁸, R⁹ represent independently of each other: —H, —OH, —OCH₃, —OC₂H₅, —OC₃H₇, —O—SO₂—CH₃, —O—SO₂—C₂H₅, —O—SO₂—C₃H₇, —O—COOCH₃, —NHCOCH₃, —NH₂, In a specifically preferred embodiment of the present invention the following subformulas (IIb, IIIb, IVb and Vb) of the general formula (I) are preferred:

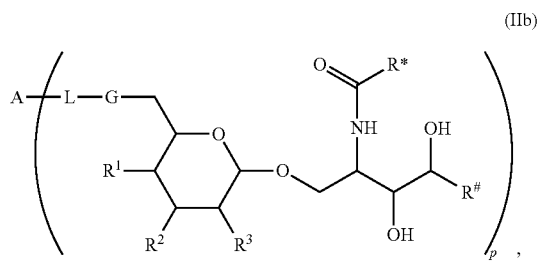

(IIb)

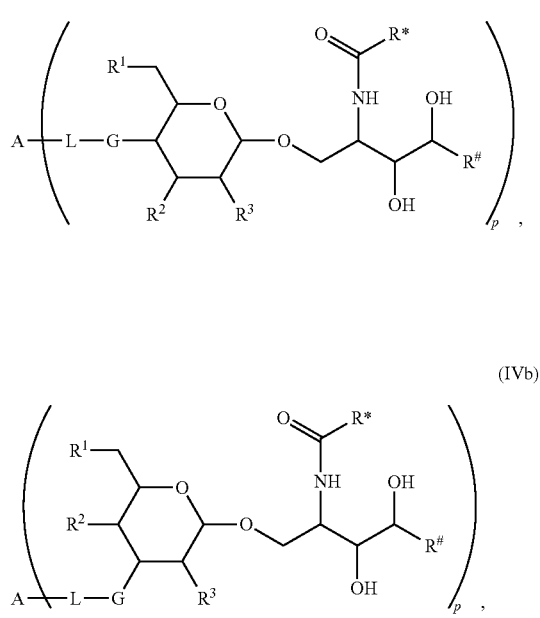

(IIIb)

(IVb)

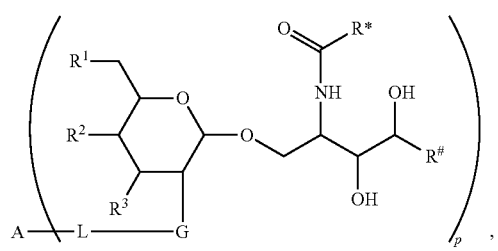

(Vb)

wherein
A, L, R*, R# and p have the meanings as defined herein.
R¹, R², R³ represent independently of each other: —H, —OH, —OCH₃, —OC₂H₅, —OC₃H₇, —O—SO₂—CH₃, —O—SO₂—C₂H₅, —O—SO₂—C₃H₇, —O—COOCH₃, —NHCOCH₃, —NH₂,
G represents —NH—, —O—, —S—, Furthermore, the following subformulas (VIb, VIIb, VIIIb, IXb) of the general formula (I) are preferred:

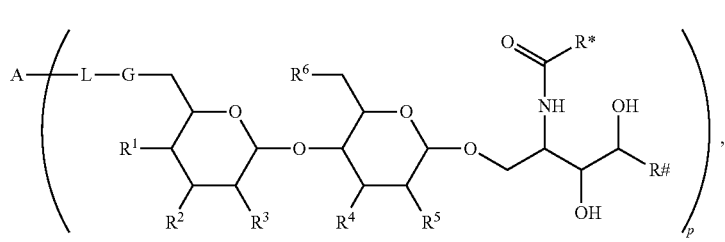

(VIb)

-continued
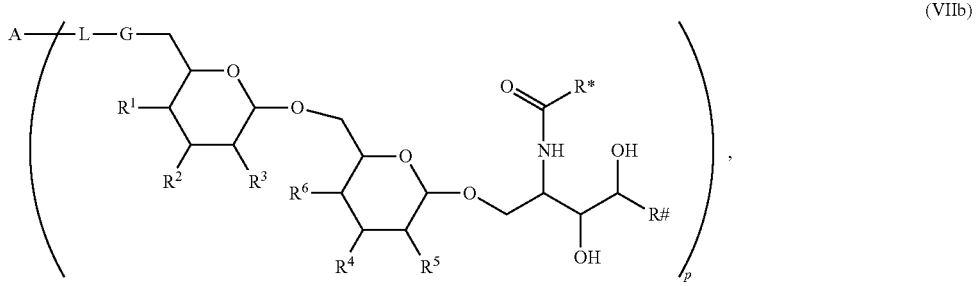
(VIIb)
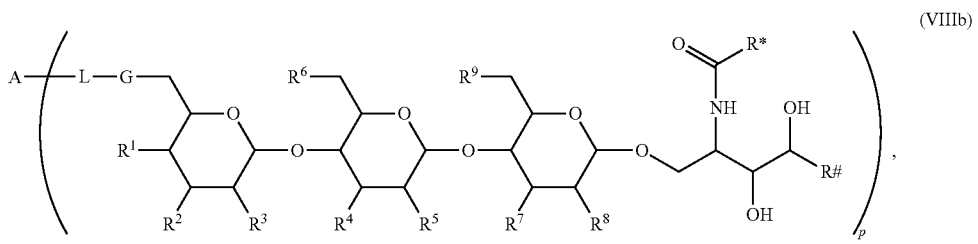
(VIIIb)
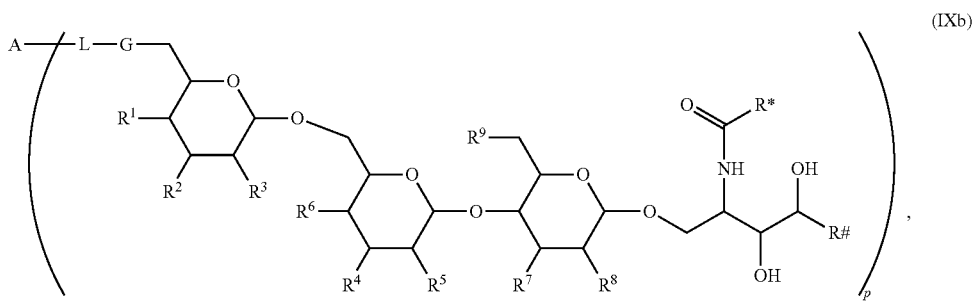
(IXb)
wherein
A, L, R*, R# and p have the meanings as defined herein.
$R^1, R^2, R^3, R^4, R^5, R^6, R^7, R^8, R^9$ represent independently of each other: —H, —OH, —OCH$_3$, —OC$_2$H$_5$, —OC$_3$H$_7$, —O—SO$_2$—CH$_3$, —O—SO$_2$—C$_2$H$_5$, —O—SO$_2$—C$_3$H$_7$, —O—COOCH$_3$, —NHCOCH$_3$, —NH$_2$,
G represents —NH—, —O—, —S—,
Furthermore the following substructures (X, XI, XII, XIII) of the general structure (I) are preferred:
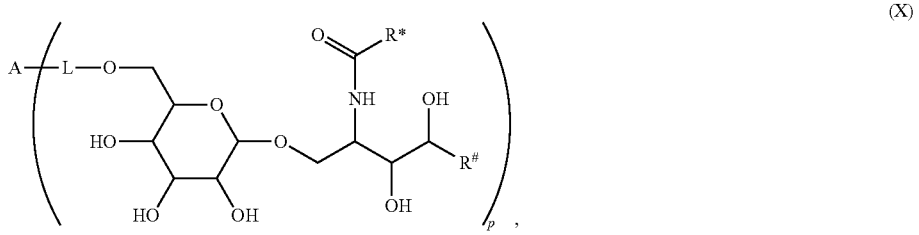
(X)
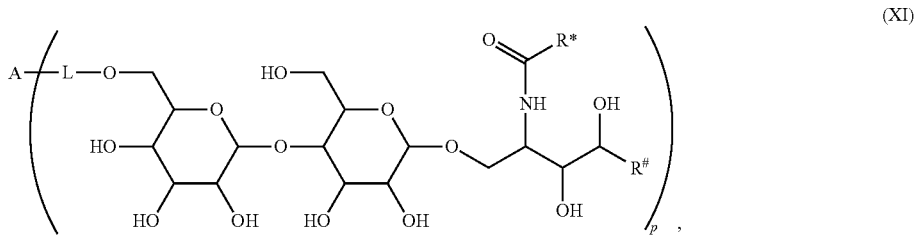
(XI)

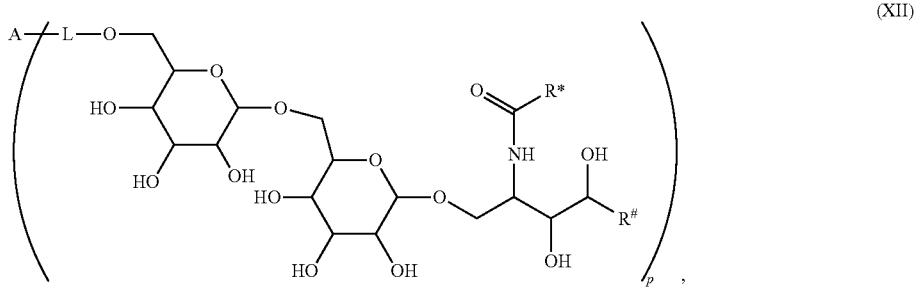
(XII)
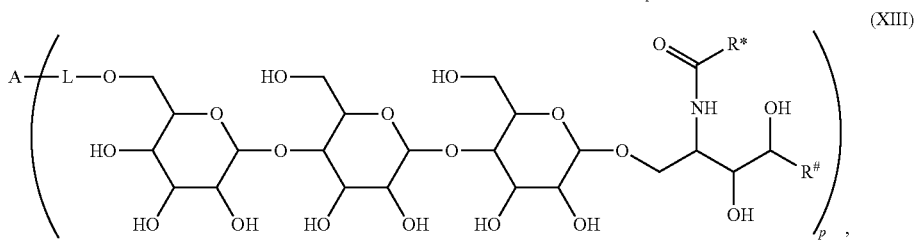
(XIII)
wherein
A, L, R*, R# and p have the meanings as defined herein.
Furthermore the following substructures (XIV, XV, XVI, XVII) of the general structure (I) are preferred:
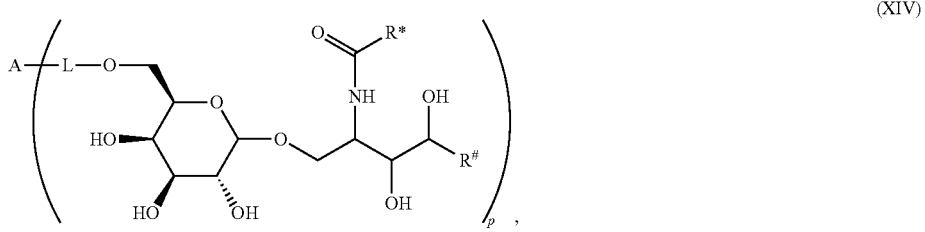
(XIV)
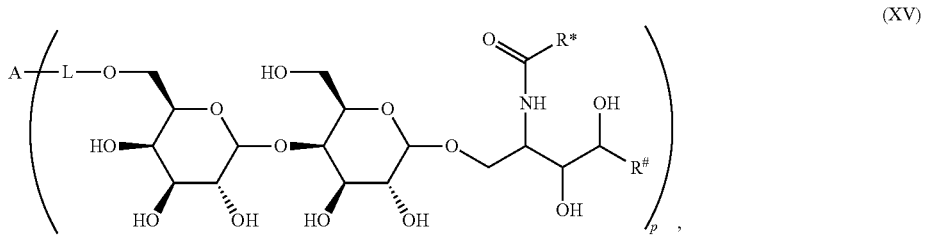
(XV)
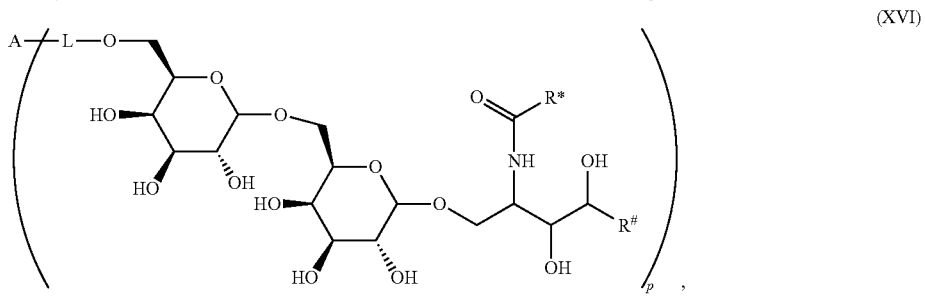
(XVI)
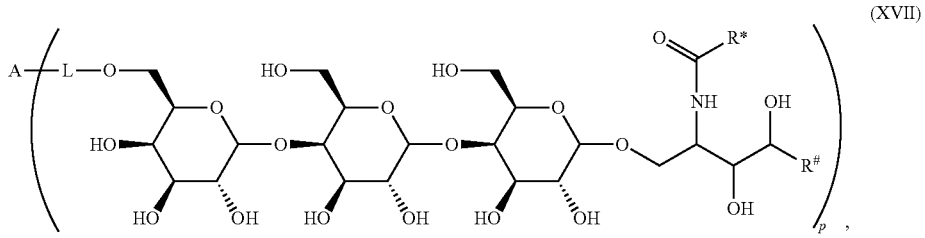
(XVII)

wherein
A, L, R*, R# and p have the meanings as defined herein.
Furthermore the following substructures (XVIII, XIX, XX) of the general structure (I) are preferred:

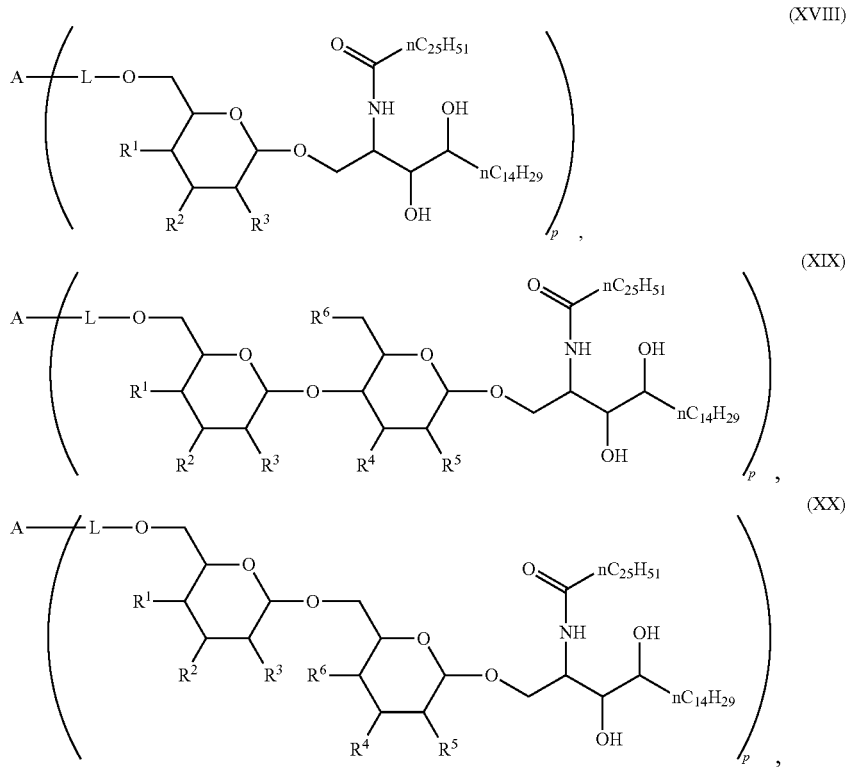

wherein
A, L and p have the meanings as defined herein.
$R^1, R^2, R^3, R^4, R^5, R^6, R^7, R^8, R^9$ represent independently of each other: —H, —OH, —OCH$_3$, —OC$_2$H$_5$, —OC$_3$H$_7$, —O—SO$_2$—CH$_3$, —O—SO$_2$—C$_2$H$_5$, —O—SO$_2$—C$_3$H$_7$, —O—COOCH$_3$, —NHCOCH$_3$, —NH$_2$, In a specifically preferred embodiment of the present invention the following substructures (XVIIIb, XIXb, XXb) of the general structure (I) are preferred:

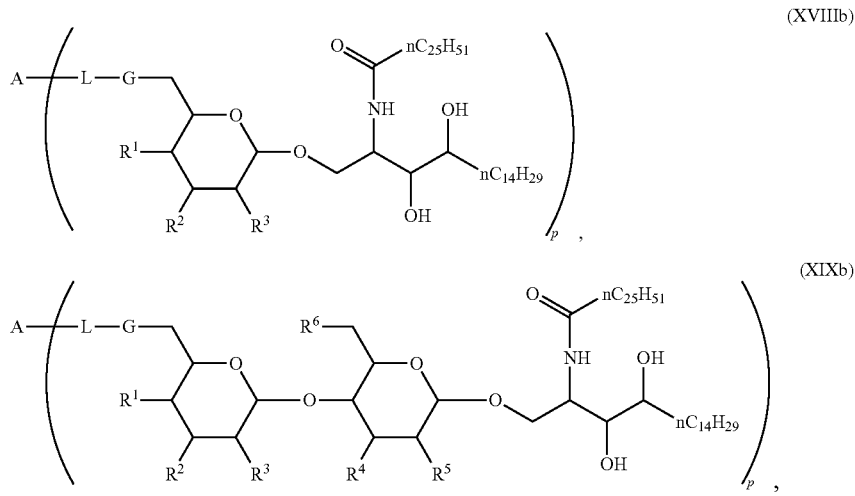

-continued

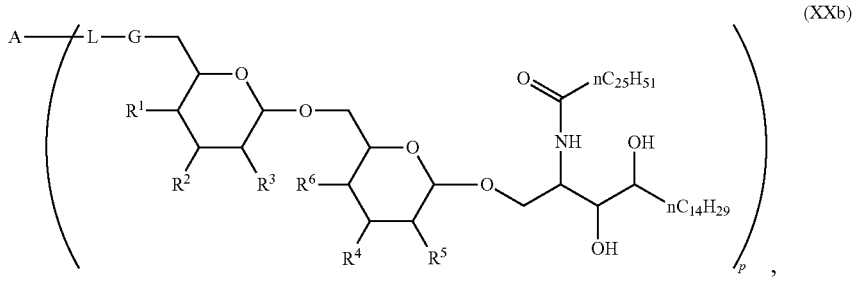

(XXb)

wherein
A, L and p have the meanings as defined herein.
$R^1, R^2, R^3, R^4, R^5, R^6, R^7, R^8, R^9$ represent independently of each other: —H, —OH, —OCH$_3$, —OC$_2$H$_5$, —OC$_3$H$_7$, —O—SO$_2$—CH$_3$, —O—SO$_2$—C$_2$H$_5$, —O—SO$_2$—C$_3$H$_7$, —O—COOCH$_3$, —NHCOCH$_3$, —NH$_2$, G represents —NH—, —O—, —S—, Furthermore the following substructures (XXI, XXII, XXIII, XXIV) of the general structure (I) are preferred:

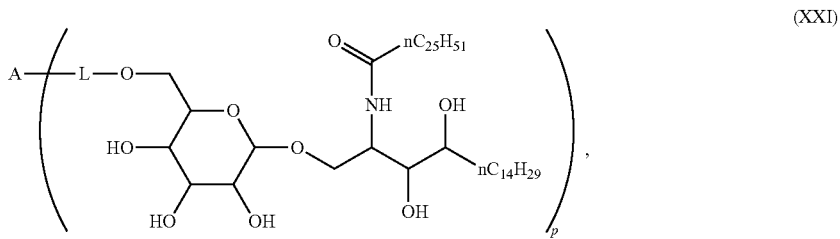

(XXI)

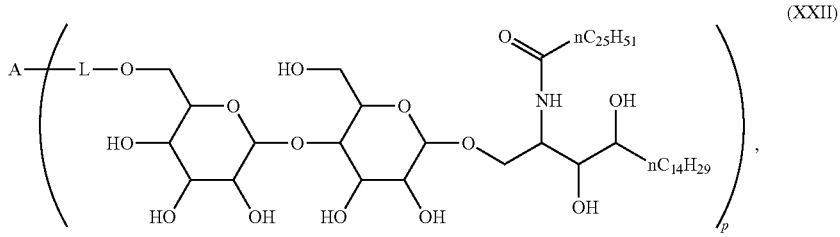

(XXII)

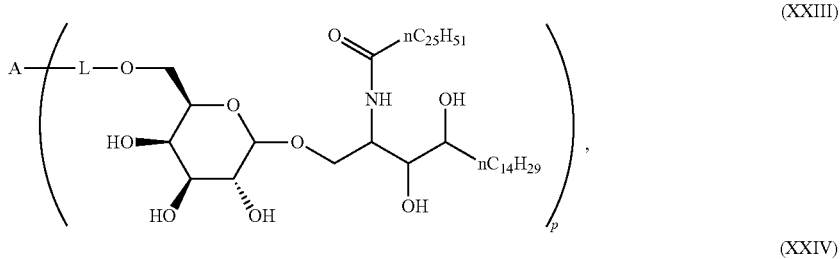

(XXIII)

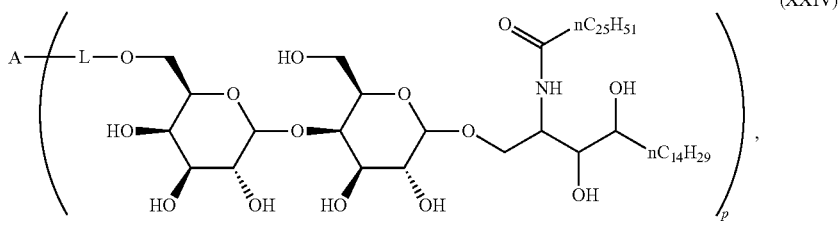

(XXIV)

wherein
A, L and p have the meanings as defined herein.

Especially preferred are compounds of the subformulas (XXV), (XXVI) and (XXVII) of the general formula (I):

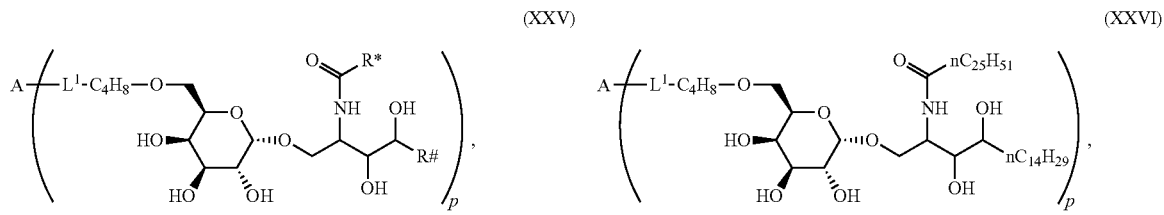
(XXV)     (XXVI)

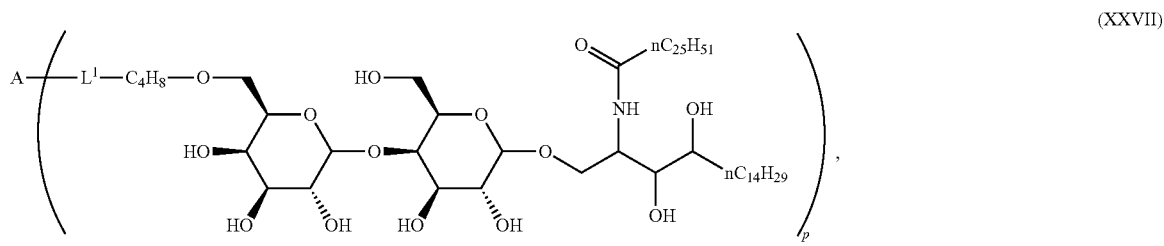
(XXVII)

wherein
A, $L^1$ and p have the meanings as defined herein.

Yet in another preferred embodiment of the present invention the compounds of the present invention refer to the following subformulas The following subformulas (IIc, IIIc, IVc and Vc) of the general formula (I) are preferred:

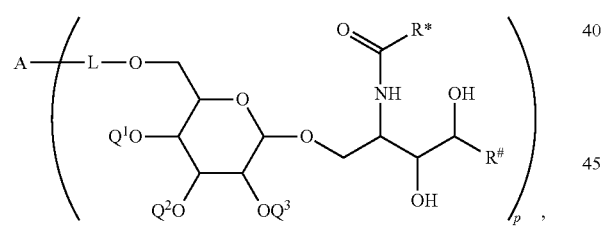
(IIc)

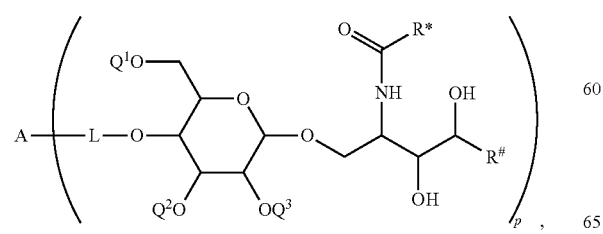
(IIIc)

-continued

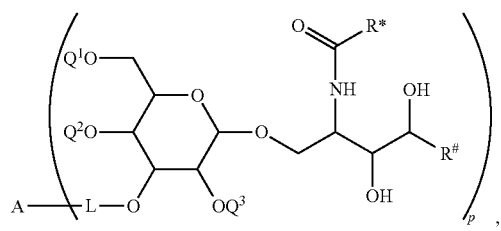
(IVc)

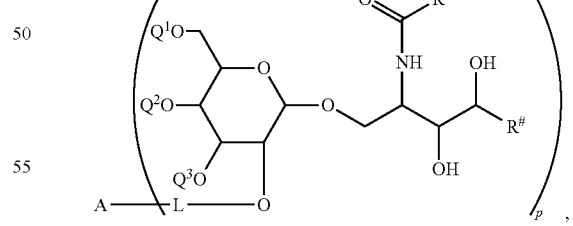
(Vc)

wherein
A, L, R*, R# and p have the meanings as defined herein.
$Q^1$, $Q^2$, $Q^3$ represent independently of each other: —H, —$CH_3$, —$C_2H_5$, —$C_3H_7$, —$SO_2$—$CH_3$, —$SO_2$—$C_2H_5$, —$SO_2$—$C_3H_7$, —$COCH_3$, Furthermore, the following subformulas (VI, VII, VIII, IX) of the general formula (I) are preferred:

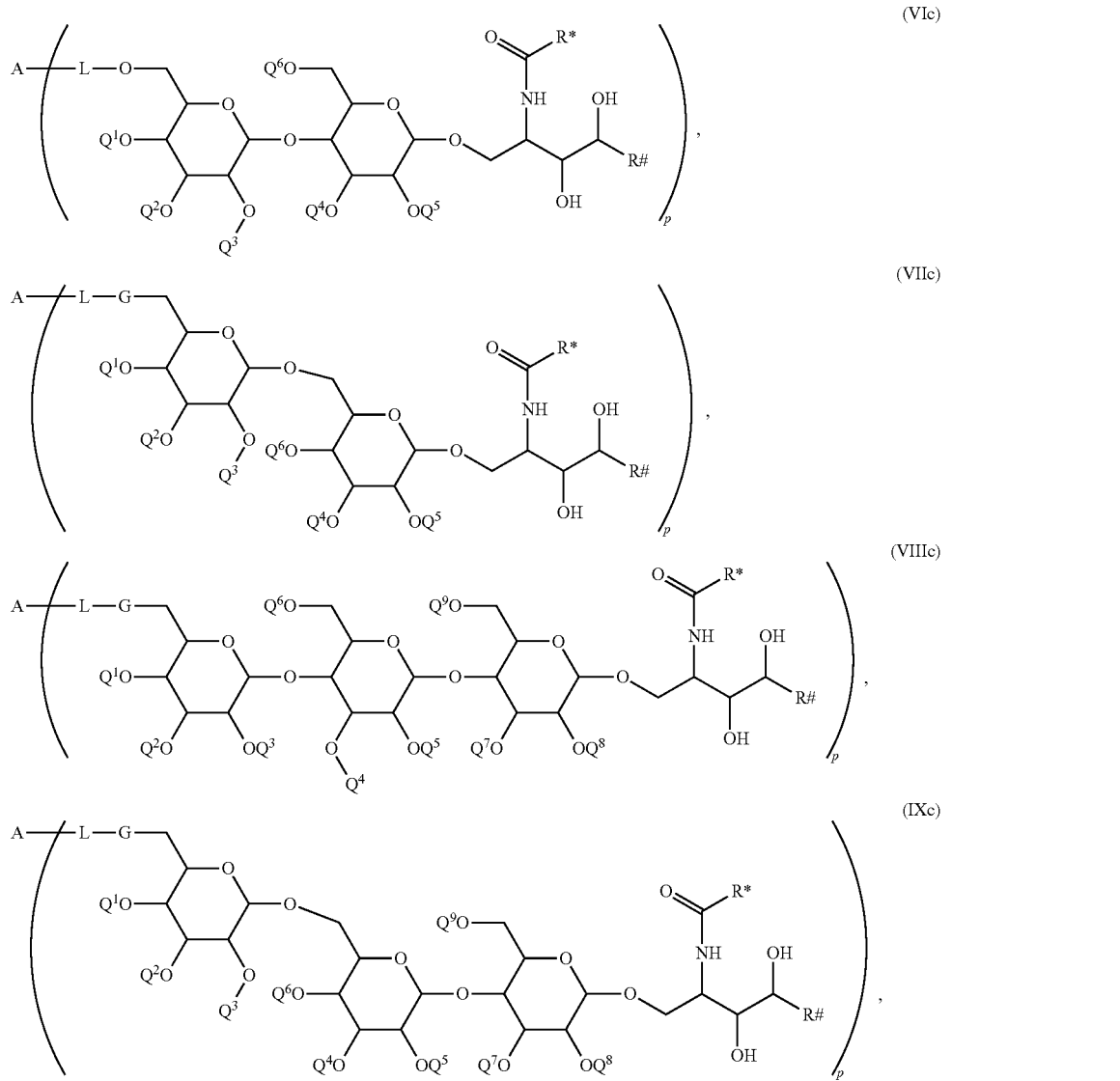

wherein

A, L, R*, R# and p have the meanings as defined herein.

$Q^1$, $Q^2$, $Q^3$, $Q^4$, $Q^5$, $Q^6$, $Q^7$, $Q^8$, $Q^9$ represent independently of each other: —H, —CH$_3$, —C$_2$H$_5$, —C$_3$H$_7$, —SO$_2$—CH$_3$, —SO$_2$—C$_2$H$_5$, —SO$_2$—C$_3$H$_7$, —COCH$_3$, All embodiments of this invention comprise the enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts thereof.

The expression prodrug is defined as a pharmacological substance, a drug, which is administered in an inactive or significantly less active form. Once administered, the prodrug is metabolized in the body in vivo into the active compound.

The expression tautomer is defined as an organic compound that is interconvertible by a chemical reaction called tautomerization. Tautomerization can be catalyzed preferably by bases or acids or other suitable compounds.

The extraction and isolation of carbohydrate antigens from a pathogen may be accomplished by a variety of means (MICROBIOLOGICAL REVIEWS, Vo. 42, Nr. 1, 84-113, 1978; JOURNAL OF IMMUNOLOGICAL METHODS Vo. 44, Nr. 3, 249-270, 1981). One common method is described as follows:

The isolation and purification usually involve alkaline extraction of cell walls or cells that first had been delipidated with organic solvents, followed by precipitation with organic solvents. Further purification is achieved with ion-exchange chromatography.

Proteolytic enzymes are used to remove remaining peptide or protein components followed by affinity chromatography as a final purification step.

The synthesis of synthetic carbohydrate antigens may be accomplished by a variety of means (Nature Reviews Drug Discovery 4, 751-763, September 2005). The automated solid-phase method is described as follows:

Automated solid-phase oligosaccharide synthesis has been developed from insights gained from oligopeptide and oligonucleotide assembly. The first building block is added to a polystyrene resin equipped with an easily cleavable linker containing a free hydroxyl group. An activating agent induces couplings involving glycosyl phosphate and glycosyl trichloroacetimidate building blocks. Unlike oligonucleotide and peptide couplings, glycosidic bond formation occurs mostly at low temperatures and requires a reaction chamber that can be cooled. Excess building blocks (that is, a 5-10-fold molar excess, sometimes applied twice) are added to the chamber for each coupling.

Washing and filtration remove any side products or remaining reagents before selective removal of a temporary protective group readies the next hydroxyl group for subsequent coupling. Coupling efficiencies can be assessed by spectrometric read-out after protecting-group removal when temporary protecting groups that absorb ultraviolet radiation, such as 9-fluorenylmethyloxycarbonyl (Fmoc), are used. Originally, this coupling-deprotection cycle was automated using a converted peptide synthesizer.

After completion of the oligosaccharide sequence, the fully protected product is cleaved from solid support. After global deprotection, the oligosaccharide is purified and its structure verified. A series of increasingly complex oligosaccharides has been assembled, each within 1 day or less, using the automated oligosaccharide synthesizer. This compares favourably with the weeks to months taken using solution-phase methods.

Another aspect of the present invention comprises the synthesis of the compounds of the general formula (I)

In one embodiment the synthesis of the compounds of the present invention are proceeds as follows:

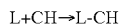

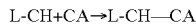

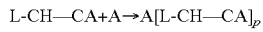

Specifically, in a particular preferred embodiment of the present invention the CH moiety is reacted with a linker molecule L after being protected with appropriate protection groups (PGs). Therein, the PGs may either be the same PGs or may also be different PGs such as PG' and PG" depending on the hydroxyl group on the CH moiety.

In a preferred embodiment of the present invention the protections groups PG' and PG" are different from each. In another preferred embodiment the protection groups PG' and PG" are the same.

As used herein protecting groups are preferably useful for secondary alcohols. In one embodiment silyl protecting groups such as trimethylsilyl (TMS), tert-butyldiphenylsilyl (TBDPS), tert-butyldimethylsilyl (TBS or TBDMS), triisopropylsilyl (TIPS) and [2-(trimethylsilyl)ethoxy]methyl (SEM) are used. In another preferred embodiment carbon ether protection groups are used such as methyl, n-butyl, tert.-butyl, p-methoxybenzyl, methoxy-methyl, trityl, vinyl, allyl, benzyloxymethyl, acetyl, pivolyl, 2-trichlor-1-imidoacetyl, 2-trichlor-1-N-phenylimioacetyl and tetrahydropyranyl. Yet, in another preferred embodiment of the present invention at least one silyl group for PG' and at least one carbon ether for PG" are used in one of the molecules (XXIX), (XXX) and (XXXII). Still in another preferred embodiment of the present invention in the molecules (XXIX), (XXX) and (XXXII) two different carbon ether protection groups are used for the protection groups PG' and PG", preferably at least one benzyl for PG" and at least one allyl group for PG', more preferably three benzyl groups for PG" in each 3, 4 and 5 four position in molecules (XXIX), (XXX) and (XXXII) and one allyl group for PG' in 2 position in molecules (XXIX) and (XXX).

Therefore, in a particular preferred embodiment a reaction sequence is conducted as follows:

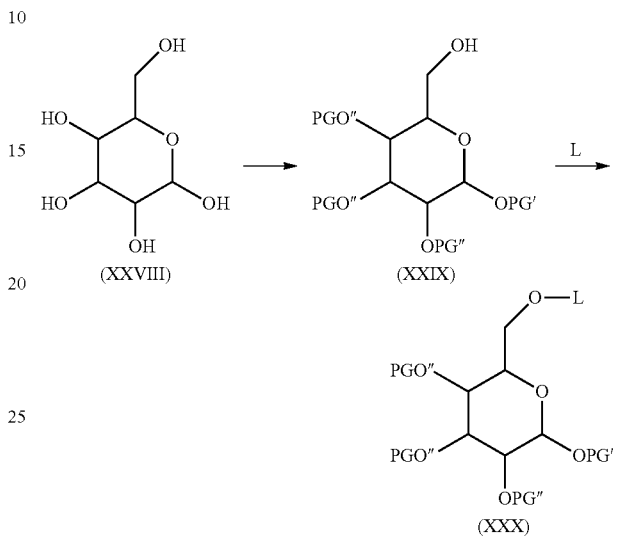

wherein L, PG' and PG" are as defined herein.

Subsequently in this embodiment the L-CH molecule (XXX) is converted in at least one reaction step, preferably in two reaction steps to intermediate L-CH—CA with a suitable precursor (XXXI) for the molecule CA:

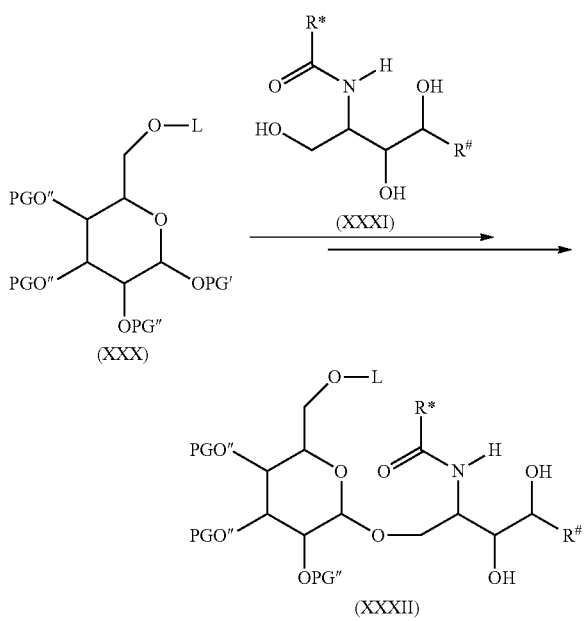

wherein A, L, PG', PG", R* and R# are as defined herein.

In the next reaction sequence of this particular embodiment intermediate (XXXII) is then deprotected from the protection groups PG" to intermediate (XXXIII) and reacted with any suitable antigen A to yield the compound (X) as one representative of the inventive compounds of the general formula (I):

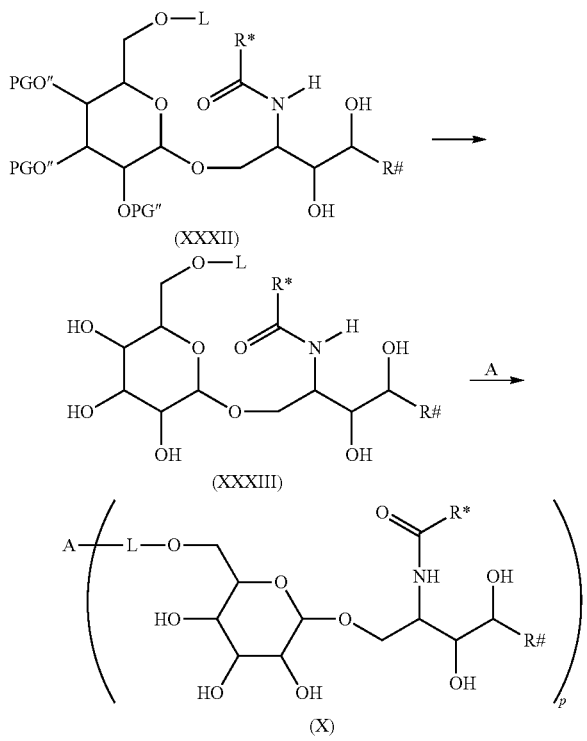

wherein A, L, PG", R* and R# are as defined herein.

In the synthesis of the compounds of the general formula (I) A[L-CH—CA]$_p$, and in particular as shown above in the synthesis of compounds of the general formula (X) it is preferred that the linker molecule L is introduced via a precursor which originates from diol (glycol) compound. Preferred are asymmetric precursor molecules for the linker L which have on the one side a nucleophilic group such as a halide or an activated hydroxy group and on the other side a functional group which can be converted into an amino group such as an azide, a protected amino group or nitrile. In a more preferred embodiment of the present invention the precursor molecules for the linker L have on the one side an activated alcohol functional group with a leaving group such as tosylate, triflat, or mesylate, and on the other side preferably a protected amino group or an azide. In a particularly preferred embodiment of the present invention the precursor molecule for the linker L has the general formula (XXXV)

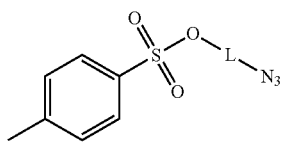

(XXXV)

which can be generally synthesized from diol (glycol) compounds of the general formula (XXXVI) HO-L-OH (XXXVI).

Also, preferred are linker being a linear or branched carbon chain with 2 to 30 carbon atoms and 0 to 6 hetero atoms selected from the group of —O—, —S— and —N(R$^N$)— and/or with one or more aromatic and/or carbocyclic and/or heterocyclic ring systems, wherein the linker is bond through a carbon atom to an oxygen atom of the carbonhydrate moiety (CH), preferably to the oxygen atom at the C6 carbon atom of the carbonhydrate moiety, and is directly or indirectly bond through a carbon atom to the antigen. This carbon chain is preferably bond through a methylen group of the carbon chain to the oxygen and preferably the C6-oxygen of the carbonhydrate moiety. Moreover this carbon chain is preferably bond through a methylen group or a carbonyl group of the carbon chain to a heteroatom and preferably a nitrogen atom of the antigen (A) and more preferably to a nitrogen atom of an amino group of the antigen. As used herein "directly bond" means that the carbon chain is attached to a functional group of the antigen, preferably an amino group of the antigen while the term "indirectly bond" refers to an attachment of the carbon chain to a spacer attached to the antigen so that the carbon chain is attached to the spacer which is connected to the antigen. Thus, such a spacer is interposed between the linker or respectively carbon chain and the antigen and can for example arise from the cleavage of an anhydride or a succinimide. Preferably the carbon chain has 2 to 25, more preferably 2 to 20, still more preferably 2 to 15 or 2 to 12 carbon atoms. It is also preferred that the carbon chain has up to 4 oxygen atoms and more preferably 1, 2 or 3 oxygen atoms and/or up to 4 sulfur atoms, preferably 1 or 2 sulfur atoms. Furthermore one or two substituted or unsubstituted phenylen rings can be present within the carbon chain.

In all described embodiments above a residue —R$^N$ represents —H, —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —CH$_2$—OCH$_3$, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_6$—OPh, —CH$_2$—OCH$_2$-Ph, —C$_2$H$_4$—OCH$_2$-Ph, —C$_3$H$_6$—OCH$_2$-Ph, —NO$_2$, —F, —Cl, —Br, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON (cyclo-C$_3$H$_5$)$_2$, —CON[CH(CH$_3$)$_2$]$_2$, —CON[C(CH$_3$)$_3$]$_2$.

In another embodiment of the present invention the order of connecting the respective moieties of the compounds of the present invention may be varied.

In another particular embodiment of the present invention first the moieties CH and CA are connected via suitable chemical reaction or reactions to yield intermediate CH—CA, and subsequently a linker molecule L is added to yield intermediate L-CH—CA which is then further reacted to furnish the compounds of the present invention of the general formula (I).

In another embodiment of the present invention antigen A is modified with linker molecule L to yield intermediate

[L-]$_q$A. Intermediate [L-]$_q$A can then further be reacted with intermediate CA-CH yielding the compounds of the present invention of the general formula (I).

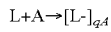

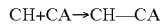

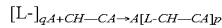

All reaction approaches may be modified to use or yield the respective preferred compounds of the subformulas (II) to (XXVII).

In that, according to the reaction sequence

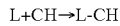

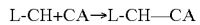

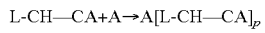

CH moieties with different connectivity as exemplified in subformulas (II) to (V) may be used. Similarly, CH moieties being monosaccharides, disaccharides or trisaccharides as exemplified in subformulas (VI) to (XIII), also with respect to stereochemical aspects as exemplified in subformulas (XIV) to (XVII) are suitable for the above reaction sequence. Further, the synthetic approach is also suitable to be applied to specific ceramid moieties as exemplified in subformulas (XVIII) to (XXIV), which also holds true for specific linker molecules as exemplified for the subsformulas (XXV) and (XXVII).

Therefore, the reaction sequence

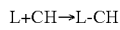

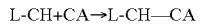

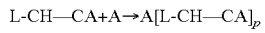

is suitable also for the synthesis of intermediates (II) to (XXVII) by choosing the respective moieties L, CH, and CA.

In a further preferred embodiment of the present invention the carbohydrate moiety and the ceramide are first joined together prior to introduction of the linker molecule. Therefore, a reaction sequent could also be as follows:

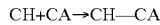

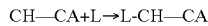

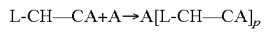

The present invention also comprises pharmaceutically acceptable salts of the compounds according to the general formula (I), all stereoisomeric forms of the compounds according to the general formula (I) as well as solvates, especially hydrates or prodrugs thereof.

In case, the inventive compounds bear basic and/or acidic substituents, they may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples for suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of an acid, selected out of the group mentioned above.

Some of the compounds of the present invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain compounds of the general formula (I) may exist in the form of optical isomers if substituents with at least one asymmetric center are present, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses. Where a compound according to the general formula (I) contains an alkene moiety, the alkene can be presented as a cis or trans isomer or a mixture thereof. When an isomeric form of a compound of the invention is provided substantially free of other isomers, it will preferably contain less than 5% w/w, more preferably less than 2% w/w and especially less than 1% w/w of the other isomers.

Another aspect of the present invention relates to the use of the inventive carbohydrate-glycolipid conjugate derivatives as drugs, i.e. as pharmaceutically active agents applicable in medicine.

Surprisingly it was found that the novel carbohydrate-glycolipid conjugates of the present invention are also suitable to raise an immune response in an animal and are suitable for vaccination against infectious diseases which are caused by pathogens selected from the group of bacteria, viruses, sporozoa, parasites or fungi. Moreover if the saccharide antigen is specific to cancer cells, the novel carbohydrate-glycolipid conjugates are suitable for the treatment and prophylaxis of cancers.

Both isolated and synthetic carbohydrate antigens are suitable for the formation of the described conjugate. Moreover it was found, that the treatment of an animal with the novel carbohydrate-glycolipid conjugates of the current invention lead to the formation of immunoglobuline IgG-isotypes, which prove the development of memory B-cells in the living organism. The presence of memory B-cells demonstrates immunological memory. Thus it has been shown, that the carbohydrate-glycolipid conjugates of the current invention are capable to induce a long term protection in an animal against a pathogen. The described vaccination is moreover independent on further adjuvants, does not need any protein-carrier and refrigeration of the vaccine.

Therefore, compounds according to the general formula (I-XXVII) are suitable for the use as a pharmaceutically active agent applicable in medicine, especially for use in vaccination against infectious diseases.

The infectious diseases for which vaccines can be provided by the compounds according to the present invention are selected from the group of bacterial, sporozoal, parasitic, fungal or viral infectious diseases. The bacterial infectious disease for which vaccines can be provided by the compounds according to the invention is caused by a pathogen selected from the group comprising:

*Allochromatium vinosum, Acinetobacter baumanii, Bacillus anthracis, Campylobacter jejuni, Clostridium* spp., *Citrobacter* spp., *Escherichia coli, Enterobacter* spp., *Enterococcus faecalis., Enterococcus faecium, Francisella tularensis, Haemophilus influenzae, Helicobacter pylori, Klebsiella* spp., *Listeria monocytogenes, Moraxella catharralis, Mycobacterium tuberculosis, Neisseria meningitidis, Neisseria gonorrhoeae, Proteus mirabilis, Proteus vulgaris, Pseudomonas aeruginosa, Salmonella* spp., *Serratia* spp., *Shigella* spp., *Stenotrophomonas maltophilia, Staphyloccocus aureus, Staphyloccocus epidermidis, Streptococcus pneunmoniae, Streptococcus pyogenes, Streptococcus agalactiae, Yersina pestis*, und *Yersina enterocolitica*.

The parasitic infectious disease for which vaccines can be provided by the compounds according to the invention is caused by a pathogen selected from the group comprising:

*Babesia, Balantidium, Besnoitia, Blastocystis, Coccidia, Cryptosporidium, Cytauxzoon, Cyclospora, Dientamoeba, Eimeria, Entamoeba, Enterocytozoon, Enzephalitozoon, Eperythrozoon, Giardia, Hammondia, Isospora, Leishmania, Microsporidia, Naegleria, Plasmodium, Plasmodium falciparum, Plasmodium vivax, Plasmodium ovale, Plasmodium malariae, Plasmodium knowlesi, Pneumocystis, Schistosoma, Sarcocystis, Theileria, Trichinella, Toxoplasma, Trichomonas, Trypanosoma, Unicaria, Cestoda, Dipylidium, Dranunculus, Echinococcus, Fasciola, Fasciolopsis, Taenia, Ancylostoma, Ascaris, Brugia, Enterobius, Loa loa, Mansonella, Necator, Oncocerca, Strongyloides, Strongylus, Toxocara, Toxascaris, Trichuris oder Wucheria*.

The fungal infectious disease for which vaccines can be provided by the compounds according to the invention is caused by a pathogen selected from the group comprising:

*Trichophyton mentagrophytes, Trichophyton rubrum, Trichophyton interdigitale, T. schönleinii, T. verrucosum, T. violaceum, T. tonsurans, Trichophyton* spp., *M. canis, Candida albicans, C. guillermondii, C. krusei, C. parapsilosis, C. tropicalis, C. glabrata, Candida* spp., *Microsporum* spp., *Microsporum canis, Microsporum audonii, Microsporum gypseum, M. ferrugineum, Trichosporum beigelii, Trichosporum inkiin, Aspergillus niger, Alternaria, Acremonium, Fusarium*, or *Scopulariopsis*.

The viral infectious disease for which vaccines can be provided by the compounds according to the invention is caused by a pathogen selected from the group comprising:

Adenoviruses, Ebolavirus, Epstein-Barr-virus, Flavivirus, FSME-virus, Influenza virus, Hanta-virus, human immunodeficiency virus ("HIV"), herpes simplex virus ("HSV", type 1 or 2), human herpes virus 6 (HHV-6), human Papilloma virus ("HPV", type 16 or 18), human Cytomegalovirus ("HCMV"), human hepatitis B or C virus ("HBV", Type B; "HCV", type C), Lassavirus, Lyssavirus (EBL 1 or EBL 2), Marburgvirus, Norovirus, Parvovirus B19, Pestvirus, Poliovirus, Rhinovirus, Rotaviruses, SARS-assciated Coronavirus, Varicella-Zoster virus.

Among the cancers the novel carbohydrate-glycolipid conjugates are suitable for, the attention has been given to Bladder Cancer, Breast Cancer, Colon and Rectal Cancer, Endometrial Cancer, Kidney (Renal Cell) Cancer, Leukemia, Lung Cancer Melanoma, Non-Hodgkin Lymphoma, Pancreatic Cancer, Prostate Cancer, Thyroid Cancer.

Among the infectious diseases, the attention has been given to *Haemophilus influenzae* and *Streptococcus pneunmoniae*.

Therefore, another aspect of the present invention is directed to pharmaceutical compositions comprising at least one compound of the present invention as active ingredient, together with at least one pharmaceutically acceptable carrier, excipient and/or diluents. The pharmaceutical compositions of the present invention can be prepared in a conventional solid or liquid carrier or diluent at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention, and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95 weight % of the benzothiophene-1,1-dioxide derived compound and/or the respective pharmaceutically active salt as active ingredient.

Suitable binders include starch, gelatin, natural carbohydrates, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticisers and/or preservatives. Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include carbohydrates such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include carbohydrates such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

Said pharmaceutical compositions may further comprise at least one active carbohydrate-glycolipid conjugate of the general formula (I).

The pharmaceutical compositions may further comprise at least one further active agent. It is preferred if this active agent is selected from the group consisting of anti-depressant and other psychotropic drugs. It is further preferred if the anti-depressant is selected from amitriptyline, amioxide clomipramine, doxepine, duloxetine, imipramine trimipramine, mirtazapine, reboxetine, citaloprame, fluoxetine, moclobemide and sertraline.

A further embodiment of the invention comprises the average ratio of the carbohydrate antigen A to the glycolipid (L-CH—CA) which may vary between 1:4 and 1:100 (n/n).

Another embodiment of the invention comprises the compounds of the invention, according to the general formula (I) which may be used for the preparation of a vaccine formulation for the use in vaccination of an animal. The mentioned vaccine formulation may comprise one or more of the compounds of the present invention or a mixture of different compounds of the invention and preferably of the general formula (I), wherein the mixture of different compounds of the general formula (I) preferably comprises a mixture of different serotypes of the used carbohydrate antigen A, and/or the mixture of different compounds of the general formula (I) may comprise a mixture of different carbohydrate antigens A, which are used in different compounds of the general formula (I). The mentioned mixture of different compounds of the general formula (I) within the vaccine formulation can therefore constitute a combinantion of vaccines which can be used for a combinated vaccination against more than at least one pathogen.

In a further embodiment of the invention, the vaccine formulation may comprise a mixture of different compounds of the general formula (I).

The mentioned vaccine formulations may further comprise a combination with at least one pharmaceutically acceptable carrier, excipient and/or diluents.

The compounds of the invention of the general formula (I) are present in said vaccine formulation in the range of 10 to 1000 μg/g.

In a preferred embodiment of the invention the compounds of the general formula (I) are present in said vaccine formulation in the range of 10 to 1000 ng/g.

In a more preferred embodiment of the invention the compounds of the general formula (I) are present in said vaccine formulation in the range of 100 to 1000 pg/g.

The mentioned vaccine formulation displays an extraordinary stability at room temperature due to the modular constitution of the compounds of the present invention, wherein said vaccine formulation may be maintained at a temperature of at least 25° C. for a period of at least 3 months prior to reconstitution.

In a preferred embodiment of the invention the said period is comprises 6 months or at least 12 months.

The surprising advantages of the conjugates of the present invention were found by in vitro and in vivo application.

Specifically, when applied in an in vitro the glycoconjugate vaccine according to the present invention retains the capacity to stimulate iNKT cells when presented by CD1d-positive antigen-presenting cells (APC). Additionally it was found that the compounds of the present invention fail to stimulate the same iNKT cells when loaded onto plate-bound recombinant CD1d. Without being bound to theory it appears that the saccharidic moiety is properly coupled and hinders T cell recognition.

Further, when applied in vivo the conjugates of the present invention were found of being capable of effectively and continuously immunizing against a pathogen. This is rather advantageous since thereby the conjugates of the present invention cannot only stimulate the generation of antibodies of high titers and long lasting resistance in in vivo conditions, moreover the compounds of the present invention themselves exhibit a long-term stability at room temperature. Therefore, the conjugates of the present invention are particular heat stable and thus no refrigeration is required.

EXAMPLES

General Methods

Cells. The APC lines MOLT-4 (ATCC CRL 1582), which expresses only negligible CD1d, and human CD1d-transfected C1R and HeLa cells (C1R-hCD1d and HeLa-hCD1d, respectively) [6] were maintained in RPMI-1640 medium containing 10% FCS, 2 mM L-glutamine, 1 mM sodium pyruvate, 100 μM non-essential aminoacids, and 100 μg/ml kanamycin. The same maintenance conditions were used for RAW (mouse leukemic monocyte macrophage cell line), J774A.1 (mouse, BALB/c, monocyte-macrophage, not defined tumor), HL60 and NB4 (both human promyelocytic leukemia) cells. Isolation of iNKT cell clones from PBMC of healthy donors has been described before [7]. iNKT cells were maintained in RPMI-1640 medium containing 5% HS, 2 mM L-glutamine, 1 mM sodium pyruvate, 100 μM non-essential aminoacids, 100 μg/ml kanamycin, and 100 U/ml recombinant IL-2.

Mice. C57BL/6, BALB/c and B6; 129-CD1<tmlGru> (CD1KO) [8] mice were bred at our institute (Versuchsstation Departement Biomedizin, Basel, Switzerland) or C57BL/6 were also bought from Charles River Laboratories (Sulzfeld, Germany). This study was reviewed and approved by the "Kantonales Veterinäramt Basel-Stadt" 20 in Basel, Switzerland.

Bacteria. *Streptococcus pneumoniae* serotype 4 reference strain (Statens Serum Institute, Denmark) was grown in Todd-Hewitt broth supplemented with 0.5% yeast extract at 37° C.

Infections. Non-/ and vaccinated mice were challenged with *S. pneumoniae* serotype 4 and mortality, weight loss and clinical score were recorded over time.

Opsonizations. 5 mM 5-chloromethylfluorescein diacetate (CMFDA, Invitrogen, Switzerland) labeled and non-fixed or fixed bacteria were coated with 10% rabbit complement (HD supplies, UK) and/or purified CPS-specific mAbs for up to 1 h. Mixed bacteria with dimethylformamide-(Sigma-Aldrich, Switzerland) or non-induced cells at a ratio of 10-100:1 for up to 2 h at 37° C. Samples were acquired on a CyAn ADP flow cytometer (Beckman Coulter, Switzerland). Data were gated to exclude non-viable cells on the basis of light scatter, pulse width, and incorporation of propidium iodide and further analyzed using Summit software (Beckman Coulter).

Activation Assays. In vitro antigen presentation assays by living APC or plate-bound antigen-presenting molecules were performed as previously described [9]. Briefly, living APC were plated at $2.5 \times 10^4$/well in 96-well plates and incubated during the whole assay at 37° C. with vehicle or titrating doses of αGalCer or conjugate vaccine. After 1 h human iNKT cells ($0.5\text{-}1 \times 10^5$/well) were added. Cell culture supernatants were harvested after 24-48 h and release of cytokines was measured by ELISA. For plate-bound activation, purified recombinant soluble human CD1d (rshCD1d) was obtained by IEF and added to Bir1.4 mAb-coated (10 μg/ml, specific for the BirA tag of rshCD1d) MaxiSorp Plates (Nunc) overnight. Bound rshCD1d was pulsed with 2 μg/ml αGalCer or different doses of conjugate vaccine. Human iNKT cell clones ($1.5 \times 10^5$/well) were added to the plate and after 24-48 h released cytokines were measured by ELISA.

ELISA. For detection of human cytokines, the following purified capture and biotinylated detection monoclonal antibody (mAb) pairs (all BioLegend, San Diego, USA) were used: hTNFα (MAb1 1 μg/ml and MAb11 0.5 μg/ml), hIFNγ (MD-1 2 μg/ml and 4S.B3 0.5 μg/ml), hIL-4 (8D4-8 1 μg/ml and MP4-25D2 0.5 μg/ml), hGM-CSF (BVD2-23B6 3.33 μg/ml and BVD2-21C11 0.5 μg/ml), hIL-8 (JK8-1 1.25 μg/ml and JK8-2 1 μg/ml). For detection of mouse cytokines, the following mAb pairs (all Becton Dickinson (BD), Allschwil, Switzerland) were used: mIL-2 (JES6-1A12 2 μg/ml and JES6-5H4 1 μg/ml), mIL-4 (11B11 1 μg/ml and BVD6-24G2 1 μg/ml), mIFNγ (R4-6A2 2 μg/ml and XMG1.2 1 µg/ml). For detection of Abs, plates were coated with 1 µg/ml biotin goat anti-mouse (GAM) Ig (BD, 553999) and revealed with 1:10'000 HRP-labeled GAM-IgG (Sigma-Aldrich, Buchs, Switzerland, A0168) or with 1:1'000 (all SouthernBiotech, Birmingham, USA) HRP-labeled GAM-IgM (1020-05), GAM-IgG1 (1070-05), GAM-IgG2a (1080-05), GAM-IgG2b (1090-05), GAM-IgG3 (1100-05) or coated with 2.5 µg/ml CPS and revealed with (all Biolegend) biotinylated rat anti-mouse (RAM)-IgG1 (clone RMG1-1, 1 µg/ml), -IgG2a (clone RMG2α-62, 1 µg/ml), -IgG2b (clone RMG2b-1, 0.5 µg/ml), -IgG3 (clone RMG3-1, 0.5 µg/ml) or donkey anti-mouse IgM (Jackson ImmunoResearch, Suffolk, UK, 0.95 µg/ml) or GAM F(ab')2 IgG (abcam, 0.1 µg/ml) GAM Ig (BD, 2 µg/ml).

Statistical Analysis. Survival data were compared with the Mantel-Cox and Gehan-Breslow-Wilcoxon test. All analyses were performed using GraphPad Prism software (version 5.03). Differences were considered significant at P<0.05.

Chemicals and Structure Analysis. All chemicals used were reagent grade and used as supplied except where noted. Dimethylformamide (DMF), tetrahydrofuran (THF), toluene, dichloromethane ($CH_2Cl_2$) and diethyl ether ($Et_2O$) were purchased from JT Baker or VWR International and purified by a Cycle-Tainer Solvent Delivery System. Pyridine, triethylamine ($NEt_3$) and acetonitrile (MeCN) were refluxed over calcium hydride and distilled. Solvents for chromatography and workup procedures were distilled. Reactions were performed under an argon or nitrogen atmosphere except where noted. Analytical thin-layer chromatography was performed on E. Merck silica gel 60 $F_{254}$ plates (0.25 mm). Compounds were visualized by UV-light at 254 nm and by dipping the plates in a cerium sulfate ammonium molybdate (CAM) solution or a sulfuric acid/methanol solution followed by heating. Liquid chromatography was performed using forced flow of the indicated solvent on Fluka silica gel 60 (230-400 mesh). $^1$H NMR spectra were obtained on a Varian VXR-300 (300 MHz), Varian VXR-400 (400 MHz), Bruker DRX500 (500 MHz), and Bruker AV600 (600 MHz) and are reported in parts per million (δ) relative to the resonance of the solvent or to TMS (0.00 ppm). Coupling constants (J) are reported in Hertz (Hz). $^{13}$C NMR spectra were obtained on a Varian VXR-300 (75 MHz), Varian VXR-400 (101 MHz), Bruker DRX500 (125 MHz), and Bruker AV600 (150 MHz) and are reported in δ relative to the resonance of the solvent or to TMS (0.00 ppm). IR Spectra: Measured as 1-2% $CHCl_3$ solution on a Perkin-Elmer-782 spectrophotometer or neat on a Perkin-Elmer-100 FT-IR spectrometer. Recycling preparative size exclusion HPLC (LC-9101, Japan Analytical Industry Co.); flow rate: 3.5 mL/min; solvent: $CHCl_3$. Optical rotations $[\alpha]^{rt}_D$ were measured on a Jasco DIP-370 polarimeter (10 cm, 1 mL cell); the solvents and concentrations (in g/100 mL) are indicated. High-resolution mass spectra were performed by the MS service FU Berlin and are given in m/z.

Example 1

In Vitro Activity of the Conjugate Vaccine

The glycoconjugate vaccine (*S. pneumoniae* serotype 4 CPS coupled to αGalCer) retains the capacity to stimulate iNKT cells when presented by CD1d-positive antigen-presenting cells (APC) but fails to stimulate the same iNKT cells when loaded onto plate-bound recombinant CD1d (FIGS. 3A and 3B, respectively). These findings indicate that the saccharidic moiety is properly coupled and hinders T cell recognition but can be cleaved off from the stimulatory αGalCer glycolipid by living APC.

Example 2

In Vivo Activity of the Conjugate Vaccine

The glycoconjugate consisting of CPS type 4 coupled to αGalCer was used to immunize wild-type (WT) C57BL/6 mice. Three immunizations were performed with intervals of 14 days. These mice showed high titers of anti-polysaccharide Abs compared to naïve or CPS only immunized mice (FIG. 4A) up to 3 months after the last immunization. This argues in favor of a long-lasting Abs response by B cells only when helped by αGalCer-responsive iNKT cells.

The glycoconjugate vaccine was used to immunize WT C57BL/6 and CD1d-deficient (CD1d−/−, CD1KO) mice. Two immunizations were performed with an interval of 7 days. WT mice showed high titers of anti-polysaccharide antibodies (Abs), which instead were not observed in CD1d-deficient mice (FIG. 4B), indicating that expression of CD1d is necessary for the adjuvant-like effect of αGalCer.

Conclusively, the glycoconjugate vaccine-induced antibody response is dependent on the presence of iNKT cells and of CD1d as CD1d KO mice fail to generate high titers of CPS-specific antibodies after immunization.

Example 3

Analysis of the In Vivo Antibody Response after Vaccination

When CPS-specific Abs were investigated by ELISA using isotype-specific secondary reagents, the presence of IgG1 CPS-specific Abs was detected only in WT mice whereas CD1KO mice were unable to induce IgG1 (FIG. 5A). The same finding was confirmed with other IgG subtypes. These experiments prove that immunization with CPS type 4 coupled to αGalCer glycoconjugate facilitates the class switch of polysaccharide-specific antibodies to all IgG isotypes.

The generated Abs partially cross-reacted with CPS of type 2 *S. pneumoniae* (FIG. 5B). They might also recognize common epitopes on CPS of other serotypes as very high titers of total immunoglobulin were detected assessing reactivity to a CPS mix of several *S. pneumoniae* serotypes (data not shown).

Several hybridomas expressing CPS-specific Abs were established from mice immunized twice and sacrificed 1.5 months after the last boost. We could isolate hybridomas expressing IgM and all IgG subclasses, with the exception of IgG2b. The IgM-positive hybridomas were affinity matured (FIG. 6).

These preliminary experiments demonstrate that immunization with CPS type 4 coupled to αGalCer glycoconjugate facilitates switching of polysaccharide-specific B cells to IgG isotypes and/or affinity maturation of the CPS-specific Abs.

All hybridomas derived from glycoconjugate immunized mice showed class switching and affinity maturation. Somatic mutation seems a frequent event as two of the IgG1 hybridomas used the same VDJ rearrangement. Moreover several IgM hybridomas were identical except for junctional diversity by P- and N-nucleotides.

These mAbs were assessed for their ability to fix complement and enhance opsonization by phagocytic cells. Using CMD-labelled bacteria, we found that CPS-specific Abs upregulated bacterial phagocytosis (FIG. 7).

Example 4

Protection from Infection with *S. pneumoniae* in a Mouse Model

Immunization with the glycoconjugate vaccine protects C57BL/6 mice from infection with *S. pneumoniae*. αGalCer-CPS type 4 vaccinated mice show short- and long-term protection to challenge with *S. pneumoniae* (FIG. 8B). Furthermore, mice vaccinated with αGalCer-CPS type 4 suffered a less severe disease than CPS type 4 only immunized mice as shown by no weight loss upon infection (FIG. 8A, 3 and 3 representative animals).

Example 5

Synthesis of the Carbohydrate-Glycolipid Conjugate Vaccine

Synthesis of the lipid portion of the conjugate vaccine started using Weinreb amide of N-Boc-L-serine 2 (Scheme 1) which was formed using EDCl as coupling reagent, N-methyl morpholine as base, and N,O-dimethyl hydroxylamine. Mixed N,O-acetal formation with 2,2-dimethoxypropane and catalytic amounts of $BF_3OEt_2$ yielded amide 3. Reduction of the latter with lithium aluminium hydride at 0 C yielded Garner's aldehyde 4. Z-Selective Wittig olefination using pentadecyltriphenylphosphonium ylide furnished alkene 5. Removal of the acetal group on olefin 5 was followed by Sharpless' asymmetric dihydroxylation with AD-mix β and methylsulfonamide, furnishing N-Boc protected diol 6 in good yield and selectivity. Subsequent removal of the carbamate group furnished phytosphingosine 7. Amide bond formation was performed with hexacosanoic N-hydroxy succinimidyl ester 11 and triethylamine as base, to yield 8. Addition of TBSOTf and 2,6-lutidine yielded trisilyl ether 9. The silyl ether on the primary hydroxyl group was then selectively removed with aq. TFA to give ceramide acceptor 10. [2]

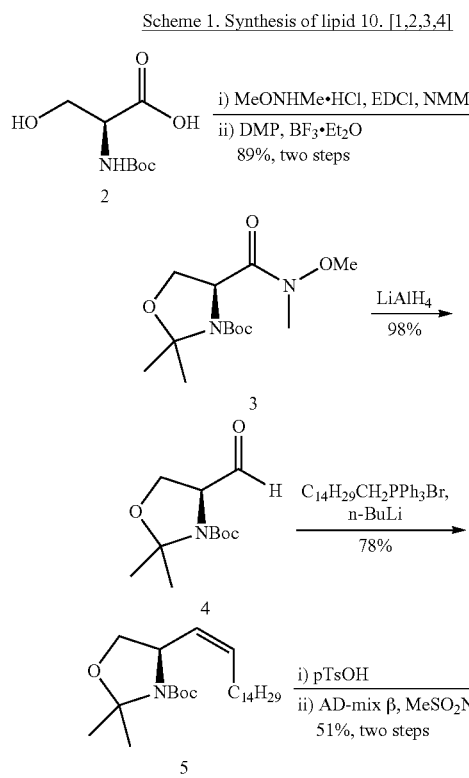

Scheme 1. Synthesis of lipid 10. [1,2,3,4]

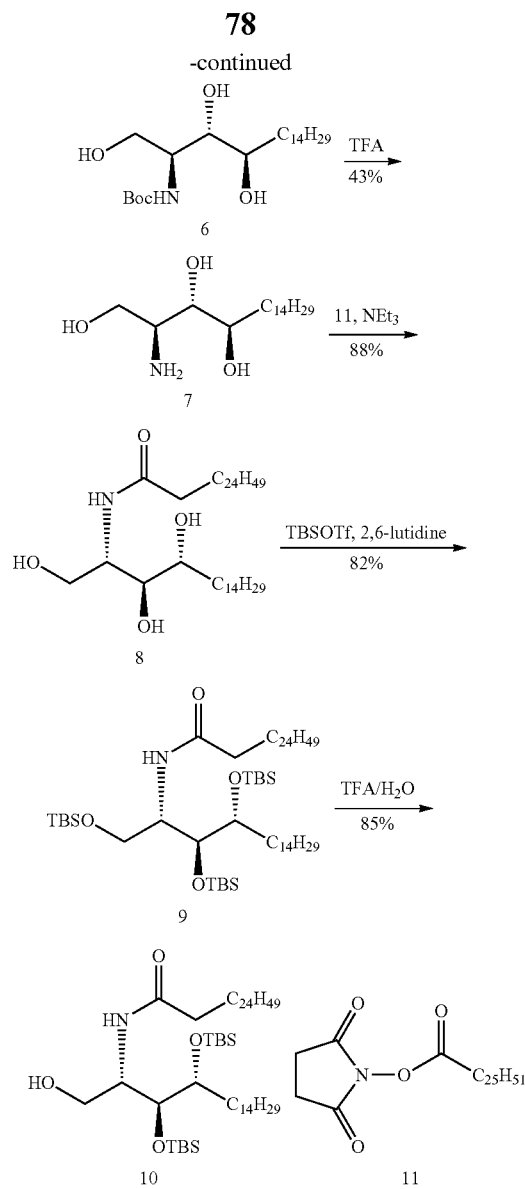

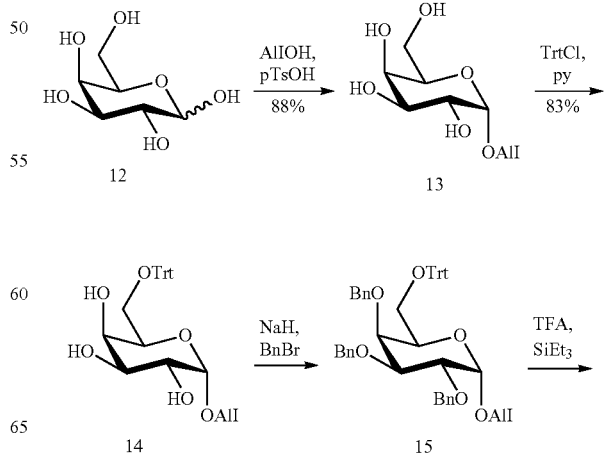

Scheme 2. Synthesis of galactosylating agent 19.

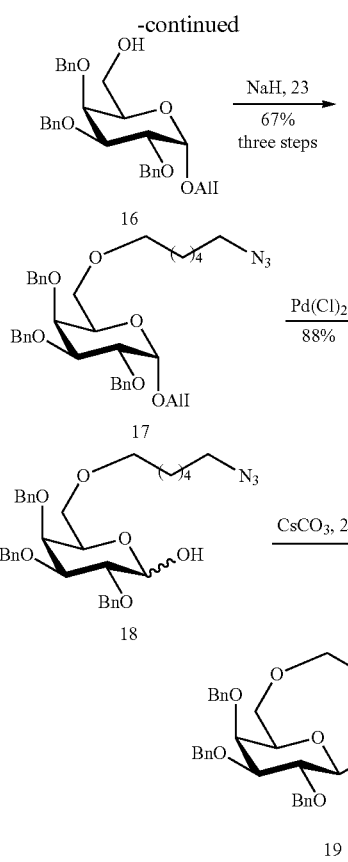

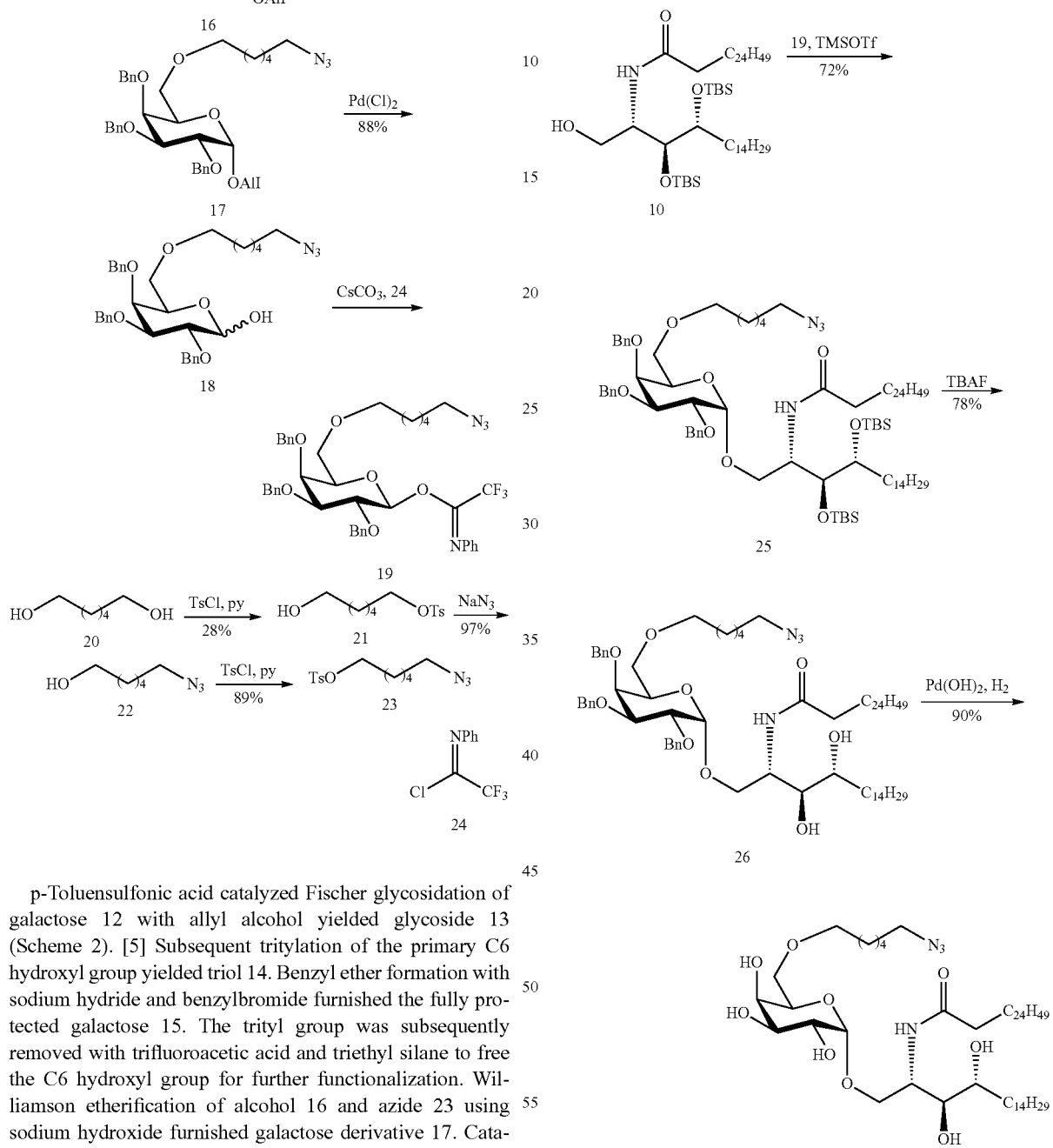

of 21 was displaced by sodium azide to yield azide 22. Subsequent tosylation of the hydroxyl group on 22 gave the tosylate 23.

Scheme 3. Synthesis of linker-equipped glycolipid 27.

p-Toluensulfonic acid catalyzed Fischer glycosidation of galactose 12 with allyl alcohol yielded glycoside 13 (Scheme 2). [5] Subsequent tritylation of the primary C6 hydroxyl group yielded triol 14. Benzyl ether formation with sodium hydride and benzylbromide furnished the fully protected galactose 15. The trityl group was subsequently removed with trifluoroacetic acid and triethyl silane to free the C6 hydroxyl group for further functionalization. Williamson etherification of alcohol 16 and azide 23 using sodium hydroxide furnished galactose derivative 17. Catalytic isomerization of the anomeric allyl protecting group to the corresponding enol ether with palladium(II) chloride and subsequent hydrolysis yielded lactol 18 which was converted into glycosyl imidate 19 with cesium carbonate and N-phenyltrifluoroacetimidazoyl chloride 24.

Linker 23 was prepared starting from 1,6-hexanediol 20 which was reacted with tosyl chloride to yield a mixture of the corresponding mono- and di-tosylated product along with the starting material. After separation, the tosyl group Linker-equipped glycolipid 25 (Scheme 3) was obtained via TMSOTf-catalyzed glycosylation of galactose building block 19 and ceramide 10. The reaction proceeded in 72% yield and with complete α-selectivity. Removal of the silylether protecting groups with TBAF yielded diol 26 that was converted to 27 by hydrogenolysis with Perlman's catalyst.

Scheme 3. Alternative synthesis of linker-equipped glycolipid 27a.
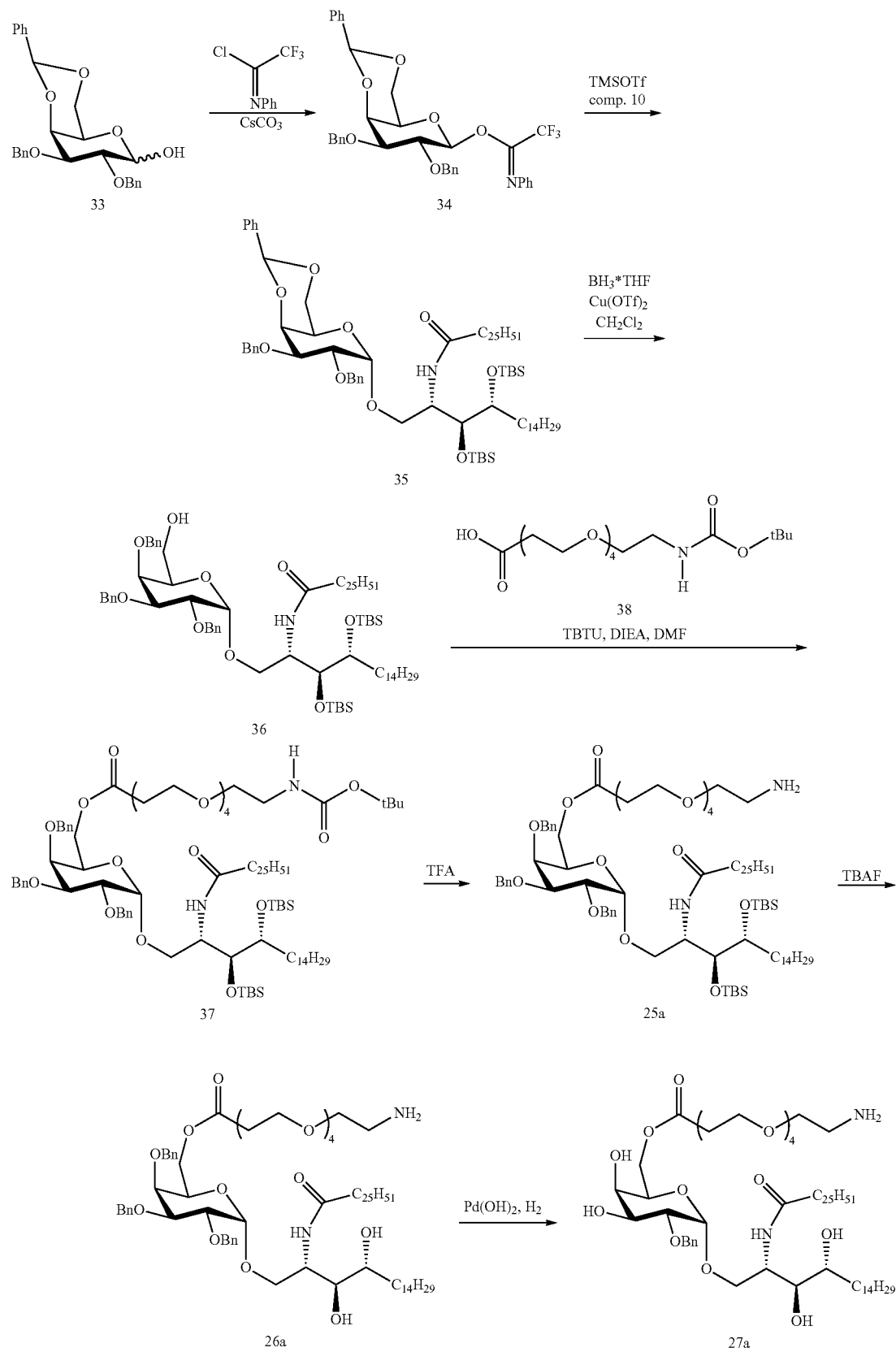

The glycolipid 36 was prepared in three steps from the known compound 33 by reacting the activated compound 34 with derivatives of compounds 10 by the above TMSOTf-catalyzed glycosylation of galactose building block. After deprotection of compound 35 the linker was introduced by condensation reaction with compound 38 in moderate yields. The linker-equipped glycolipid 27a was subsequently prepared via intermediates 25a and 26a by complete deprotection of linker-equipped compound 37.

Conjugation of the polysaccharide to the glycolipid 27 was accomplished via a covalent linkage. To this end PS4 was activated with cyanogen bromide to which 27 was added in order to give conjugate 1 (Scheme 4).

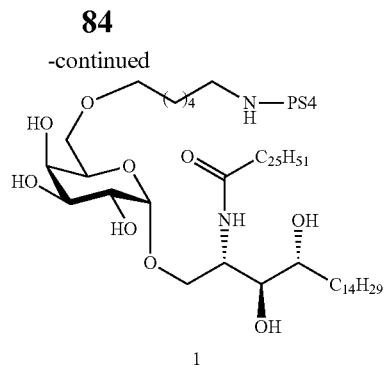

1

Scheme 4. Conjugation of glycolipid 27 to PS4

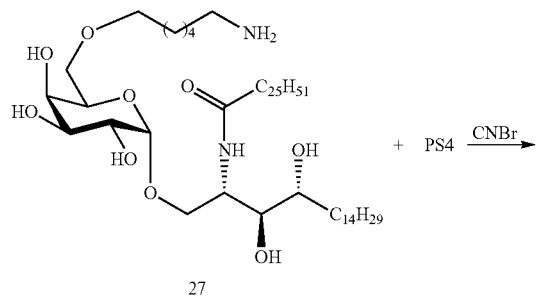

A hydrazone linkage provides an alternative conjugation method to link the epitope moiety with the glycolipid. To this end a hydrazone linkage can be used (Scheme 5). Antigen 28 has to be modified to aromatic aldehyde 30 using NHS-ester 29 and GSL 27 will be converted to hydrazone 32 using NHS-ester 31. Coupling of aldehyde 30 and hydrazone 32 occurs at a pH of 4.7 to 7.2. The linker system is commercially available from Novabiochem (HydraLinK™).

Scheme 5. Conjugation of amine linker-equipped antigen 28 with glycolipid 27 via hydrozone linkage.

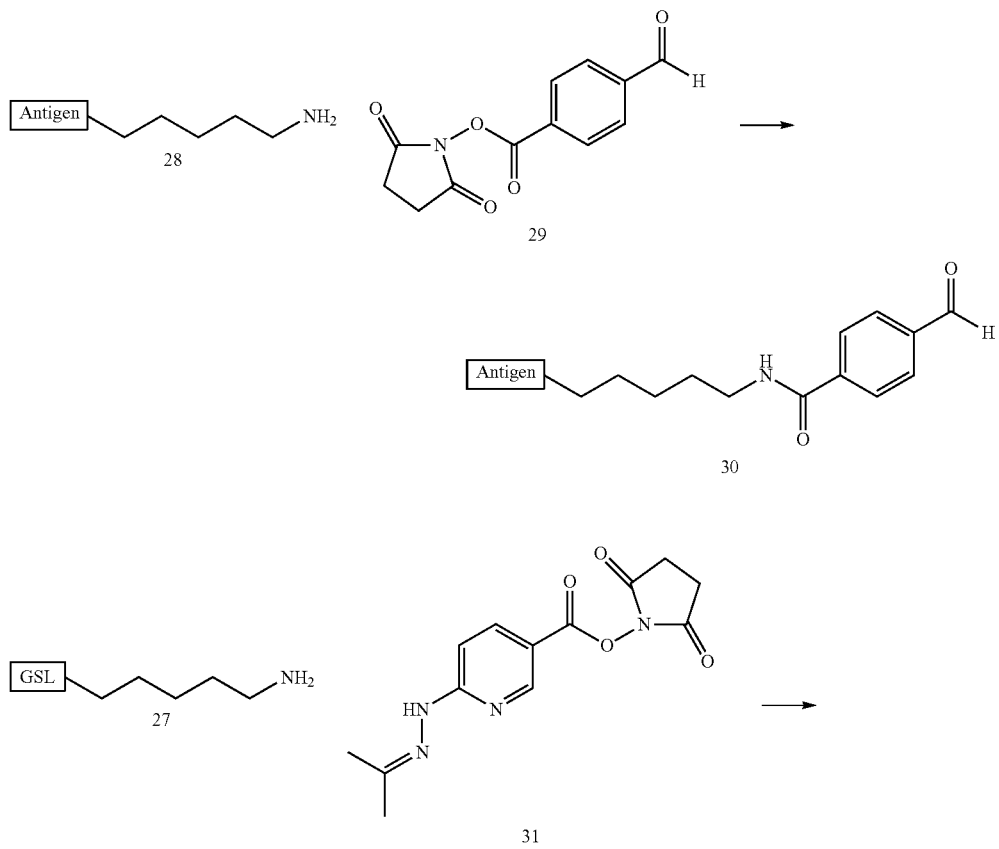

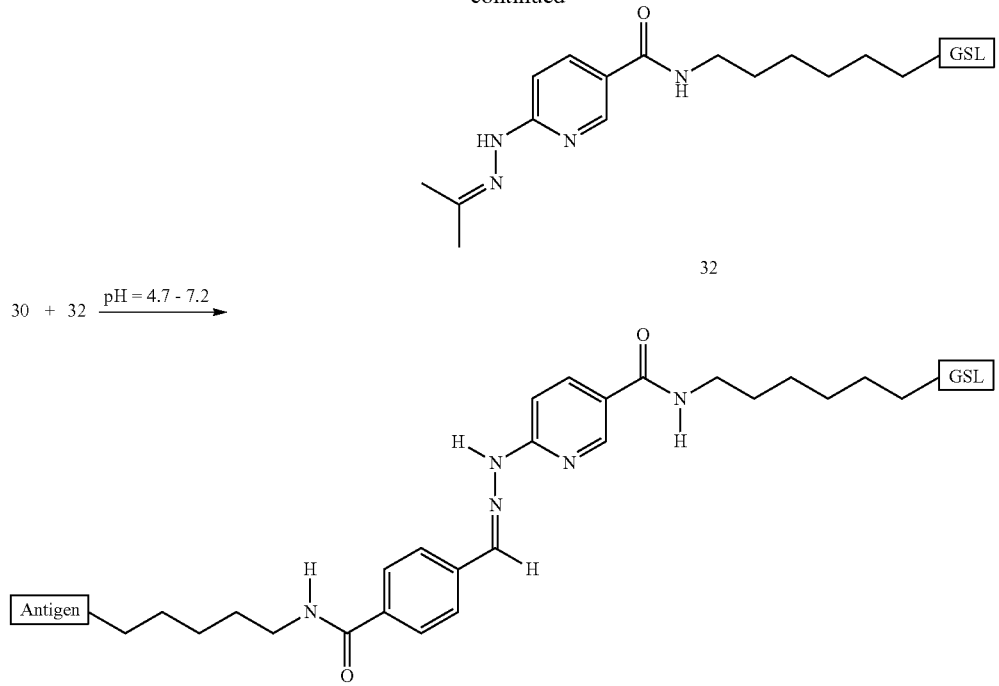

30 + 32 $\xrightarrow{\text{pH} = 4.7 - 7.2}$

Experimental Procedures

(S)-3-(tert-Butoxycarbonyl)-N-methoxy-2,2,N-trimethyloxazolidine-4-carboxamide (3)

To a solution of L-Boc-serine 2 (12.33 g, 60.1 mmol) in $CH_2Cl_2$ (240 mL) were added N,O-dimethylhydroxylamine hydrochloride (6.04 g, 61.9 mmol) and N-methylmorpholine (6.8 mL, 61.9 mmol) at 0° C. To this solution was added N-(3-dimethylaminopropyl)-N'-ethylcarbodiimide hydrochloride (11.86 g, 61.9 mmol) portionwise over a period of 20 min. and the solution was stirred for another 1 h. Then, aq. HCl solution (1.0 M, 30 mL) was added and the aqueous layer was extracted with $CH_2Cl_2$ (2×100 mL). The combined organic layers were washed with sat. aq. $NaHCO_3$ solution (30 mL) and the aqueous layer was again extracted with $CH_2Cl_2$ (100 mL). The combined organic layers were dried over $MgSO_4$ and the solvent was removed in vacuo to obtain the corresponding Weinreb amide (14.07 g, 94%) as white solid. $R_f$=0.3 (EtOAc); $^1$H NMR (250 MHz, $CDCl_3$) δ 5.60 (d, J=6.0 Hz, 1H), 4.77 (br s, 1H), 1.42 (s, 9H), 3.80 (d, J=3.3 Hz, 2H), 3.76 (s, 3H), 3.21 (s, 3H), 2.66 (br s, 1H). The crude product was dissolved in acetone (180 mL) to which 2,2-dimethoxypropane (57 mL) and $BF_3Et_2O$ (0.5 mL) were added. The orange solution was stirred for 90 min. at r.t. and then quenched with $Et_3N$ (1.2 mL) and solvents removed in vacuo. The crude product was purified by flash column chromatography on silica gel (gradient EtOAc/cyclohexane=1:2→1:1) to yield isopropylidene-protected Weinreb amide 3 (15.32 g, 89% over two steps) as a white solid. The NMR spectra consist of two sets of signals due to the presence of rotamers. $[\alpha]_D^{r.t.}$=−30.9 (c=1, $CHCl_3$); $R_f$=0.45 (Hexanes/EtOAc=1:1); IR (film) $v_{max}$ 2976, 2938, 1702, 1682, 1364, 1167, 1098, 998, 848, 768, 716; $^1$H NMR (250 MHz, $CDCl_3$) δ 4.77 (dd, J=9.8, 2.8 Hz, 1 H), 4.70 (dd, 7.5, 3.8, Hz, 1 H), 4.18 (dd, J=7.5, 4.0 Hz, 1 H), 4.15 (dd, J=7.8, 3.8 Hz, 1 H), 3.95 (dd, J=9.3, 3.0 Hz, 1 H), 3.91 (dd, J=9.0, 3.5 Hz), 3.72 (s, 3 H), 3.68 (s, 3 H), 3.19 (s, 6 H), 1.68 (s, 3 H), 1.66 (s, 3 H), 1.54 (s, 3 H), 1.50 (s, 3 H), 1.47 (s, 9 H), 1.39 (s, 9 H); $^{13}$C NMR (101 MHz, $CDCl_3$) δ 171.4, 170.7, 152.2, 151.4, 95.1, 94.5, 80.6, 80.0, 66.2, 66.0, 61.3, 61.3, 57.9, 57.8, 28.5, 28.4, 25.8, 25.5, 24.8, 24.6; HR ESI Calcd for $C_{13}H_{24}N_2O_5$ [M+Na$^+$]: 311.1577. found: 311.1582.

tert-Butyl (S)-4-formyl-2,2-dimethyloxazolidine-3-carboxylate (4)

To a solution of Weinreb amide 3 (8.00 g, 27.7 mmol) in THF (100 mL) at 0° C. were added $LiAlH_4$ (1.0 M in THF, 13.9 mL, 13.9 mmol) dropwise and the solution was stirred for 1 h at 0° C. After 1 h, the solution was cooled to −10° C. and $KHSO_4$ (1M, 70 mL) was added carefully and the solution was diluted with $Et_2O$ (170 mL). The mixture was allowed to warm to r.t. and stirred for 30 min. The organic layer was separated, dried over $MgSO_4$, filtered and the solvent was removed in vacuo to yield Garner's aldehyde 4 as a pale yellow oil (6.24 g, >95% purity by $^1$H NMR). The NMR spectra consist of two sets of signals due to the presence of rotamers. $^1$H NMR (250 MHz, $CDCl_3$) δ 9.58 (d, J=0.8 Hz, 1H), 9.52 (d, J=2.5 Hz, 1 H), 4.32 (m, 1 H), 4.16 (m, 1 H), 4.06 (m, 4 H), 1.53-1.63 (m, 12H), 1.49 (s, 9 H), 1.40 (s, 9 H). The crude product was used in the subsequent reaction without further purification.

(4R,1'Z)-3-(tert-Butoxycarbonyl)-2,2-dimethyl-4-(1'-hexadecenyl)oxazolidine (5)

n-BuLi (1.6 M in hexane, 25.2 mL, 40.3 mmol) was added dropwise to pentadecyltriphenylphosphonium bromide (24.03 g, 43.4 mmol) in anhydrous THF (220 mL) at −78° C. The resulting orange solution was allowed to warm to 0° C. and stirred for another 30 min. The solution was then cooled to −78° C. and Garner's aldehyde 4 (6.23 g, 27.2 mmol) in anhydrous THF (30 mL) was added slowly. After being stirred for 2 h at r.t., the reaction was diluted with sat.

aq. NH$_4$Cl solution (35 mL) and the layers were separated. The aqueous layer was extracted with CH$_2$Cl$_2$ (3×35 mL) and the combined organic extracts were washed with sat. aq. NaCl solution (50 mL), dried over MgSO$_4$ and concentrated in vacuo. Purification by flash column chromatography on silica (EtOAc/Hexanes=1:2) gel gave (Z)-olefin 5 as a pale yellow oil (11.27 g, 78%). [α]$_D^{r.t.}$=+45.2 (c=1, CHCl$_3$); R$_f$=0.40 (EtOAc/Hexanes=1:2); IR (film) ν$_{max}$ 2923, 2854, 1699, 1457, 1382, 1251, 1175, 1093, 1056, 850, 768 cm$^{-1}$; $^1$H NMR (250 MHz, CDCl$_3$) δ 5.27-5.40 (m, 2 H), 4.58 (br s, 1 H), 4.02 (dd, J=6.3, 8.8 Hz, 1 H), 3.61 (dd, J=3.3, 8.5 Hz, 1 H), 1.96 (br s, 2 H), 1.23-1.56 (m, 39H), 0.85 (t, J=7 Hz, 3 H); $^{13}$C NMR (101 MHz, CDCl$_3$) δ 152.1, 130.9, 130.4, 94.1, 79.8, 69.2, 54.7, 32.1, 29.9, 29.8, 29.8, 29.8, 29.7, 29.6, 29.5, 29.4, 28.6, 28.6, 27.6, 22.8, 14.2; HR ESI Calcd for C$_{26}$H$_{49}$NO$_3$ [M+Na$^+$]: 446.3605. found: 446.3614. All spectral data were in good accordance with reported data. [4].

The desired (Z)-olefin can easily be distinguished from the undesired (E)-olefin by-product, when considering the olefinic protons in the $^1$H NMR spectrum: Z-5 $^1$H NMR (250 MHz, CDCl$_3$) δ 4.05 (dd, J=6.3, 8.6 Hz, 1 H), 3.64 (dd, J=3.3, 8.6 Hz, 1 H) cf. E-5 $^1$H NMR (250 MHz, CDCl$_3$) δ4.01 (dd, J=6.1, 8.7 Hz, 1 H), 3.71 (dd, J=2.1, 8.7 Hz, 1 H).

Pentadecyltriphenylphosphonium Bromide

A solution of 1-bromopentadecane (30.0 g, 103 mmol) and triphenylphosphine (27.02 g, 103 mmol) in MeCN (200 mL) was refluxed at 80° C. for five days. After removal of the solvent in vacuo, Et$_2$O (30 mL) was added and the resulting white precipitate was filtered off, washed with Et$_2$O and dried on high vacuum for 24 h to give pentadecyltriphenylphosphonium bromide (49.66 g, 87%) as a white powder.

(2R,3Z)-2-(tert-Butoxycarbonyl)amino-3-octadecen-1-ol (5b)

Para-Toluensulfonic acid (371 mg, 1.95 mmol) was added to a stirred solution of (Z)-olefin 5 (5.00 g, 12.2 mmol) in MeOH/water (50 mL total, ratio=9:1 v/v) and the mixture was stirred for 68 h. The reaction mixture was concentrated in vacuo to yield a white solid, which was re-dissolved in CH$_2$Cl$_2$ (100 mL). The solution was washed with brine (30 mL), dried over MgSO$_4$ and the solvent was removed in vacuo. Purification by flash column chromatography on silica gel (gradient cyclohexane/EtOAc=4:1→2:1) afforded alcohol 5b as a white solid (2.71 g, 59%). All spectral data were in good accordance with reported data.

(2S,3S,4R)-2-(tert-Butoxycarbonyl)amino-1,3,4-octadecanetriol (6)

Alcohol 5b (1.50 g, 3.91 mmol) was dissolved in t-BuOH/water (38 mL total, ratio 1:1) and methanesulfonamide (371 mg, 3.91 mmol) was added. The reaction mixture was cooled to 0 C and AD-mix-β (5.48 g) was added. The resulting mixture was stirred at 0° C. for 41 h and another 7 h at r.t., then it was quenched by the addition of solid Na$_2$SO$_3$ (6.0 g) and left to stir for 30 min. Extraction with EtOAc (3×40 mL) followed. The organic extracts were washed with NaOH (1 M, 20 mL), water (20 mL) and sat. aq. NaCl solution (20 mL), dried over MgSO$_4$ and solvents were removed in vacuo. Purification by flash column chromatography on silica gel (gradient EtOAc/cyclohexane=1:1→2:1) provided triol 6 as a white solid (1.05 g, 64%).

Phytosphingosine (7)

Triol 6 (60 mg, 0.14 mmol) was dissolved in TFA (0.6 mL) and stirred at r.t. for 30 min. The solution was diluted with CH$_2$Cl$_2$ (1.5 mL) and then carefully neutralized (to pH ~8) with sat. aq. NaHCO$_3$ solution (10 mL) upon which precipitation of a white solid occurred. The white solid removed by filtration, washed with water (3×10 mL) and dried under reduced pressure. Recrystallization from MeCN yielded phytosphingosine 7 as a white powder (20 mg, 43%).

Ceramide (8)

To a solution of phytosphingosine 7 (15 mg, 0.047 mmol) in anhydrous THF (1 mL) was added hexacosanoic acid succinimidyl ester 11 (34 mg, 0.071 mmol) and Et$_3$N (24 µL, 0.14 mmol). The solution was heated to 50° C. and stirred for 20 h. EtOAc (5 mL) was added and the resulting suspension was centrifuged (30 min., 3000 rpm). The white precipitate was removed by filtration and dried under reduced pressure to yield amide 8 (29 mg, 88%).

Hexacosanoic N-Hydroxysuccinimidyl Ester (11)

To a solution of hexacosanoic acid (121 mg, 0.304 mmol) in CH$_2$Cl$_2$ (4 mL) were added 1-ethyl-3-(3-dimethylaminopropyl)carbodiimide (0.058 mL, 0.33 mmol) and N-hydroxysuccinimide (42 mg, 0.37 mmol). The reaction mixture was heated to 40° C., stirred for 3 h and then quenched with water (4 mL). The solution was diluted with Et$_2$O (8 mL) and the two layers were separated. The aqueous phase was extracted with Et$_2$O (8 mL) and the combined organic layers were washed with sat aq. NaCl solution (5 mL), dried over MgSO$_4$ and filtered. After removal of the solvent in vacuo, N-hydroxysuccinimidyl ester 11 was obtained as a white solid (85 mg, 57%).

(2S,3S,4R)-1,3,4-Tri-t-butyl-dimethylsilyloxy-2-hexacosanoylamino-1-octadecane (9)

To a stirred suspension of amide 8 (25 mg, 0.036 mmol) in CH$_2$Cl$_2$ (1.2 mL) was added TBSOTf (43 µL, 0.18 mmol) and 2,6-lutidine (65 µL, 0.054 mmol) at 0° C. The reaction mixture was stirred at r.t. for 2 h. The reaction was quenched with MeOH (0.2 mL). The mixture was diluted with Et$_2$O (2 mL) and washed with sat. aq. NaHCO$_3$ solution (1 mL) and sat. aq. NaCl solution (1 mL). The organic layer was dried over MgSO$_4$, filtered and concentrated under reduced pressure. The residue was purified by flash column chromatography on silica gel (cyclohexane/Et$_2$O=15:1) to give TBS protected ceramide 9 as a colorless oil (27 mg, 71%).

(2S,3S,4R)-3,4-Bis-tert-butyldimethylsilyloxy-2-hexacosanoylamino-4-octadecanol (10)

To a solution of ceramide 9 (90 mg, 0.087 mmol) in THF (2 mL) was added TFA (40 µL, 0.519 mmol) in water (0.5 mL, 27.8 mmol) at −10° C. The reaction mixture was left to warm to 10° C. over a period of 2 h. Then, the reaction mixture was quenched by the addition of sat. aq. NaHCO$_3$ solution until neutral pH was reached. The resulting mixture was diluted with Et$_2$O (10 mL), washed with water (10 mL), sat. aq. NaHCO$_3$ (10 mL), sat. aq. NaCl solution (10 mL), and dried over MgSO$_4$. The solvent was removed in vacuo and the crude product was purified by flash column chromatography on silica gel (gradient EtOAc/cyclohexane=10:1→5:1) to yield alcohol 10 (68 mg, 85%) as a colorless oil. [α]$_D^{r.t.}$=−11.6 (c=1, CHCl$_3$); R$_f$=0.3 (cyclohexane/EtOAc=4:1); IR (film) ν$_{max}$ 3285, 2920, 2851, 1645, 1465, 1253, 1034, 835, 776, 721, 680 cm$^{-1}$; $^1$H NMR (400 MHz, CDCl$_3$) δ 6.27 (d, J=7.8 Hz, 1H), 4.21 (dd, J=11.3, 3.0 Hz, 1H), 4.06 (td, J=6.5, 3.2 Hz, 1H), 3.91 (t, J=2.8 Hz, 1H), 3.76 (td, J=6.4, 2.6 Hz, 1H), 3.59 (dd, J=11.3, 3.7 Hz, 1H), 2.24-2.14 (m, 2H), 1.69-1.45 (m, 4H), 1.45-1.16 (m, 68H), 0.92 (s, 9H), 0.90 (s, 9H), 0.87 (t, J=6.9 Hz, 6H), 0.11 (s, 6H), 0.08 (s, 6H); $^{13}$C NMR (126 MHz, CDCl$_3$) δ 172.8, 77.6, 76.6, 63.8, 51.4, 37.1, 34.6, 32.1, 30.0, 29.9, 29.8, 29.7, 29.6, 29.5, 26.2, 26.1, 26.0, 25.8, 22.8, 18.3, 18.3, 14.3, -3.6, -3.9, -4.4, -4.8; HR ESI Calcd for C$_{56}$H$_{117}$NO$_4$Si$_2$ [M+Na$^+$]: 924.8594. found: 924.8604.

According to the synthetic procedure for compound 10 starting from compound 2 derivatives 10a to 10o were prepared accordingly using the respective triphenylphosphonium bromides in the reaction of compound 4 to compound 5 and the corresponding compounds 11 in the conversion of compounds 7 to compounds 8:

| comp. | structure | mass spec |
|---|---|---|
| 10a | 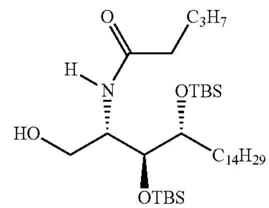 | C$_{35}$H$_{75}$NO$_4$Si$_2$<br>Calc.: 631.1544 [M + H$^+$]<br>Found: 631.1521 |
| 10b | 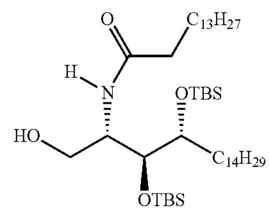 | C$_{45}$H$_{95}$NO$_4$Si$_2$<br>Calc.: 771.4206 [M + H$^+$]<br>Found: 771.4181 |
| 10c | 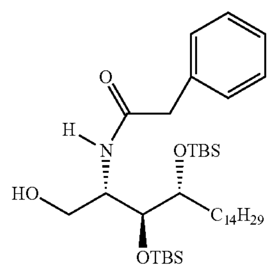 | C$_{38}$H$_{73}$NO$_4$Si$_2$<br>Calc.: 665.1707 [M + H$^+$]<br>Found: 665.1733 |
| 10d | 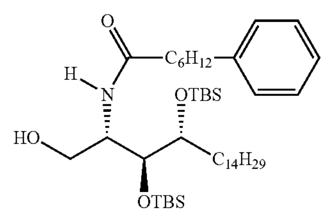 | C$_{43}$H$_{83}$NO$_4$Si$_2$<br>Calc.: 735.3038 [M + H$^+$]<br>Found: 735.3001 |
| 10e | 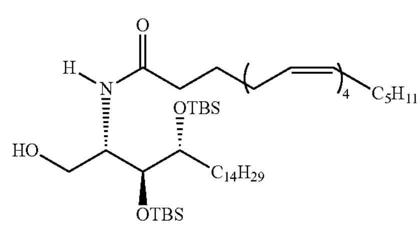 | C$_{50}$H$_{97}$NO$_4$Si$_2$<br>Calc.: 833.4901 [M + H$^+$]<br>Found: 833.4887 |
| 10f | 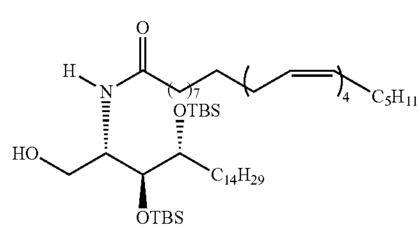 | C$_{56}$H$_{109}$NO$_4$Si$_2$<br>Calc.: 917.6498 [M + H$^+$]<br>Found: 917.6528 |

-continued
| comp. | structure | mass spec |
|---|---|---|
| 10g | 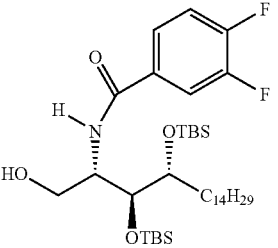 | C$_{37}$H$_{69}$F$_2$NO$_4$Si$_2$<br>Calc.: 687.1250 [M + H$^+$]<br>Found: 687.1212 |
| 10h | 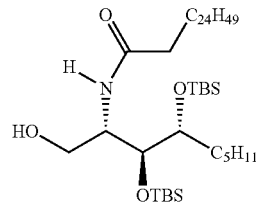 | C$_{47}$H$_{99}$NO$_4$Si$_2$<br>Calc.: 799.4738 [M + H$^+$]<br>Found: 799.4791 |
| 10i | 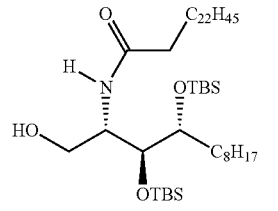 | C$_{48}$H$_{101}$NO$_4$Si$_2$<br>Calc.: 813.5004 [M + H$^+$]<br>Found: 813.4962 |
| 10j | 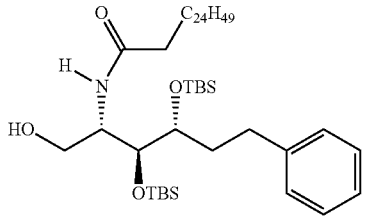 | C$_{50}$H$_{97}$NO$_4$Si$_2$<br>Calc.: 833.4901 [M + H$^+$]<br>Found: 833.4913 |
| 10k | 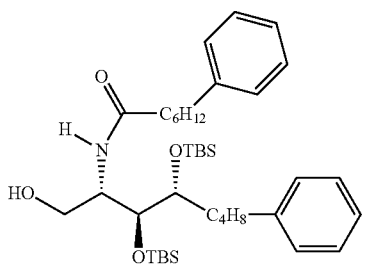 | C$_{39}$H$_{67}$NO$_4$Si$_2$<br>Calc.: 671.1338 [M + H$^+$]<br>Found: 671.1306 |
| 10l | 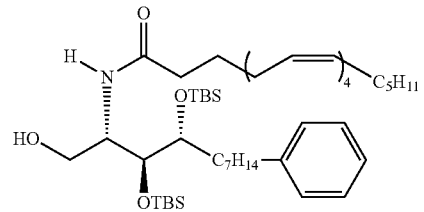 | C$_{49}$H$_{87}$NO$_4$Si$_2$<br>Calc.: 811.4000 [M + H$^+$]<br>Found: 811.4063 |

-continued

| comp. | structure | mass spec |
|---|---|---|
| 10m | 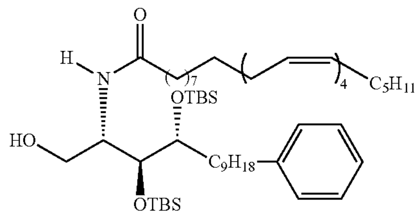 | $C_{57}H_{103}NO_4Si_2$<br>Calc.: 923.6129 [M + H$^+$]<br>Found: 923.6097 |
| 10n | 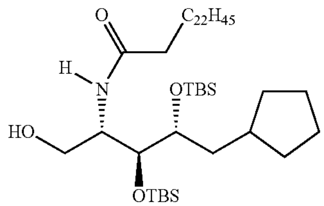 | $C_{46}H_{95}NO_4Si_2$<br>Calc.: 783.4313 [M + H$^+$]<br>Found: 783.4281 |
| 10o | 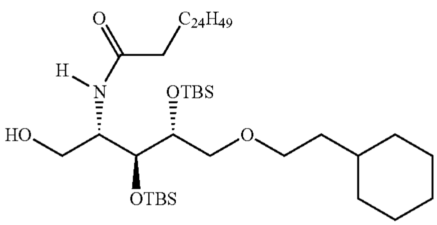 | $C_{51}H_{105}NO_5Si_2$<br>Calc.: 869.5638 [M + H$^+$]<br>Found: 869.5604 |

1-O-Allyl α-D-galactopyranoside (13)

To a stirred suspension of D-galactose 12 (22.2 g, 123 mmol) in allyl alcohol (250 mL) was added para-toluenesulfonic acid (2.3 g, 12.09 mmol). The mixture was heated to 100° C. and stirred for 24 h after which it was cooled to r.t. and quenched by the addition of NEt$_3$. The solvent was removed in vacuo and the crude product was co-evaporated twice with toluene and purified by flash column chromatography on silica gel (gradient CH$_2$Cl$_2$/MeOH=9:1→4:1). Recrystalization from EtOAc yielded galactoside 13 (22.2 g, 88%) as a white solid.

1-O-Allyl 6-O-trityl-α-D-galactopyranoside (14)

1-O-Allyl-galactoside 13 (4 g, 18.2 mmol) was dissolved in pyridine (18 mL). To the solution was added trityl chloride (6.58 g, 23.6 mmol) and the mixture was stirred at r.t. for 18 h after which the solvent was removed in vacuo. The crude product was purified by flash column chromatography on silica gel (CH$_2$Cl$_2$/MeOH=10:1) to yield pyranoside 14 (7.0 g, 83%) as colorless oil. [α]$_D^{r.t.}$=+60.0 (c=1, CHCl$_3$); R$_f$=0.8 (CH$_2$Cl$_2$/MeOH=5:1); IR (film) ν$_{max}$ 3402, 2929, 1491, 1449, 1218, 1152, 1070, 1032, 746, 703 cm$^{-1}$; $^1$H NMR (400 MHz, CDCl$_3$) δ 7.51-7.18 (m, 15H), 5.99-5.88 (m, 1H), 5.25 (ddq, J=35.9, 10.4, 1.4 Hz, 2H), 4.95 (d, J=3.8 Hz, 1H), 4.25 (ddt, J=12.8, 5.4, 1.4 Hz, 1H), 4.05 (ddt, J=12.8, 6.3, 1.3 Hz, 1H), 3.96 (s, 1H), 3.89 (t, J=5.8 Hz, 1H), 3.81 (d, J=5.7 Hz, 1H), 3.75 (d, J=9.8 Hz, 1H), 3.47 (s, 1H), 3.43 (dd, J=9.8, 6.1 Hz, 1H), 3.32 (dd, J=9.8, 5.3 Hz, 1H), 2.86 (d, J=2.1 Hz, 1H), 2.71 (d, J=8.1 Hz, 1H); $^{13}$C NMR (75 MHz, CDCl$_3$) δ 143.8, 133.7, 128.6, 127.8, 127.1, 117.8, 97.5, 86.9, 71.2, 69.8, 69.5, 69.5, 68.5, 63.3; HR ESI Calcd for C$_{25}$H$_{25}$O$_5$ [M+Na$^+$]: 485.1935. found: 485.1941.

1-O-Allyl 2,3,4-tri-O-benzyl-6-O-trityl-α-D-galactopyranoside (15)

To a solution of allyl 6-O-trityl-α/β-D-galactopyranoside 14 (3.7 g, 8.0 mmol) in DMF (32 mL) was added sodium hydride (60% in mineral oil, 1.50 g, 36.0 mmol) portionwise at r.t. After 1 h benzyl bromide (4.2 mL, 35.2 mmol) was added. The reaction mixture was left to stir for 48 h after which it was quenched by the addition of MeOH (5 mL). The mixture was diluted with Et$_2$O and extracted twice from sat. aq. NaHCO$_3$. The combined organic layer was washed with water (3×100 mL) and sat. aq. NaCl solution and dried over MgSO$_4$. The solvent was removed in vacuo and the crude product was over a plug of silica gel (hexanes/EtOAc=2:1, silica gel was neutralized with 1% NEt$_3$) to yield the benzyl ether 15 (5.5 g) as a pale yellow oil which was used in the subsequent step without further purification.

1-O-Allyl 2,3,4-tri-O-benzyl-α-D-galactopyranoside (16)

A solution of allyl 2,3,4-tri-O-benzyl-6-O-trityl-α-D-galactopyranoside 15 (5.00 g, 6.82 mmol) and triethyl silane (5.45 mL, 34.1 mmol) in CH$_2$Cl$_2$ (68 mL) was cooled to 0° C. To the stirred solution was added trifluoroacetic acid (2.6 mL, 34.1 mmol) dropwise. The mixture was quenched after 15 min. with sat. aq. NaHCO$_3$ solution and extracted with CH$_2$Cl$_2$. The crude product was filtered over a plug of silica gel. All silane and trityl residues were removed with 10:1 hexanes/EtOAc and the product was eluted with EtOAc to yield 16 (3.0 g) as a pale yellow oil which was used without further purification in the subsequent reaction.

1-O-Allyl 6-(6'-azidohexyl)-2,3,4-tri-O-benzyl-α-D-galactopyranoside (17)

To a solution of allyl 2,3,4-tri-O-benzyl-α-D-galactopyranoside 16 (1.0 g, 2.04 mmol) in DMF (10 mL) was added sodium hydride (60% in mineral oil, 0.12 g, 3.1 mmol) at 0° C. After 15 min, the mixture was warmed to r.t. and stirred for another 1 h. Then, 6-azidohexyl 4-methylbenzenesulfonate 23 (0.9 g, 3.1 mmol) was added and the reaction mixture was stirred at r.t. for a further 8 h after which the mixture was quenched by the addition of MeOH (2 mL). After dilution with $CH_2Cl_2$, sat. aq. $NH_4Cl$ solution was added and the mixture was extracted with $CH_2Cl_2$ (3×). The combined organic layer was washed with water and sat. aq. NaCl solution. The organic layer was dried over $MgSO_4$, the solvent was removed in vacuo and the crude product was purified by flash column chromatography on silica gel (gradient hexanes/EtOAc=1:0→1:1) to yield azide 17 (1.0 g, 68% over three steps) as a colorless oil. $[\alpha]_D^{r.t.}=+25.4$ (c=1, $CHCl_3$); $R_f$=0.65 (Hexanes/EtOAc=4:1); IR (film) $v_{max}$ 2933, 2863, 2094, 1497, 1454, 1358, 1177, 1098, 1059, 926, 816, 736, 697 $cm^{-1}$; $^1H$ NMR (400 MHz, $CDCl_3$) δ 7.94-7.16 (m, 15H), 5.95 (dddd, J=17.1, 10.3, 6.6, 5.2 Hz, 1H), 5.31 (dq, J=17.2, 1.6 Hz, 1H), 5.21 (ddd, J=10.3, 2.8, 1.1 Hz, 1H), 5.01-4.58 (m, 7H), 4.17 (ddt, J=13.0, 5.2, 1.4 Hz, 1H), 4.09-3.99 (m, 3H), 3.98-3.90 (m, 2H), 3.50-3.18 (m, 6H), 1.72-1.47 (m, 4H), 1.44-1.30 (m, 4H); $^{13}C$ NMR (75 MHz, $CDCl_3$) δ 138.9, 138.8, 138.6, 134.0, 129.8, 128.3, 128.3, 128.2, 128.1, 128.0, 127.9, 127.6, 127.5, 127.4, 117.9, 96.3, 79.1, 76.5, 75.3, 74.7, 73.3, 73.3, 71.3, 70.3, 69.5, 69.4, 68.2, 51.4, 51.2, 29.6, 28.8, 28.7, 28.6, 26.6, 26.1, 25.7, 25.0, 21.6. HR ESI Calcd for $C_{36}H_{45}N_3O_6$ [M+Na$^+$]: 638.3201. found: 638.3229.

The below compounds were prepared according to the synthetic procedure above with the corresponding compounds 23 in moderate to high yields:

| comp. | structure | mass spec |
|---|---|---|
| 17a | 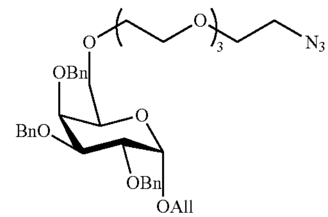 | $C_{38}H_{50}N_3O_9$<br>Calc.: 693.8278 [M + H$^+$]<br>Found: 693.8241 |
| 17b | 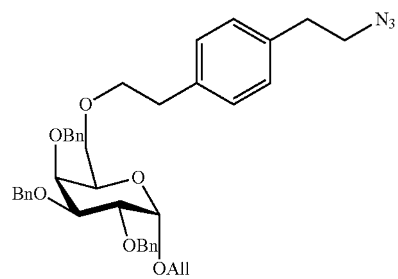 | $C_{36}H_{46}N_3O_6$<br>Calc.: 617.7764 [M + H$^+$]<br>Found: 617.7721 |
| 17c | 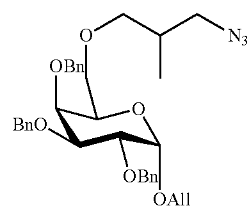 | $C_{34}H_{42}N_3O_6$<br>Calc.: 589.7231 [M + H$^+$]<br>Found: 589.7274 |
| 17d | 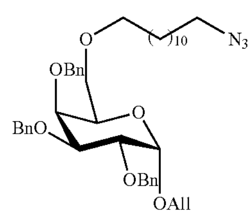 | $C_{42}H_{58}N_3O_6$<br>Calc.: 701.9361 [M + H$^+$]<br>Found: 701.9400 |
| 17e | 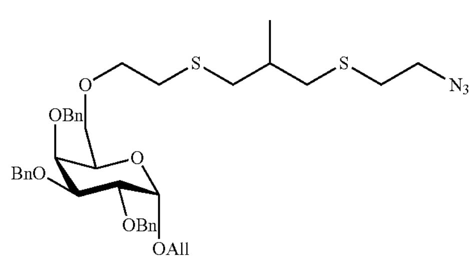 | $C_{38}H_{50}N_3S_2O_6$<br>Calc.: 709.9618 [M + H$^+$]<br>Found: 709.9651 |

| comp. | structure | mass spec |
|---|---|---|
| 17f | (galactopyranose with OBn, BnO, OBn, OAll and O-CH2-S-S-CH2CH2-N3) | $C_{32}H_{38}N_3S_2O_6$<br>Calc.: 625.8021 [M + H$^+$]<br>Found: 625.7996 |

6-(6'-Azidohexyl)-2,3,4-tri-O-benzyl-α/β-D-galactopyranose (18)

Allyl 6-(6'-azidohexyl)-2,3,4-tri-O-benzyl-α-D-galactopyranoside 17 (1.4 g, 2.3 mmol) was dissolved in MeOH (16 mL) and PdCl$_2$ (0.21 g, 1.17 mmol) was added to the solution at r.t. The mixture was stirred at for 4 h after which the mixture was filtered over celite and the solvent was removed in vacuo. The crude product was purified by flash column chromatography (gradient hexanes/EtOAc=1:0→1:1) to yield lactol 18 (1.2 g, 88%) as a colorless oil. R$_f$=0.50 (Hexanes/EtOAc=2:1); IR (film) ν$_{max}$ 3414, 2933, 2862, 2093, 1454, 1255, 1060, 910, 733, 696 cm$^{-1}$; $^1$H NMR (400 MHz, CDCl$_3$) δ 7.45-7.20 (m, 30H), 5.33-5.27 (m, 1H), 5.01-4.90 (m, 3H), 4.85-4.71 (m, 7H), 4.66 (ddd, J=16.7, 11.5, 6.0 Hz, 3H), 4.18-4.09 (m, 1H), 4.05 (dd, J=9.2, 3.6 Hz, 1H), 3.96 (s, 2H), 3.93 (d, J=2.8 Hz, 1H), 3.88 (d, J=2.8 Hz, 1H), 3.78 (dd, J=9.6, 7.5 Hz, 1H), 3.63-3.52 (m, 3H), 3.52-3.37 (m, 5H), 3.37-3.28 (m, 2H), 3.28-3.21 (m, 5H), 1.65-1.49 (m, 8H), 1.42-1.24 (m, 8H); $^{13}$C NMR (101 MHz, CDCl$_3$) δ 138.8, 138.7, 138.5, 138.4, 128.5, 128.5, 128.4, 128.3, 128.3, 128.3, 128.3, 128.1, 127.9, 127.7, 127.7, 127.7, 127.6, 127.6, 97.9, 92.0, 82.3, 80.9, 78.8, 76.7, 75.2, 74.9, 74.8, 74.7, 73.8, 73.7, 73.6, 73.1, 73.1, 71.5, 71.4, 69.6, 69.6, 69.5, 51.5, 29.5, 28.9, 26.6, 25.8; HR ESI Calcd for $C_{33}H_{41}N_3O_6$ [M+Na$^+$]: 598.2883. found: 598.2869.

The below compounds were prepared according to the synthetic procedure above with the corresponding compounds 17 in average good yields:

| comp. | structure | mass spec |
|---|---|---|
| 18a | (galactopyranose with OBn, BnO, OBn, OH and O-(CH2CH2O)3-CH2CH2-N3) | $C_{35}H_{46}N_3O_9$<br>Calc.: 653.7638 [M + H$^+$]<br>Found: 653.7601 |
| 18b | (galactopyranose with OBn, BnO, OBn, OH and O-CH2CH2-C6H4-CH2CH2-N3) | $C_{33}H_{42}N_3O_6$<br>Calc.: 577.7124 [M + H$^+$]<br>Found: 577.7193 |
| 18c | (galactopyranose with OBn, BnO, OBn, OH and O-CH2-CH(CH3)-CH2-N3) | $C_{31}H_{38}N_3O_6$<br>Calc.: 549.6592 [M + H$^+$]<br>Found: 549.6556 |
| 18d | (galactopyranose with OBn, BnO, OBn, OH and O-(CH2)10-CH2CH2-N3) | $C_{39}H_{54}N_3O_6$<br>Calc.: 661.8721 [M + H$^+$]<br>Found: 661.8791 |

-continued

| comp. | structure | mass spec |
|---|---|---|
| 18e | (structure: 2,3,4-tri-O-benzyl-galactopyranose with 6-O-CH₂CH₂-S-CH₂-CH(CH₃)-CH₂-S-CH₂CH₂-N₃) | $C_{35}H_{46}N_3S_2O_6$<br>Calc.: 669.8978 [M + H⁺]<br>Found: 669.9003 |
| 18f | (structure: 2,3,4-tri-O-benzyl-galactopyranose with 6-O-CH₂-S-S-CH₂-N₃) | $C_{29}H_{34}N_3S_2O_6$<br>Calc.: 585.7381 [M + H⁺]<br>Found: 585.7323 |

6-(6'-Azidohexyl)-2,3,4-tri-O-benzyl-β-D-galactopyranosyl N-phenyl trifluoroacetimidate (19)

To a solution of 6-(6'-azidohexyl)-2,3,4-tri-O-benzyl-α/β-D-galactopyranose 18 (400 mg, 0.70 mmol) in CH₂Cl₂ (7 mL) was added cesium carbonate (340 mg, 1.04 mmol). To the mixture was added 2,2,2-trifluoro-N-phenylacetimidoyl chloride 24 (216 mg, 1.04 mmol) and the reaction mixture was stirred at r.t. for 3.5 h after which it was filtered over celite and washed with CH₂Cl₂. The solvent was removed in vacuo and the crude product was purified by flash column chromatography on silica gel (gradient hexanes/EtOAc=10:1→1:1) to yield the imidate 19 (490 mg, 94%) as a colorless oil. $[\alpha]_D^{r.t.}$=+60.8 (c=0.4, CHCl₃); $R_f$=0.80 (Hexanes/EtOAc=2:1); IR (film) $v_{max}$ 3064, 2934, 2865, 2094, 1717, 1598, 1454, 1321, 1207, 1099, 1027, 910, 734, 696 cm⁻¹; ¹H NMR (400 MHz, CDCl₃) δ 7.45-6.60 (m, 20H), 5.56 (s, 1H), 4.90 (d, J=11.5 Hz, 1H), 4.75 (s, J=1.5 Hz, 2H), 4.68 (s, J=12.4 Hz, 2H), 4.58 (d, J=11.6 Hz, 1H), 4.00 (t, J=8.7 Hz, 1H), 3.84 (d, J=2.4 Hz, 1H), 3.58-3.39 (m, 4H), 3.34 (dt, J=9.3, 6.5 Hz, 1H), 3.23 (dt, J=9.3, 6.5 Hz, 1H), 3.14 (t, J=6.9 Hz, 2H), 1.52-1.38 (m, 4H), 1.32-1.16 (m, 4H); ¹³C NMR (101 MHz, CDCl₃) δ 138.6, 138.3, 138.2, 128.8, 128.6, 128.5, 128.4, 128.4, 128.3, 128.0, 127.9, 127.8, 127.7, 124.3, 119.4, 82.3, 78.3, 77.4, 77.2, 76.8, 75.7, 74.9, 74.6, 73.4, 73.2, 71.4, 68.7, 51.5, 29.7, 28.9, 26.7, 25.8; HR ESI Calcd for $C_{41}H_{45}F_3N_4O_6$ [M+Na⁺]: 769.3183. found: 769.3239.

The below compounds were prepared according to the synthetic procedure above with the corresponding compounds 18 in average moderate to good yields:

| comp. | structure | mass spec |
|---|---|---|
| 19a | (structure: 2,3,4-tri-O-benzyl-galactopyranosyl N-phenyl trifluoroacetimidate with 6-O-(CH₂CH₂O)₃-CH₂CH₂-N₃) | $C_{43}H_{50}F_3N_4O_9$<br>Calc.: 824.8834 [M + H⁺]<br>Found: 824.8804 |
| 19b | (structure: 2,3,4-tri-O-benzyl-galactopyranosyl N-phenyl trifluoroacetimidate with 6-O-CH₂CH₂-C₆H₄-CH₂CH₂-N₃) | $C_{41}H_{46}F_3N_4O_6$<br>Calc.: 748.8320 [M + H⁺]<br>Found: 748.8299 |

| comp. | structure | mass spec |
|---|---|---|
| 19c | 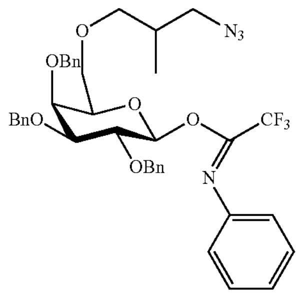 | $C_{39}H_{42}F_3N_4O_6$<br>Calc.: 720.7788 [M + H$^+$]<br>Found: 720.7712 |
| 19d | 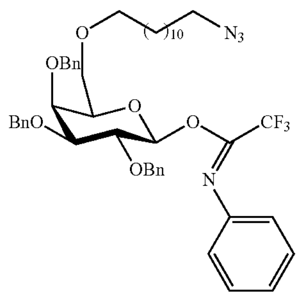 | $C_{47}H_{58}F_3N_4O_6$<br>Calc.: 832.9917 [M + H$^+$]<br>Found: 832.9977 |
| 19e | 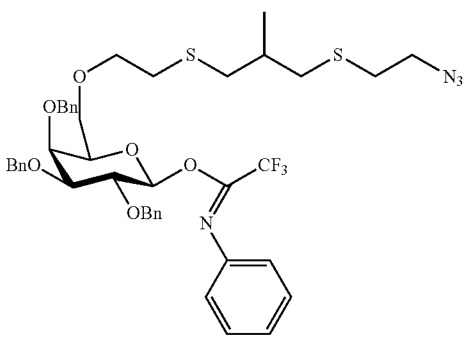 | $C_{43}H_{50}F_3N_4S_2O_6$<br>Calc.: 841.0174 [M + H$^+$]<br>Found: 841.0108 |
| 19f | 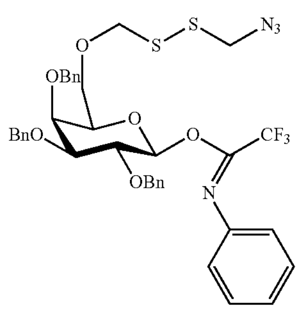 | $C_{37}H_{38}F_3N_4S_2O_6$<br>Calc.: 756.8577 [M + H$^+$]<br>Found: 756.8506 |

6-Hydroxyhexyl 4-methylbenzenesulfonate (21)

To a solution of hexane-1,6-diol 20 (10.0 g, 85 mmol) in CH$_2$Cl$_2$ (200 mL) was added 4-methylbenzene-1-sulfonyl chloride (17.8 g, 93 mmol) dissolved in pyridine (100 mL) at 5° C. dropwise over 15 min. The reaction mixture was warmed to r.t. over the period of 5 h. Solvents were removed in vacuo and the crude was purified by silica flash column chromatography (gradient hexanes/EtOAc=1:0→1:1) to afford monotosylated hexanediol 21 (6.5 g, 28%) as a colorless oil. R$_f$=0.55 (Hexanes/EtOAc=1:1); IR (film) ν$_{max}$ 3381, 2935, 2862, 1598, 1461, 1352, 1172, 959, 921, 813, 661 cm$^{-1}$; $^1$H NMR (400 MHz, CDCl$_3$) δ 7.76-7.71 (m, 2H), 7.29 (dt, J=4.3, 1.2 Hz, 2H), 3.97 (t, J=6.5 Hz, 2H), 3.55 (t, J=6.5 Hz, 2H), 2.40 (s, 3H), 1.65-1.56 (m, 2H), 1.55 (s, 1H), 1.52-1.41 (m, 2H), 1.36-1.18 (m, 4H); $^{13}$C NMR (101 MHz, CDCl$_3$) δ 144.7, 133.1, 129.8, 127.8, 70.5, 62.6, 32.4, 28.7, 25.1, 25.0, 21.6; HR ESI Calcd for C$_{13}$H$_{20}$O$_4$S [M+Na$^+$]: 295.0975. found: 295.0968.

6-Azidohexan-1-ol (22)

6-Hydroxyhexyl 4-methylbenzenesulfonate 21 (4.3 g, 15.79 mmol) was dissolved in DMF (23 mL) and sodium azide (1.75 g, 26.8 mmol) was added. The mixture was heated to 55° C. and after 16 h it was cooled to r.t. and diluted with water (150 mL). The mixture was extracted three times with $CH_2Cl_2$ and washed with sat. aq. NaCl solution. The organic layer was dried over $MgSO_4$ and solvents were removed in vacuo. The crude product was purified by silica flash column chromatography on silica gel (gradient hexanes/EtOAc=1:0→1:1) to afford 6-azidohexan-1-ol 22 (2.2 g, 97%) as a colorless oil. $R_f$=0.50 (Hexanes/EtOAc=2:1); IR (film) $v_{max}$ 3329, 2935, 2891, 2090, 1256, 1349, 1258, 1055, 910, 731 $cm^{-1}$; $^1H$ NMR (400 MHz, $CDCl_3$) δ 3.63 (t, J=6.5 Hz, 2H), 3.25 (t, J=6.9 Hz, 2H), 1.64-1.51 (m, 4H), 1.43-1.32 (m, 4H); $^{13}C$ NMR (101 MHz, $CDCl_3$) δ2.8, 51.5, 32.6, 28.9, 26.6, 25.4; HR ESI Calcd for $C_6H_{13}N_3O[M+Na^+]$: 166.0951 found: 166.0945.

6-Azidohexyl 4-methylbenzenesulfonate (23)

To a solution of 6-azidohexan-1-ol 22 (2.7 g, 18.9 mmol) in pyridine (70 mL) was added 4-methylbenzene-1-sulfonyl chloride (4.0 g, 21.0 mmol). The reaction mixture was left to stir for 5 h at r.t. after which the solvent was removed in vacuo and the crude product was dissolved in $CH_2Cl_2$, washed with water and dried over $MgSO_4$. Solvents were removed in vacuo and the crude product was purified by silica flash column chromatography on silica gel (gradient hexanes/EtOAc=1:0→1:1) to afford azide 23 (5.0 g, 89%) as a colorless oil. $R_f$=0.50 (Hexanes/EtOAc=3:1); IR (film) $v_{max}$ 2938, 2863, 2092, 1598, 1455, 1356, 1258, 1174, 1097, 956, 919, 813, 724, 662 $cm^{-1}$; $^1H$ NMR (400 MHz, $CDCl_3$) δ; 7.85-7.67 (m, 2H), 7.33 (dd, J=8.5, 0.6 Hz, 2H), 4.01 (t, J=6.4 Hz, 2H), 3.21 (t, J=6.9 Hz, 2H), 2.43 (s, 3H), 1.71-1.57 (m, 2H), 1.52 (dd, J=9.1, 4.9 Hz, 2H), 1.38-1.12 (m, 4H); $^{13}C$ NMR (101 MHz, $CDCl_3$) δ 144.8, 133.2, 129.9, 127.9, 70.4, 51.3, 28.7, 28.7, 26.1, 25.0, 21.7; HR ESI Calcd for $C_{13}H_{19}N_3O_3S$ [$M+Na^+$]: 320.1045. found: 320.1057.

According to the synthetic route set forth above for compounds 20 to compounds 23 various starting materials have been tried out and successfully converted to corresponding compounds 23. For these syntheses Tetraethylenglycol was purchased at Merck, Germany; 2-(4-(2-hydroxyeth-1-yl)phenyl)ethanol was purchased at Sigma Aldrich; 2-methyl-1,3-propanol was purchased at Sigma Aldrich; dodecandiol was purchased by Sigma Aldrich; 2-Methypropane-1,3-bis(2-hydroxyethysulfide) was prepared according to the procedure disclosed in US2012/0295228.

| comp. | structure | mass spec |
|---|---|---|
| 23a | TsO-(-O-)₃-N₃ | $C_{15}H_{23}N_3SO_6$ Calc.: 374.4344 [M + H⁺] Found: 374.4388 |
| 23b | TsO-CH₂CH₂-C₆H₄-CH₂CH₂-N₃ | $C_{17}H_{19}N_3SO_3$ Calc.: 346.4259 [M + H⁺] Found: 346.4212 |
| 23c | TsO-CH₂-CH(CH₃)-CH₂-N₃ | $C_{11}H_{15}N_3SO_3$ Calc.: 270.3297 [M + H⁺] Found: 270.3229 |
| 23d | TsO-(CH₂)₆-N₃ (extended chain) | $C_{19}H_{31}N_3SO_3$ Calc.: 382.5426 [M + H⁺] Found: 382.5461 |
| 23e | TsO-CH₂CH₂-S-CH₂-CH(CH₃)-CH₂-S-CH₂CH₂-N₃ | $C_{15}H_{23}N_3S_3O_3$ Calc.: 390.5683 [M + H⁺] Found: 390.5662 |
| 23f | TsO-CH₂-S-S-CH₂CH₂-N₃ | $C_9H_{11}N_3S_3O_3$ Calc.: 306.4086 [M + H⁺] Found: 306.4041 |

(2S,3S,4R)-3,4-Bis-tert-butyldimethylsilyloxy-2-hexacosanoylamino-1-(6-(6'-azidohexyl)-2,3,4-tri-O-benzyl)-α-D-galactopyranosyl)octadecane (25)

Nucleophile 10 (156 mg, 0.169 mmol) and glycosylating agent 19 (189 mg, 0.253 mmol) were co-evaporated with toluene three times and dried on high vacuum for 3 h after which they were dissolved in $Et_2O$ (2 mL) and THF (0.4 mL) and cooled to -40° C. To the mixture was added TMSOTf (9.0 μL, 0.051 mmol) and the solution was warmed to -10° C. over the period of 3 h. The reaction was quenched by the addition of $NEt_3$ (0.05 mL) and solvents were removed in vacuo and the crude product was purified by silica flash column chromatography (gradient hexanes/EtOAc=10:1→4:1) to afford glycoside 25 (180 mg, 72% α-anomer) as a white foam. $[\alpha]_D^{r.t.}$=+18.9 (c=1, $CHCl_3$); $R_f$=0.46 (Hexanes/EtOAc=6.5:1); IR (film) $v_{max}$ 3328, 2925, 2854, 2096, 1731, 1656, 1452, 1348, 1246, 1156, 1099, 1058, 835, 777, 696 $cm^{-1}$; $^1H$ NMR (400 MHz, $CDCl_3$) δ 7.64-7.09 (m, 15H), 6.07 (d, J=7.1 Hz, 1H), 4.94 (d, J=11.5 Hz, 1H), 4.82 (d, J=3.7 Hz, 1H), 4.80-4.56 (m, 5H), 4.09 (td, J=7.6, 4.2 Hz, 1H), 4.03 (dd, J=10.1, 3.6 Hz, 1H), 3.97-3.85 (m, 5H), 3.82 (dd, J=10.9, 8.2 Hz, 1H), 3.66-3.61 (m, 1H), 3.50-3.42 (m, 1H), 3.38 (ddd, J=13.6, 8.1, 6.2 Hz, 2H), 3.29 (dt, J=9.4, 6.8 Hz, 1H), 3.22 (t, J=6.9 Hz, 2H), 1.99 (dd, J=16.6, 9.2 Hz, 2H), 1.60-1.45 (m, 8H), 1.39-1.15 (m, 70H), 0.91-0.84 (m, 26H), 0.06 (s, 3H), 0.05 (s, 3H), 0.02 (s, 6H). $^{13}$C NMR (101 MHz, CDCl$_3$) δ 173.2, 138.6, 138.5, 138.0, 128.6, 128.6, 128.4, 128.3, 128.3, 128.1, 127.8, 127.8, 127.6, 99.3, 79.5, 76.4, 76.2, 74.9, 74.6, 74.4, 73.5, 72.9, 71.56, 70.1, 70.0, 69.4, 51.5, 49.6, 36.9, 33.5, 32.1, 29.9, 29.8, 29.7, 29.6, 29.6, 29.5, 29.5, 28.9, 26.7, 26.1, 25.9, 25.9, 22.8, 14.3; HR ESI Calcd for C$_{89}$H$_{156}$N$_4$O$_9$Si$_2$ [M+Na$^+$]: 1505.1333. found: 1505.1388.

The below compounds 25c-h were prepared according to the synthetic procedure above with the corresponding compounds 10 and 19 in average moderate to good yields:

| comp. | structure | mass spec |
|---|---|---|
| 25c | 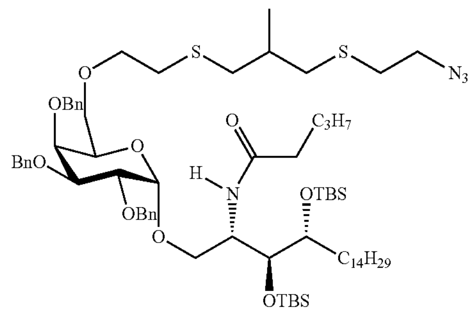 | C$_{70}$H$_{119}$N$_4$O$_9$S$_2$Si$_2$<br>Calc.: 1282.0290 [M + H$^+$]<br>Found: 1282.0317 |
| 25d | 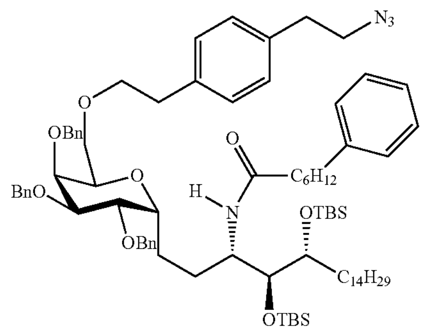 | C$_{76}$H$_{123}$N$_4$O$_9$Si$_2$<br>Calc.: 1293.9930 [M + H$^+$]<br>Found: 1293.9903 |
| 25e | 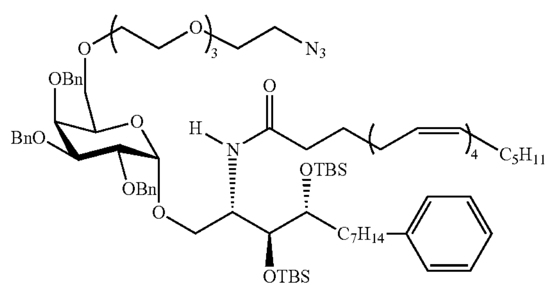 | C$_{84}$H$_{131}$N$_4$O$_{12}$Si$_2$<br>Calc.: 1446.1406 [M + H$^+$]<br>Found: 1446.1458 |
| 25f | 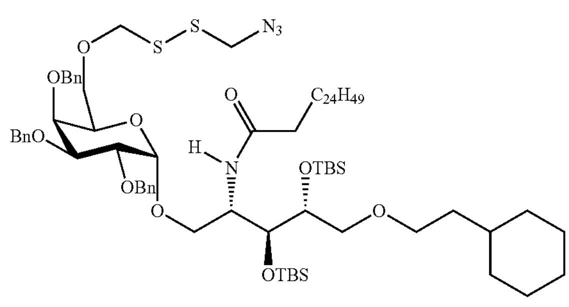 | C$_{80}$H$_{137}$N$_4$O$_{10}$S$_2$Si$_2$<br>Calc.: 1436.2787 [M + H$^+$]<br>Found: 1436.2744 |

| comp. | structure | mass spec |
|---|---|---|
| 25g | 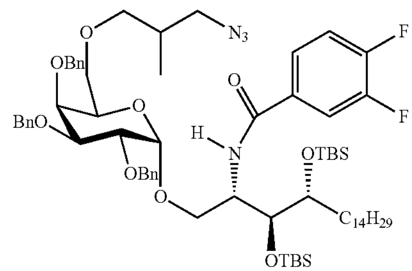 | $C_{68}H_{105}F_2N_4O_9Si_2$<br>Calc.: 1217.7610 [M + H$^+$]<br>Found: 1217.7588 |
| 25h | 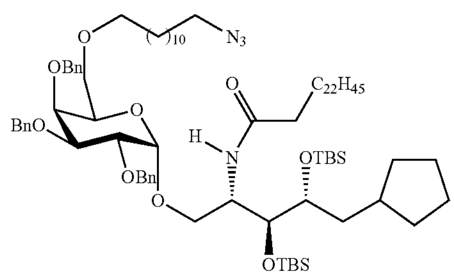 | $C_{85}H_{147}N_4O_9Si_2$<br>Calc.: 1426.2802 [M + H$^+$]<br>Found: 1426.2826 |

(2S,3S,4R)-2-Hexacosanoylamino-1-(6-(6'-azido-hexyl)-2,3,4-tri-O-benzyl-α-D-galactopyranosyl) octadecane-3,4-diol (26)

To a solution of bis-TBS ether 25 (16.0 mg, 10.8 μmol) in THF (1 mL) was added a solution of TBAF (1 M in THF, 0.150 mL, 0.15 mmol) slowly. After 3.5 h the reaction mixture was diluted with CH$_2$Cl$_2$ (10 mL). Solvents were removed in vacuo and crude product was purified by silica flash column chromatography (gradient hexanes/EtOAc=1: 0→1:1) to afford diol 26 (10.5 mg, 78%) as a clear oil. [α]$_D^{r.t.}$=+121.9 (c=0.2, CHCl$_3$); R$_f$=0.40 (Hexanes/EtOAc=2:1); IR (film) ν$_{max}$ 3329, 2919, 2851, 2096, 1640, 1543, 1467, 1455, 1350, 1094, 1046, 907, 730, 696 cm$^{-1}$; $^1$H NMR (400 MHz, CDCl$_3$) δ 7.58-7.08 (m, 15H), 6.37 (d, J=8.4 Hz, 1H), 4.94 (d, J=11.4 Hz, 1H), 4.88 (d, J=11.6 Hz, 1H), 4.85 (d, J=3.8 Hz, 1H), 4.82-4.73 (m, 2H), 4.68 (d, J=11.6 Hz, 1H), 4.60 (d, J=11.5 Hz, 1H), 4.22 (dq, J=6.8, 3.3 Hz, 1H), 4.05 (dd, J=10.0, 3.8 Hz, 1H), 3.95 (d, J=1.8 Hz, 1H), 3.88 (d, J=2.7 Hz, 2H), 3.87-3.75 (m, 2H), 3.55-3.36 (m, 5H), 3.31 (dt, J=9.4, 6.7 Hz, 1H), 3.25 (t, J=6.9 Hz, 2H), 2.20-2.11 (m, 3H), 1.70-1.44 (m, 8H), 1.41-1.17 (m, 73H), 0.88 (t, J=6.9 Hz, 6H); $^{13}$C NMR (101 MHz, CDCl$_3$) δ 173.2, 138.6, 138.5, 130.0, 128.6, 128.6, 128.4, 128.3, 128.2, 128.1, 127.8, 127.8, 127.6, 99.3, 79.5, 76.4, 76.2, 74.9, 74.6, 74.4, 73.5, 72.9, 71.6, 70.1, 70.0, 69.4, 51.5, 49.6, 36.9, 33.5, 32.1, 29.9, 29.8, 29.7, 29.6, 29.6, 29.5, 29.5, 28.9, 26.7, 26.1, 25.9, 25.9, 22.8, 14.3; HR ESI Calcd for C$_{77}$H$_{128}$N$_4$O$_9$ [M+Na$^+$]: 1275.9574. found: 1275.9536.

The below compounds 26c-h were prepared according to the synthetic procedure above for compound 26 in average moderate to good yields:

| comp. | structure | mass spec |
|---|---|---|
| 26c | 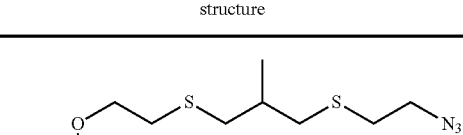 | $C_{58}H_{91}N_4O_9S_2$<br>Calc.: 1053.5070 [M + H$^+$]<br>Found: 1053.5046 |

-continued

| comp. | structure | mass spec |
|---|---|---|
| 26d | 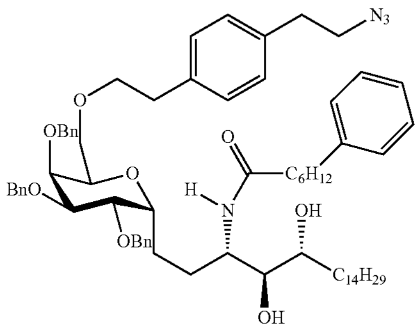 | C₆₄H₉₅N₄O₉<br>Calc.: 1065.4710 [M + H⁺]<br>Found: 1065.4677 |
| 26e | 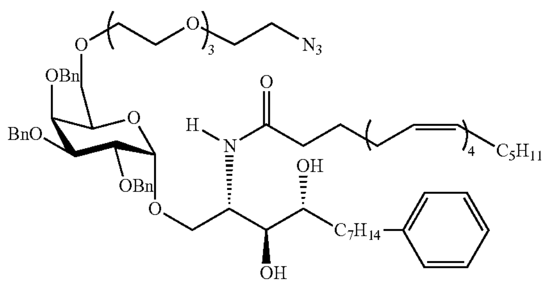 | C₇₂H₁₀₃N₄O₁₂<br>Calc.: 1217.6187 [M + H⁺]<br>Found: 1217.6203 |
| 26f | 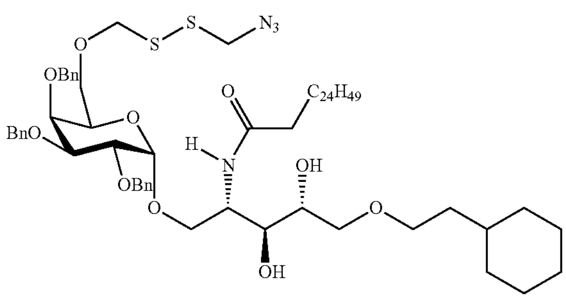 | C₆₈H₁₀₉N₄O₁₀S₂<br>Calc.: 1207.7567 [M + H⁺]<br>Found: 1207.7532 |
| 26g | 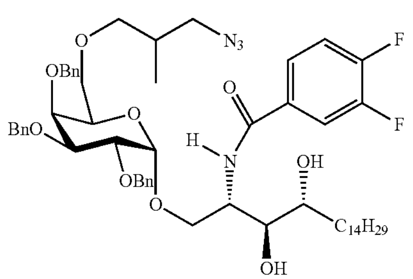 | C₅₆H₇₇F₂N₄O₉<br>Calc.: 989.2390 [M + H⁺]<br>Found: 989.2371 |
| 26h | 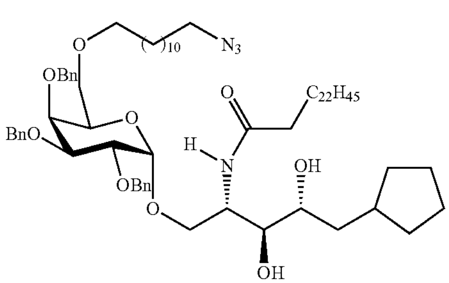 | C₇₃H₁₁₉N₄O₉<br>Calc.: 1197.7582 [M + H⁺]<br>Found: 1197.7614 |

(2S,3S,4R)-1-(6-(6'-Aminohexyl)-α-D-galactopyranosyl)-2-hexacosanoylaminooctadecane-3,4-diol (27)

To a solution diol 26 (55 mg, 0.044 mmol) in EtOH (0.5 mL) and chloroform (0.15 mL) was added Pd(OH)$_2$ on charcoal (10% w/w, wet 38 mg). The solution was stirred at r.t. under an atmosphere of Ar for 15 min. after which H$_2$ gas was inserted into the suspension and the mixture was hydrogenated for 12 h. The mixture was filtered over celite and thoroughly washed with CH$_2$Cl$_2$, THF and MeOH. Solvents were removed in vacuo and the crude was purified by silica flash column chromatography on silica gel (CH$_2$Cl$_2$/MeOH=4:1) to afford linker equipped GSL 27 (38 mg, 90%) as a pale yellow powder. $[\alpha]_D^{r.t.}$=+66.1 (c=1.0, Pyridine); R$_f$=0.44 (CH$_2$Cl$_2$/MeOH=4:1); IR (film) $\nu_{max}$ 3292, 2918, 2850, 1640, 1539, 1468, 1304, 1073, 1038, 970, 721 cm$^{-1}$; $^1$H NMR (400 MHz, d-pyr) δ 8.66 (d, J=8.6 Hz, 1H), 5.48 (d, J=3.8 Hz, 1H), 4.59 (dd, J=10.6, 5.9 Hz, 1H), 4.49 (dd, J=9.7, 3.8 Hz, 1H), 4.39-4.15 (m, 1H), 3.91 (ddd, J=15.3, 10.4, 5.9 Hz, 1H), 3.74 (q, J=7.0 Hz, 1H), 3.44-3.31 (m, 2H), 3.17 (dd, J=13.1, 5.2 Hz, 2H), 2.42 (t, J=6.6 Hz, 2H), 2.17 (s, 1H), 1.89 (s, 2H), 1.84-1.65 (m, 4H), 1.65-0.97 (m, 75H), 0.75 (t, J=6.7 Hz, 6H); $^{13}$C NMR (101 MHz, d-pyr) δ 171.9, 99.7, 75.5, 70.9, 70.1, 70.0, 69.6, 68.7, 66.7, 55.9, 49.9, 38.4, 35.4, 33.1, 30.7, 30.7, 29.0, 28.8, 28.6, 28.6, 28.6, 28.6, 28.5, 28.5, 28.4, 28.4, 28.2, 28.2, 26.8, 25.3, 25.1, 25.1, 24.7, 21.5, 17.8, 12.9; HR ESI Calcd for C$_{56}$H$_{112}$N$_2$O$_9$ [M+H$^+$]: 957.8441. found: 957.8468.

The below compounds 26c-h were prepared according to the synthetic procedure above for compound 27 in average moderate to good yields:

| comp. | structure | mass spec |
|---|---|---|
| 27c | 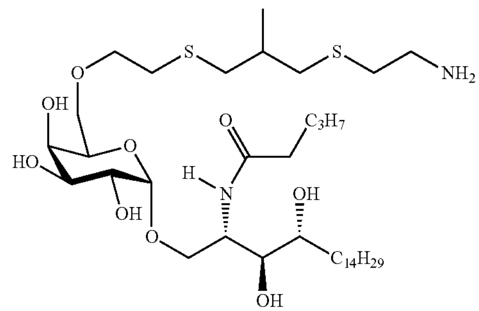 | C$_{37}$H$_{75}$N$_2$O$_9$S$_2$<br>Calc.: 757.1410 [M + H$^+$]<br>Found: 757.1437 |
| 27d | 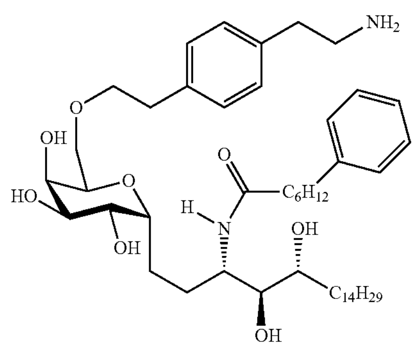 | C$_{43}$H$_{79}$N$_2$O$_9$<br>Calc.: 769.1050 [M + H$^+$]<br>Found: 769.1078 |
| 27e | 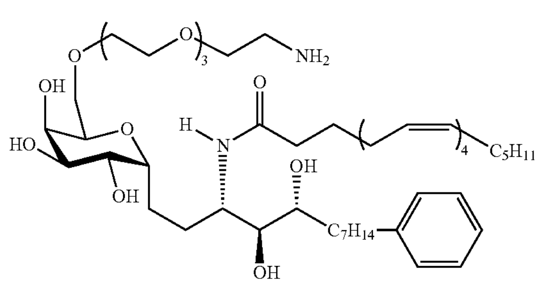 | C$_{51}$H$_{87}$N$_2$O$_{12}$<br>Calc.: 921.2527 [M + H$^+$]<br>Found: 921.2500 |

-continued

| comp. | structure | mass spec |
|---|---|---|
| 27f | 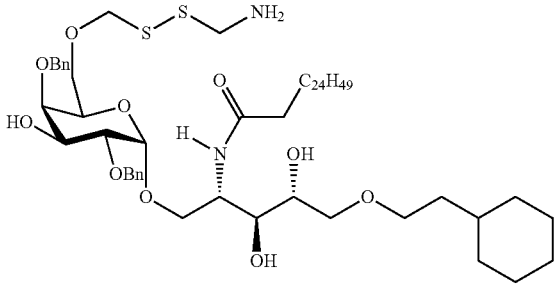 | $C_{47}H_{93}N_2O_{10}S_2$<br>Calc.: 911.3907 [M + H$^+$]<br>Found: 911.3934 |
| 27g | 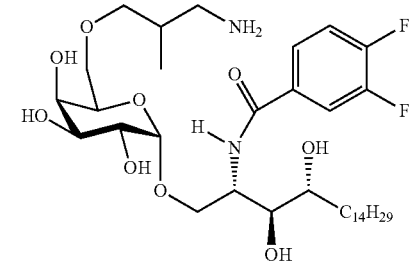 | $C_{35}H_{61}F_2N_2O_9$<br>Calc.: 692.8730 [M + H$^+$]<br>Found: 692.8707 |
| 27h | 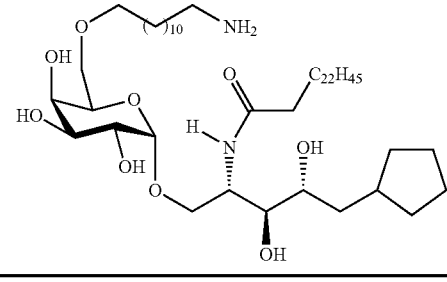 | $C_{52}H_{103}N_2O_9$<br>Calc.: 901.3922 [M + H$^+$]<br>Found: 901.3958 |

2,3-Di-O-benzyl-4,6-O-benzylidene-D-galactose (33) was prepared according to *ChemBioChem* 2012, 1349.

2,3-di-O-benzyl-4,6-O-benzylidene-α-D-galactosyl trifluoroacetimidate (34)

To a solution of 2,3-Di-O-benzyl-4,6-O-benzylidene-D-galactose (800 mg, 1.786 mmol, coevaporated 3 times with dry toluene) 33 in CH$_2$Cl$_2$ (7 mL) was added cesium carbonate (867 mg, 2.65 mmol). To the mixture was added 2,2,2-trifluoro-N-phenylacetimidoyl chloride 24 (551 mg, 2.65 mmol) and the reaction mixture was stirred at r.t. overnight after which it was filtered over celite and washed with CH$_2$Cl$_2$. The solvent was removed in vacuo and the crude product was purified by flash column chromatography on silica gel (gradient hexanes/EtOAc=8:1→1:1) to yield the imidate 34 (1.02 g, 92%) as a colorless oil. HR ESI Calcd for C$_{35}$H$_{32}$F$_3$NO$_6$ [M+H$^+$]: 620.6362. found: 620.6327.

(2S,3S,4R)-3,4-Bis-tert-butyldimethylsilyloxy-2-hexacosanoylamino-1-(2,3-di-O-benzyl-4,6-O-benzylidene-α-D-galactopyranosyl)octadecane (35)

Nucleophile 10 (150 mg, 0.162 mmol) and glycosylating agent 34 (151 mg, 0.243 mmol) were co-evaporated with toluene three times and dried on high vacuum for 3 h after which they were dissolved in Et$_2$O (2 mL) and THF (0.4 mL) and cooled to −40° C. To the mixture was added TMSOTf (8.0 µL, 0.043 mmol) and the solution was warmed to −10° C. over the period of 3 h. The reaction was quenched by the addition of NEt$_3$ (0.05 mL) and solvents were removed in vacuo and the crude product was purified by silica flash column chromatography (gradient hexanes/EtOAc=10:1→4:1) to afford glycoside 35 (140 mg, 64% α-anomer) as a white oil. HR ESI Calcd for C$_{83}$H$_{143}$NO$_9$Si$_2$ [M+H$^+$]: 1356.2067 found: 1356.2098.

(2S,3S,4R)-3,4-Bis-tert-butyldimethylsilyloxy-2-hexacosanoylamino-1-(2,3,4-tri-O-benzyl-6-hydroxy-α-D-galactopyranosyl)octadecane (36)

To a solution of 35 (80 mg, 0.06 mmol) in anhydrous CH$_2$Cl$_2$ (2 mL) under argon atmosphere were added copper (II) triflate (2 mg, 0.006 mmol) and BH$_3$.THF (0.30 mL, 0.30 mmol). After stirring for 2 h at room temperature, the yellow reaction mixture was quenched with methanol. Subsequently the mixture was diluted with EtOAc and washed with sat. NaHCO$_3$, water and brine. The organic layer was dried over Na$_2$SO$_4$ and the solvent was removed in vacuo and the crude product was purified by silica flash column chromatography (gradient hexanes/EtOAc: 8.5/1.5) to afford glycoside 36 (62 mg, 78%) as a yellowish foam. HR ESI Calcd for C$_{83}$H$_{145}$NO$_9$Si$_2$ [M+H$^+$]: 1358.2226. found: 1358.2196.

The Boc-protected PEG derivative 38 was purchased at Creative PEGWorks, Winston Salen, N.C., USA.

(2S,3S,4R)-3,4-Bis-tert-butyldimethylsilyloxy-2-hexacosanoylamino-1-(2,3,4-tri-O-benzyl-6-(carbonyl-1-ethyl-2-(tri(1-ethanoyl)1-ethanoyl-2-(tert-butoxy-carbonyl)amino)-α-D-galactopyranosyl) octadecane (37)

To a solution of 38 (18 mg, 0.05 mmol) in DMF (5 mL) was added O-(Benzotriazol-1-yl)-N,N,N',N'-tetramethyluronium tetrafluoroborate TBTU (16.1 mg, 0.05) and diisopropylethylamine (12.9 mg, 17 µl, 0.1 mmol). The mixture was stirred for 30 min at r.t. Then a mixture of 36 (50 mg, 0.04 mmol) in DMF (1 ml) was added to the reaction mixture and stirred for 5 hours. Subsequently, the reaction mixture was diluted with $CH_2Cl_2$ (15 mL) and the resulting mixture was washed with 5% HCl (2×3 mL), 1M $NaHCO_3$ (3×3 mL) and water (2×3 mL). The organic layer was collected, dried ($MgSO_4$), filtered and concentrated to give the crude ester product which was purified by flash column chromatography on silica gel (gradient hexanes/EtOAc=8:1→1:1) to yield the linker-equipped glycolipid 37 (40 mg, 63%) as a colorless oil. HR ESI Calcd for $C_{99}H_{174}N_2O_{16}Si_2$ [M+H$^+$]: 1705.6272. found: 1705.6231.

Mono-tert.-butyl suberic acid was prepared according to *Chem. Commun.* 1999, 823.

Compound 37a was prepared according to the above reaction procedure in 53% yield.

| comp. | structure | mass spec |
|---|---|---|
| 39 | (structure shown) | $C_{95}H_{167}NO_{12}Si_2$<br>Calc.: 1572.5243 [M + H$^+$]<br>Found: 1572.5216 |

(2S,3S,4R)-3,4-Bis-tert-butyldimethylsilyloxy-2-hexacosanoylamino-1-(2,3,4-tri-O-benzyl-6-(carbonyl-1-ethyl-2-(tri(1-ethanoyl)1-ethanoyl-2-amino)-α-D-galactopyranosyl)octadecane (25a)

37 (40 mg, 0.02 mmol) was dissolved in TFA (1 mL) and stirred at r.t. for 30 min. The solution was diluted with $CH_2Cl_2$ (2 mL) and then carefully neutralized (to pH ~8) with sat. aq. $NaHCO_3$ solution (8 mL). Additional $CH_2Cl_2$. was added and the organic layer was dried over $Na_2SO_4$ and the solvent was removed in vacuo and the crude product was purified by silica flash column chromatography (gradient hexanes/EtOAc: 10:1→1:1) to afford the linker-equipped glycolipid 25a (33 mg, 89%) as a yellowish oil. HR ESI Calcd for $C_{94}H_{166}N_2O_{14}Si_2$ [M+H$^+$]: 1605.5112. found: 1605.5088.

Compound 25b was prepared accordingly from compound 39:

| comp. | structure | mass spec |
|---|---|---|
| 25b | (structure) | $C_{91}H_{159}NO_{12}Si_2$<br>Calc.: 1516.4179 [M + H$^+$]<br>Found: 1516.4223 |

(2S,3S,4R)-2-Hexacosanoylamino-1-(2,3,4-tri-O-benzyl-6-(carbonyl-1-ethyl-2-(tri(1-ethanoyl)1-ethanoyl-2-amino)-α-D-galactopyranosyl)octadecane-3,4-diol (26a)

To a solution of bis-TBS ether 25a (33.0 mg, 20.7 μmol) in THF (1 mL) was added a solution of TBAF (1 M in THF, 0.150 mL, 0.15 mmol) slowly. After 3.5 h the reaction mixture was diluted with $CH_2Cl_2$ (10 mL). Solvents were removed in vacuo and crude product was purified by silica flash column chromatography (gradient hexanes/EtOAc=1:0→1:1) to afford diol 26a (24.5 mg, 86%) as a clear oil. HR ESI Calcd for $C_{82}H_{138}N_2O_{14}$ [M+H$^+$]: 1376.9893. found: 1376.9876.

Compound 26b was prepared accordingly from compound 25b:

| comp. | structure | mass spec |
|---|---|---|
| 26b | (structure) | $C_{79}H_{131}NO_{12}$<br>Calc.: 1287.8959 [M + H$^+$]<br>Found: 1287.8914 |

(2S,3S,4R)-1-(6-(Carbonyl-1-ethyl-2-(tri(1-ethanoyl)1-ethanoyl-2-amino)-α-D-galactopyranosyl)-2-hexacosanoylaminooctadecane-3,4-diol (27a)

To a solution diol 26a (25 mg, 17.7 μmol) in EtOH (0.5 mL) and chloroform (0.15 mL) was added Pd(OH)$_2$ on charcoal (10% w/w, wet 35 mg). The solution was stirred at r.t. under an atmosphere of Ar for 15 min. after which H$_2$ gas was inserted into the suspension and the mixture was hydrogenated for 12 h. The mixture was filtered over celite and thoroughly washed with $CH_2Cl_2$, THF and MeOH. Solvents were removed in vacuo and the crude was purified by silica flash column chromatography on silica gel ($CH_2Cl_2$/MeOH=4:1) to afford linker equipped GSL 27a (18 mg, 92%) as a colorless oil. HR ESI Calcd for $C_{61}H_{120}N_2O_{14}$ [M+H$^+$]: 1106.6209 found: 1106.6177.

Compound 27b was prepared accordingly from compound 26b:

| comp. | structure | mass spec |
|---|---|---|
| 27b | 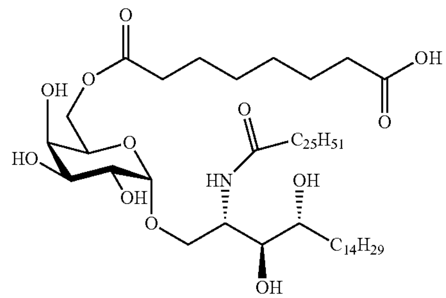 | $C_{58}H_{113}NO_{12}$<br>Calc.: 1017.5275 [M + H$^+$]<br>Found: 1017.5231 |

5-(((6-(((2R,3R,4S,5R,6S)-6-(((2S,3S4R)-2-hexacosanamido-3,4-dihydroxyoctadecyl)oxy)-3,4,5-trihydroxytetrahydro-2H-pyran-2-yl)methoxy)hexyl)amino)-5-oxopentanoic acid (40)

To gylocolipid 27 (10 mg, 10.44 µmol) in chloroform:methanol:triethylamine mixture (1:1:0.1, 7 ml) was added excess glutaric anhydride (14.9 mg, 131 µmol) in on eportion and left to stir at room temperature. After three days the completion of the reaction was indicated by the disappearance of the starting material mass on LCMS. The reaction was then evaporated to dryness and the resultant residue was triturated with dichloromethane to give the desired product 40 (8 mg, 72%) as a white solid.

| comp. | structure | mass spec |
|---|---|---|
| 40 | 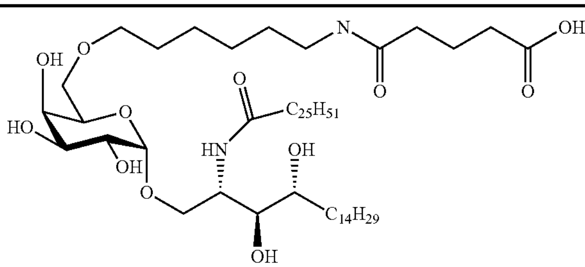 | $C_{61}H_{118}N_2O_{12}$<br>Calc.: 1069.861 [M + H$^+$]<br>Found: 1069.642 |

Synthesis of the Antigen-Carbohydrate Glycolipid Conjugate:

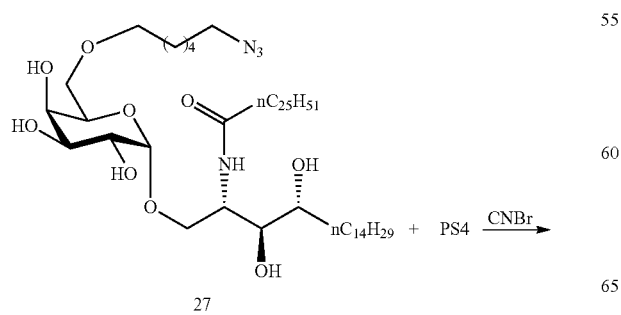

121

-continued

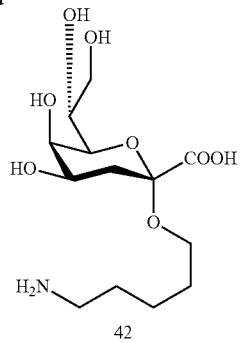

PS4 (1 mg) was dissolved in aq. NaOH solution (pH 10.95) to a final concentration of 10 mg/mL. The PS4 was activated with 15 μL of cyanogen bromide (10 mg/mL in acetonitrile) and left to stir at the room temperature for 10 min. To the activated PS4, μL of 27 was added (10 mg/2 mL in DMSO:THF, 1:1) and the mixture was incubated for 18 h at room temperature. After adjusting the pH to 6 with 0.1M aq. HCl, the mixture was dialyzed (12-14 k MWCO) against double distilled water, concentrated via ultrafiltration (10 k MWCO) then lyophilized.

Compounds 27a and 27c-h have been conjugated to PS4 accordingly and also showed immunogenic activity.

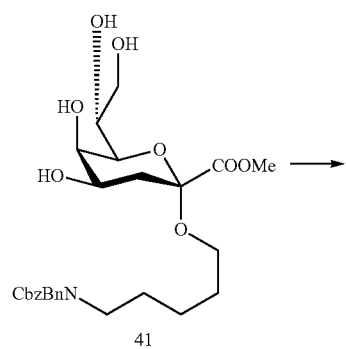

122

-continued

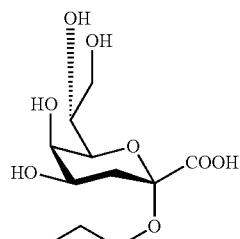

Methyl ester 4.57 (provided by Dr. M. Oberli) (10 mg, 0,018 mmol) was dissolved in a mixture of THF (1.0 mL) and NaOH (0.1 M, 1 mL). The reaction mixture was stirred at r.t. for 1 h after which it was neutralized by the addition of Amberlite IR-120 (H+) resin. The resin was removed by filtration and solvents were removed in vacuo. The crude product was purified by silica gel chromatography (20% MeOH in CH2Cl2) to yield a white powder which was dissolved in THF (1.0 ml), water (1.0 mL) and MeOH (1.0 mL). To the mixture was added Pd on charcoal (20 mg). A stream of hydrogen was passed through the suspension for 20 min., after which the suspension was stirred for another 18 h under an H2 atmosphere. The suspension was filtered over celite and washed with MeOH and water (2×). Solvents were removed in vacuo and the crude product was purified by Sephadex G25 size-exclusion chromatography (eluent: 5% EtOH in water) to yield acid 4.13 (5.0 mg, 85% over two steps) a white powder. [α]D r.t.=−14.2 (c=1.0, water); Rf=0.67 (Isopropanol/1M aq. NH4OAc=2:1); IR (film) vmax 3256, 2938, 1571, 1410, 1050, 830 cm-1; 1H NMR (400 MHz, D2O) δ 4.00-3.84 (m, 3H), 3.74 (dd, J=19.7, 9.9 Hz, 3H), 3.63 (d, J=8.9 Hz, 1H), 3.46 (dd, J=15.8, 6.5 Hz, 1H), 3.01 (t, J=7.5 Hz, 2H), 2.43 (dd, J=12.1, 4.6 Hz, 1H), 1.79 (t, J=12.3 Hz, 1H), 1.67 (dd, J=14.0, 6.5 Hz, 2H), 1.63-1.57 (m, 2H), 1.44 (dd, J=15.2, 7.9 Hz, 2H); 13C NMR (101 MHz, D2O) δ 181.4, 173.9, 101.1, 73.3, 69.0, 67.4, 65.2, 64.1, 39.3, 34.7, 28.2, 26.3, 23.2, 22.0; HR ESI Calcd for C13H25NO8 [M−H+]: 322.1507. found: 322.1502.

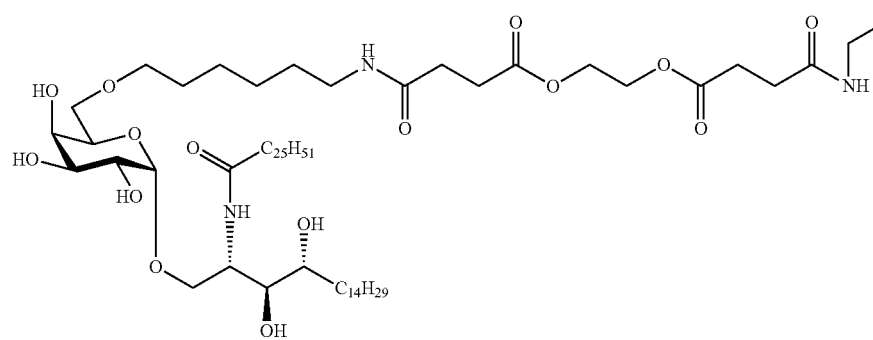

(2S,3S,4R)-1-(6-(6'-Hexanyl succinamido ethyl-eneglycol succinimidamido 5"-pentanyl α-3'"-de-oxy-D-manno-oct-2'"-ulosonic acid pyranoside)-α-D-galactopyranosyl)-2-hexacosanoylaminooctadecane-3,4-diol
(Glycoconjugate 43)

To a solution of linker-equipped KDO 42 (1.5 mg, 4.6 µmol) and glycolipid 27 (4.4 mg, 4.6 µmol) in DMSO/pyridine (0.1 mL, ratio=1:1 v/v) was added ethyleneglycol bissuccinimidyl succinate (EGS) (2.1 mg, 4.6 µmol) dissolved in DMF (0.1 mL). The reaction mixture was stirred at r.t. for 24 h after which solvents were removed by lyophilization. The crude product was purified by LH-20 size exclusion chromatography (eluent: MeOH/CH2Cl2=1:1) to yield conjugate 43 (3.0 mg, 42%) as a pale yellow powder. [α]D r.t.=+43.9 (c=0.2, Pyridine); Rf=0.54 (CH2Cl2/MeOH=85:15); IR (film) vmax 3308, 2918, 2850, 1781, 1709, 1645, 1548, 1467, 1378, 1211, 1157, 1071, 1020, 952, 816, 719 cm-1; 1H NMR (400 MHz, d-pyr) 8.52 (m, 2H), 8.44 (d, J=8.7 Hz, 1H), 5.56 (d, J=3.9 Hz, 1H), 5.26 (s, 1H), 4.88 (s, 1H), 4.66 (ddd, J=13.1, 9.9, 4.4 Hz, 2H), 4.55 (d, J=4.6 Hz, 1H), 4.52-4.39 (m, 5H), 4.39-4.31 (m, 7H), 4.20-3.93 (m, 2H), 3.85 (d, J=7.3 Hz, 1H), 3.79-3.72 (m, 1H), 3.47 (ddd, J=20.0, 14.8, 8.3 Hz, 3H), 3.39-3.32 (m, 1H), 3.22 (dd, J=11.9, 4.5 Hz, 1H), 3.08 (ddd, J=6.7, 5.8, 2.5 Hz, 1H), 2.94-2.84 (m, 4H), 2.79 (dd, J=8.5, 5.0 Hz, 3H), 2.73 (t, J=4.8 Hz, 2H), 2.53-2.49 (m, 18H), 2.33 (t, J=6.9 Hz, 1H), 1.99-1.66 (m, 4H), 1.66-1.47 (m, 6H), 1.42-1.20 (m, 71H), 0.89 (t, J=6.3 Hz, 6H). δ; 13C NMR (151 MHz, d-pyr) δ 173.6, 171.7, 170.5, 169.3, 101.9, 101.0, 77.1, 76.8, 72.9, 71.9, 71.9, 71.6, 71.4, 71.2, 71.1, 70.6, 69.5, 69.1, 67.8, 66.5, 64.4, 63.4, 63.3, 62.9, 62.8, 61.9, 51.7, 43.5, 41.5, 40.2, 40.1, 37.2, 37.2, 34.8, 32.6, 32.5, 31.3, 30.8, 30.6, 30.5, 30.5, 30.5, 30.4, 30.4, 30.4, 30.4, 30.3, 30.3, 30.3, 30.2, 30.0, 30.0, 29.3, 27.6, 27.0, 26.5, 26.5, 24.3, 23.4, 14.7; HR ESI Calcd for C79H147N3O23 [M+Na+]: 1529.0318. found: 1529.0363.

The mode of action is illustrated by the antigen of invasive pneumococcal disease: the pneumococcal capsule polysaccharide (CPS) is covalently attached to a glycolipid. B cells specific for CPS will internalize the conjugate by receptor-mediated endocytosis and the conjugate will be cleaved in late endosomes, generating free αGalCer. In the late endosomal compartment, αGalCer will be complexed with CD1d antigen-presenting molecules and upon plasma-membrane recycling of CD1d be presented to invariant natural killer T (iNKT) cells.

Stimulation of iNKT cells by the αGalCer:CD1d complex on the surface of the antigen-presenting B cell will induce the release of soluble cytokines necessary for B cell help and memory generation. By this strategy a final long term immunological memory is induced, leading to the production of memory B-cells and the supply of high affinity IgG antibodies.

Figure 1:
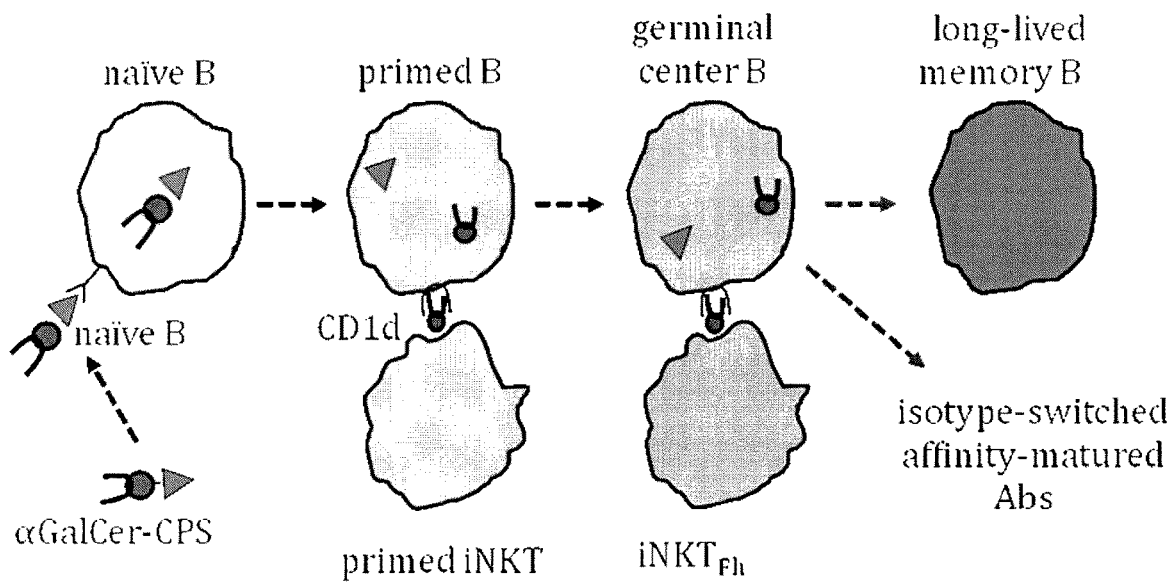
FIG. 1. Model of glycoconjugate vaccine action.
Figure 2:
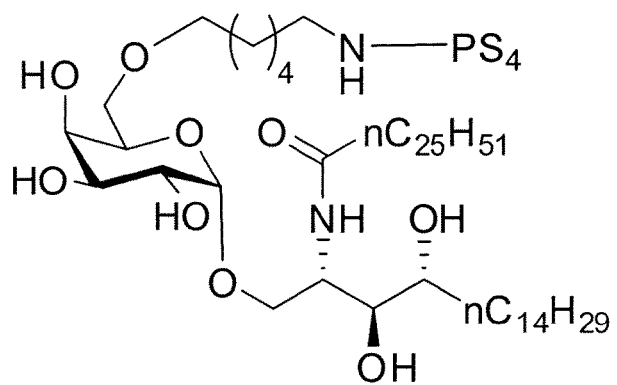

FIG. 2. Glycoconjugate vaccine 1 containing the antigenic capsular polysaccharide portion PS4.

Figure 3:
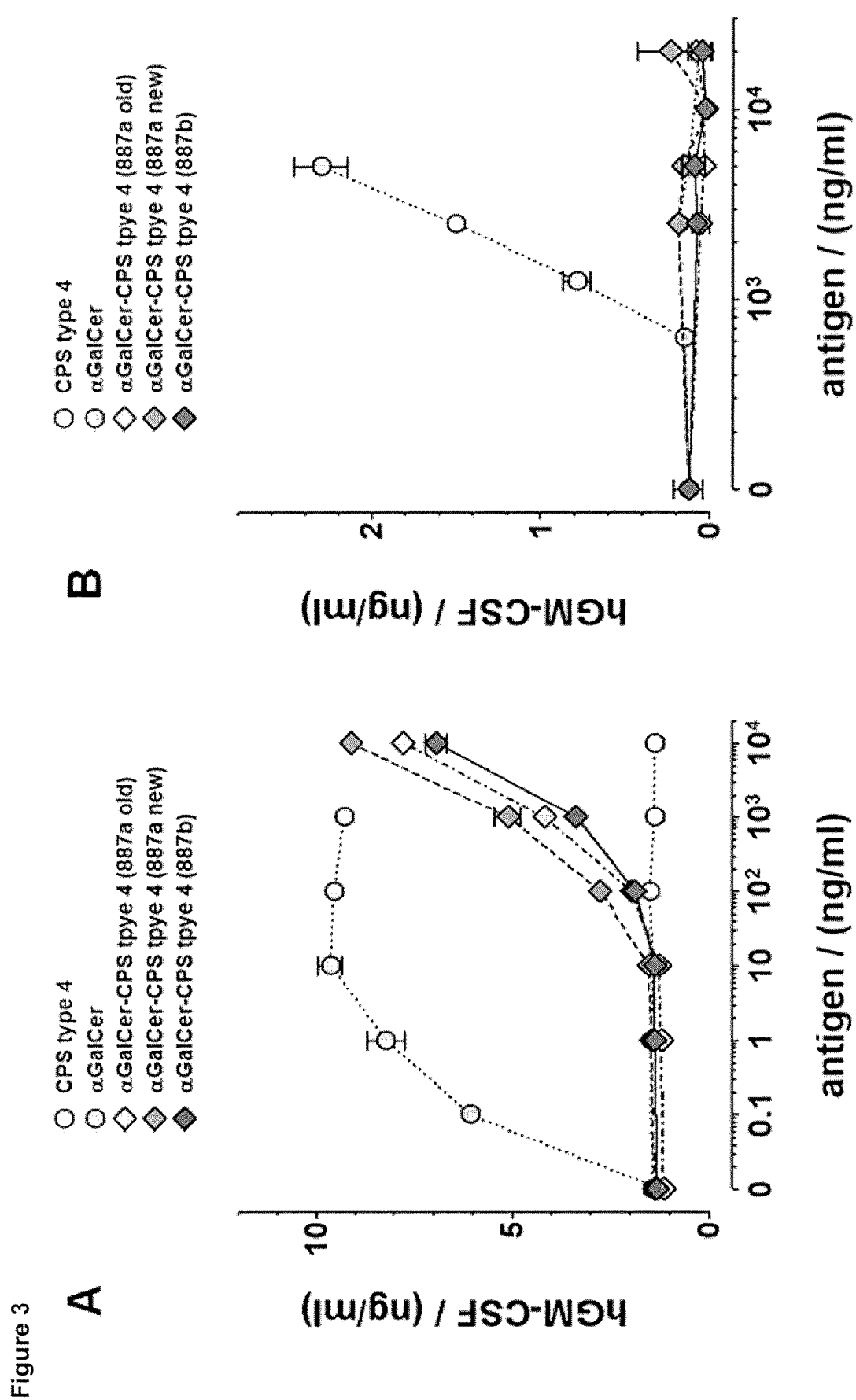

FIG. 3. In vitro activity of the conjugate vaccine. αGalCer-CPS-pulsed CD1d-positive APC stimulate iNKT cells. Different batches of αGalCer-CPS type 4 conjugate vaccine (diamonds) are active in vitro when αGalCer is freed from CPS in living cells (A). αGalCer is entirely conjugated to CPS as remaining activity is not found when activating iNKT cells in a cell-free system (B). Unconjugated CPS type 4 (open circles) or αGalCer (closed circles) alone as control.

Figure 4:
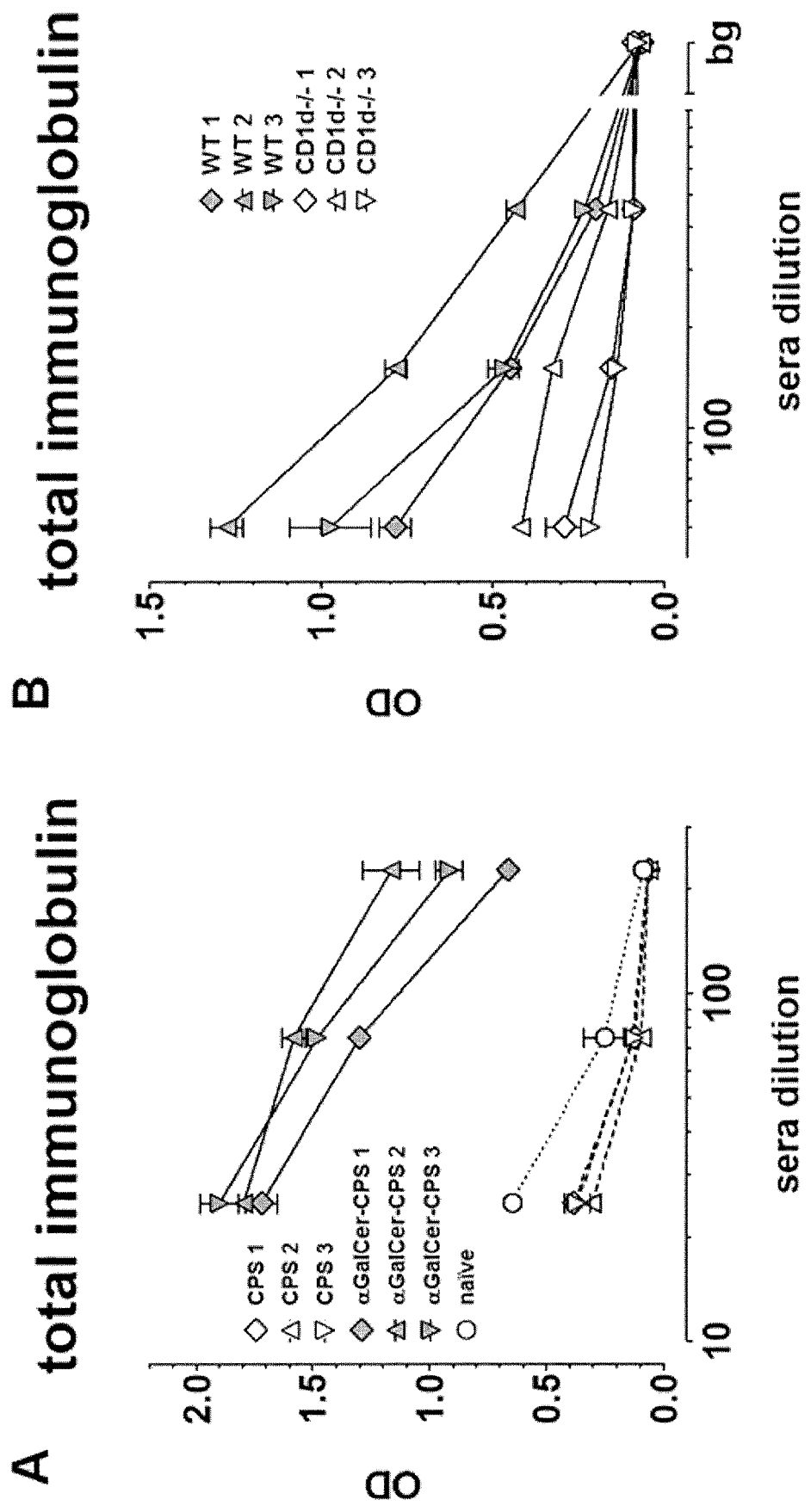

FIG. 4. In vivo activity of the conjugate vaccine. Only αGalCer-CPS increases Abs response in C57BL/6 mice and the Abs response is dependent on NKT cells/CD1d. (A) WT C57BL/6 mice vaccinated with αGalCer-CPS (closed symbols) or CPS alone (open symbols) are bled after immunization and the CPS-specific Abs are assessed by ELISA. (B) WT C57BL/6 (WT, closed symbols) or CD1d-deficient (CD1d−/−, open symbols) mice immunized with αGalCer-CPS are bled after vaccination and the CPS-specific Abs are measured by ELISA.

Figure 5:
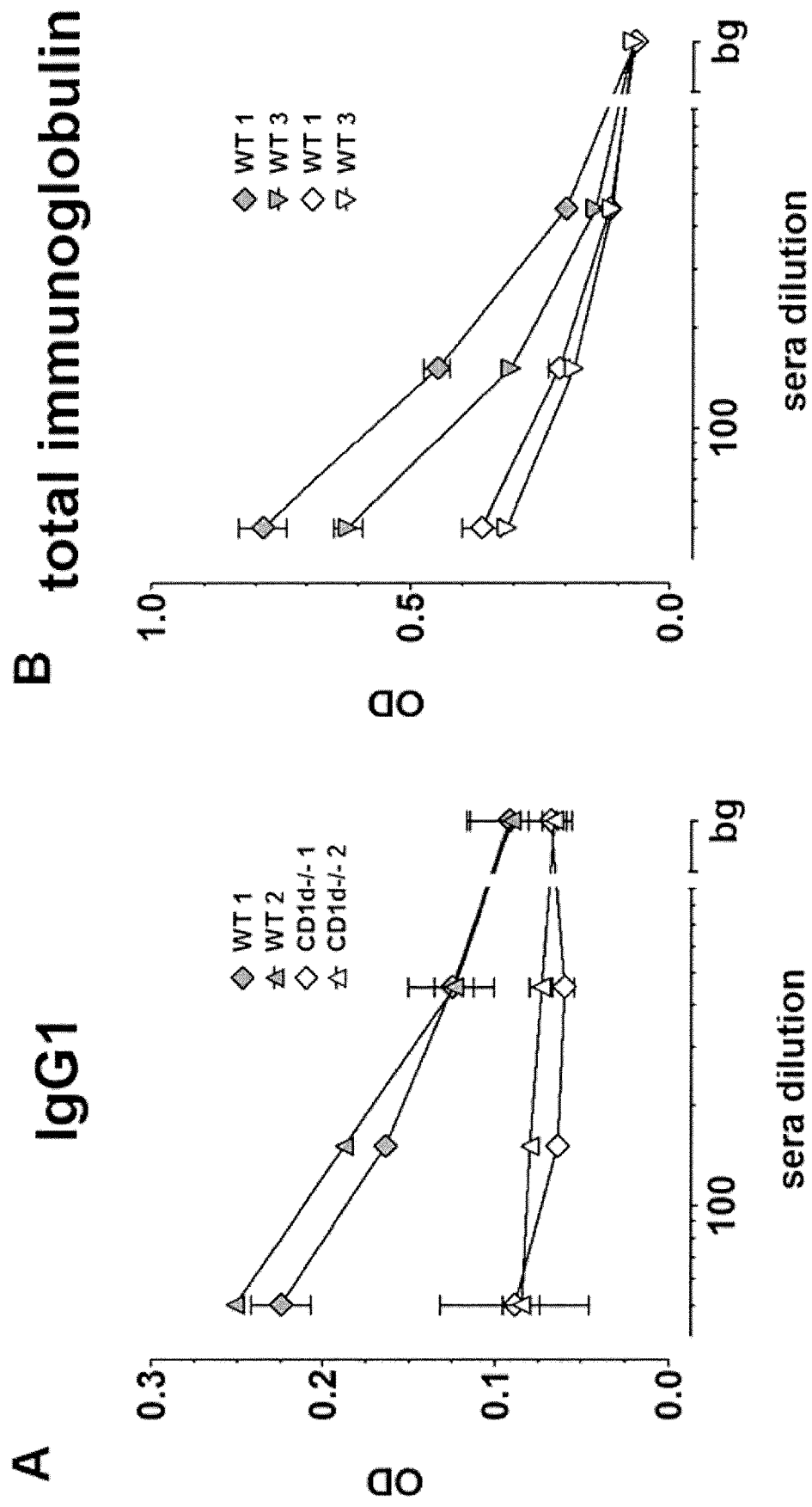

FIG. 5. In vivo antibody response after vaccination. The Abs response includes IgG subclasses and shows reactivity to common epitopes on different S. pneumoniae CPS. (A) WT C57BL/6 (WT, closed symbols) or CD1d-deficient (CD1d−/−, open symbols) mice immunized with αGalCer-CPS are bled after vaccination and the CPS-specific Abs subclasses are measured by ELISA (IgG1 given as representative example). (B) C57BL/6 mice vaccinated with αGalCer-CPS are bled after immunization and the CPS type 4 (closed symbols) or CPS type 2 (open symbols)-specific Abs are assessed by ELISA.

FIG. 6. CPS-specific hybridomas express affinity matured IgM and all IgG subclasses with some preferential V, D, J segment usage. Hybridomas from αGalCer-CPS-immunized mice were established and classified by ELISA and sequencing. * aminoacid (aa) or nucleotide (nuc) substitutions in comparison to germ-line sequence.

Figure 7:
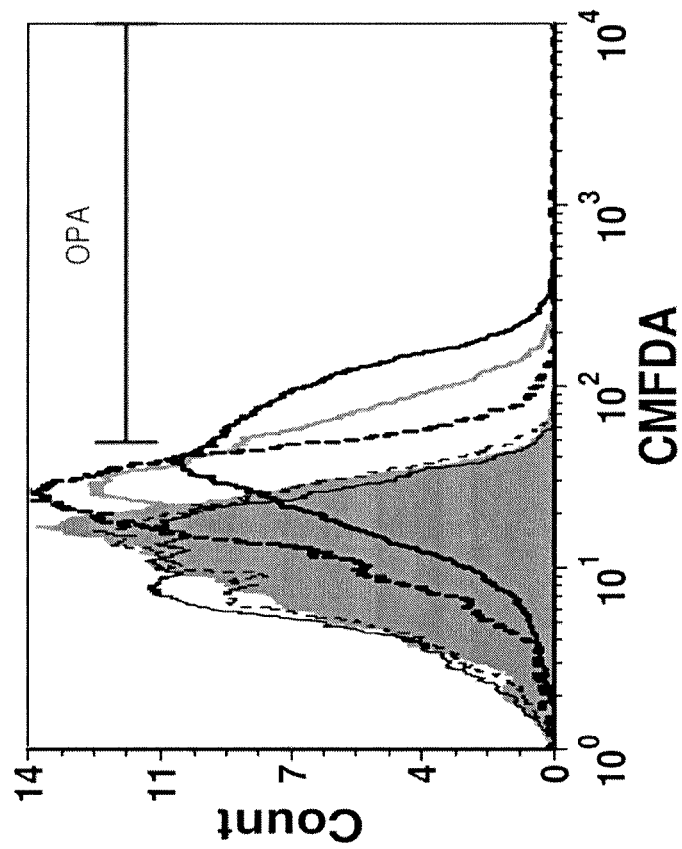

FIG. 7. Protection from infection with S. pneumoniae in a mouse model. CSP-specific mAbs promote bacterial opsonization. Uptake of fluorescently labeled S. pneumoniae serotype 4 into APC alone, in the presence of complement (C') and/or mAbs 12F10 (CPS-specific hybridoma purified) or C15 (anti-human TCRAV24). Percent of positive cells according to background (OPA marker) is given in a table.

Figure 8:
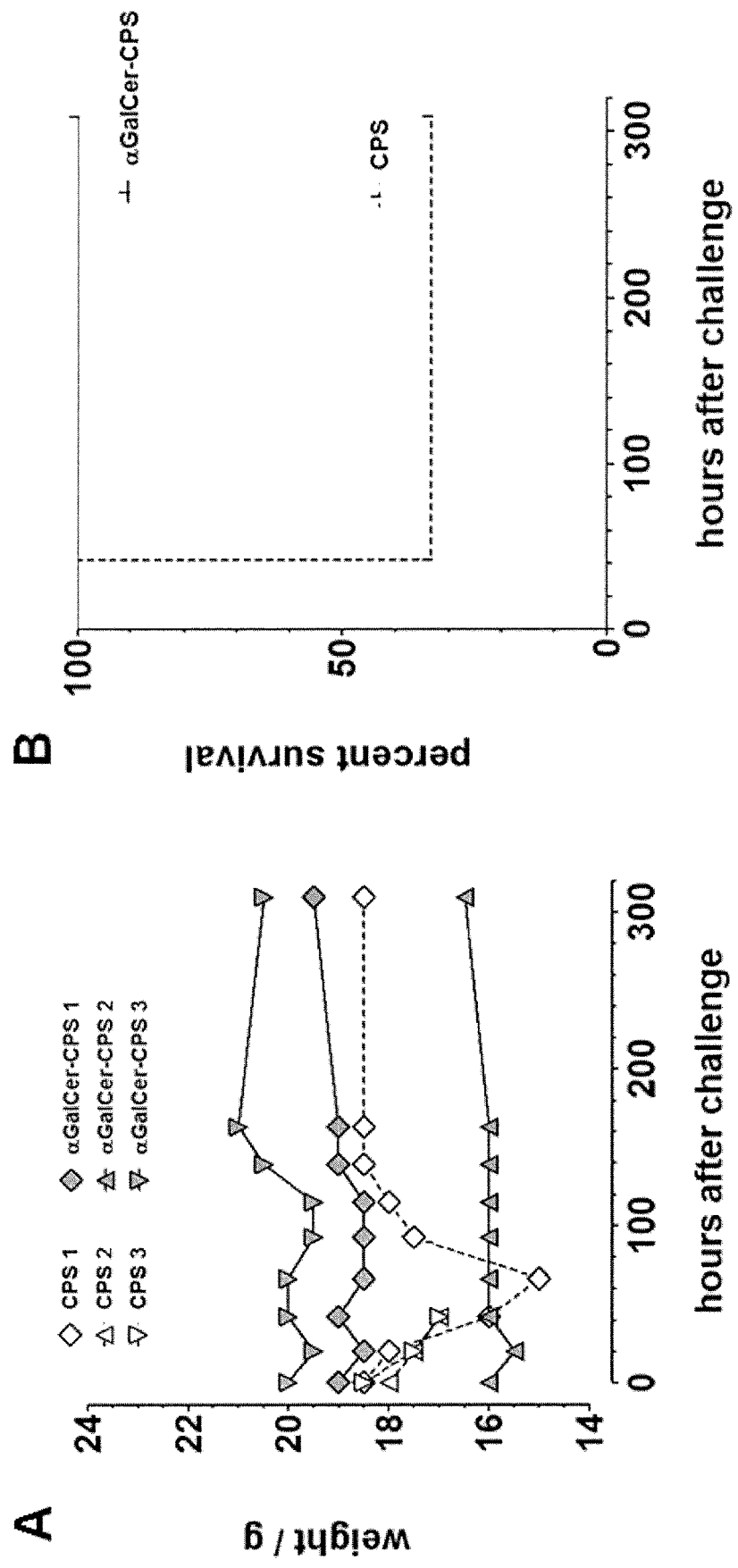

FIG. 8. αGalCer-CPS-vaccinated C57BL/6 mice show long-term protection to challenge with S. pneumoniae. Mice vaccinated with αGalCer-CPS (A: closed symbols; B: line) or CPS alone (A: open symbols; B: dashed line) are infected with S. pneumoniae one week (A) or up to 3 months (B) after the last immunization. Mice are scored for disease, weight and survival over several days (given in hours). All αGalCer-CPS injected mice survived (B) without disease symptoms. Severe weight loss (A) is just observed for the CPS alone condition independently of the animal's survival (B).

Figure 9:
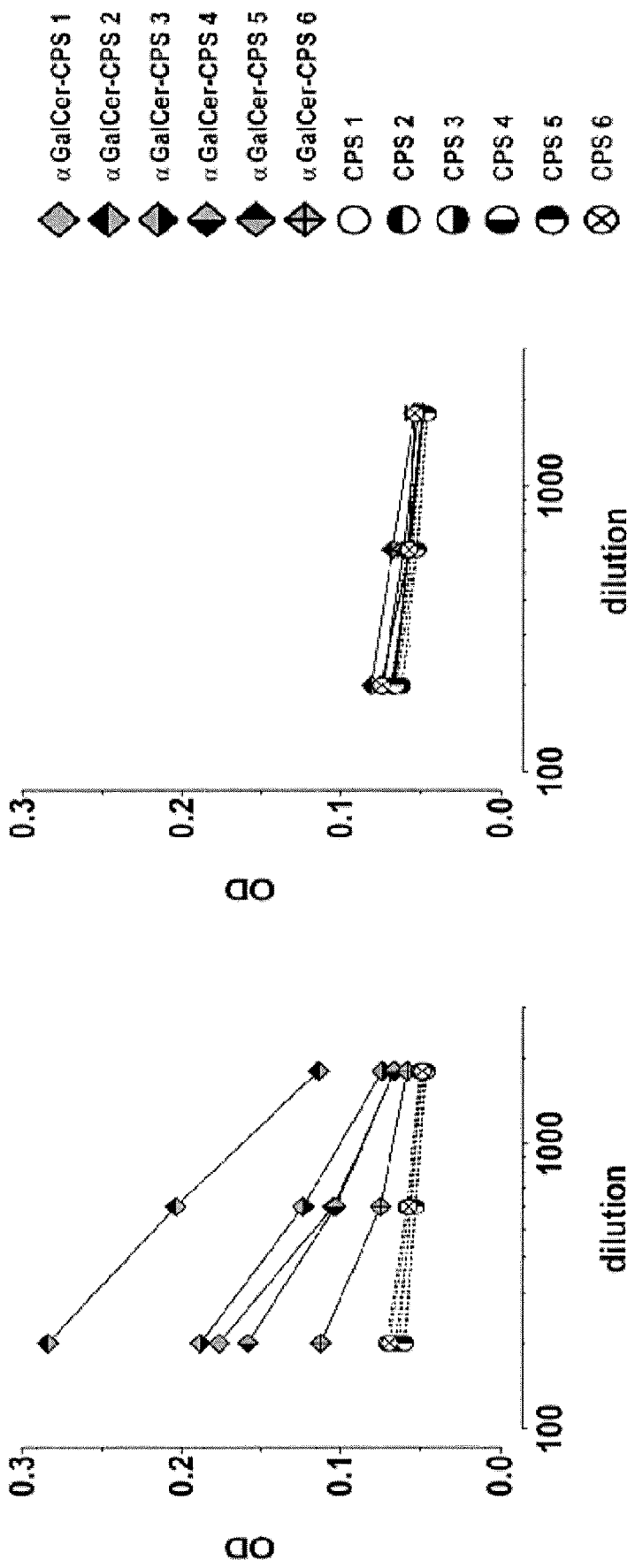
Figure 10:
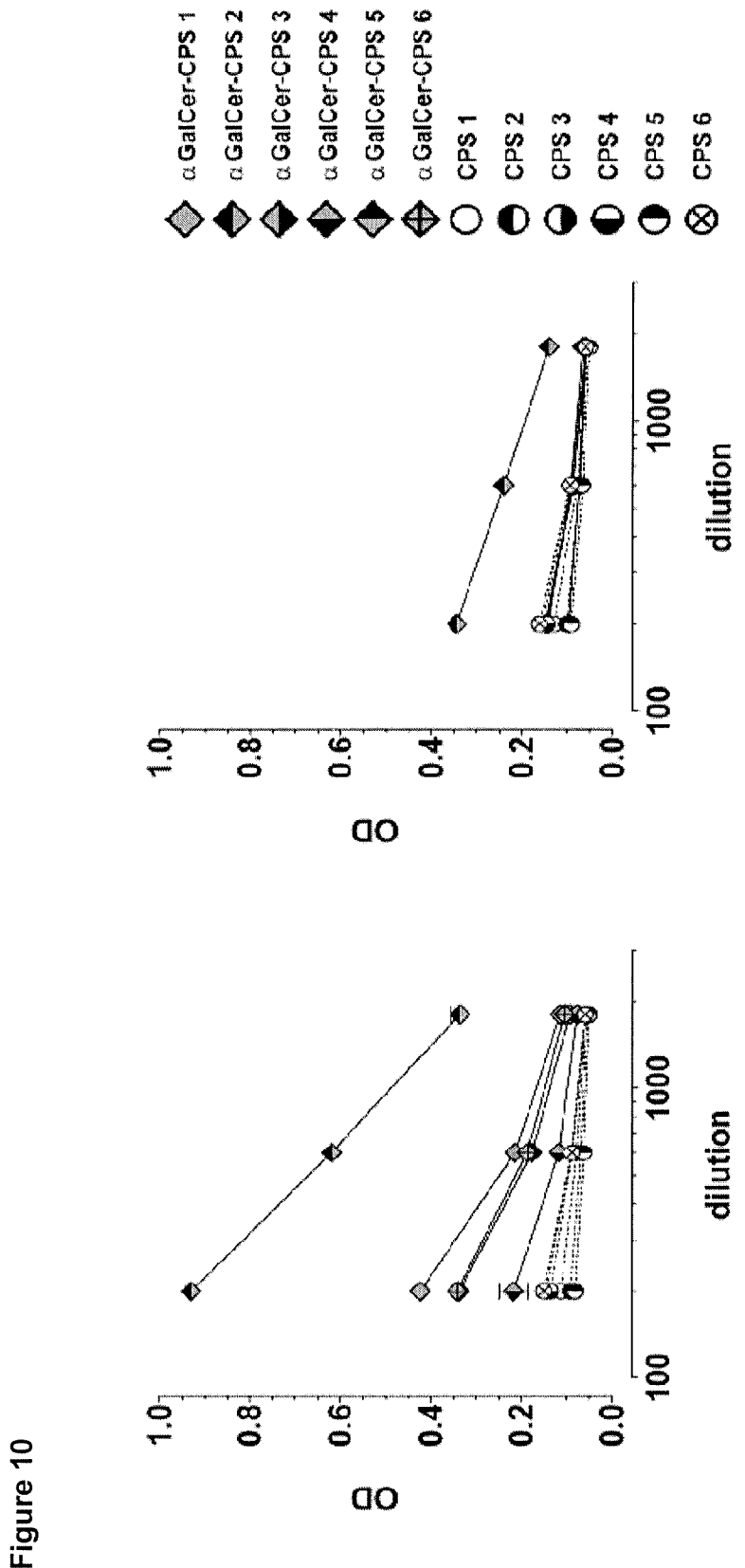

FIGS. 9 and 10. Isotype and specificity of anti-polysaccharide Abs (IgG, FIG. 9; IgM, FIG. 10).

The invention claimed is:

1. Compound of the general formula (XIV):

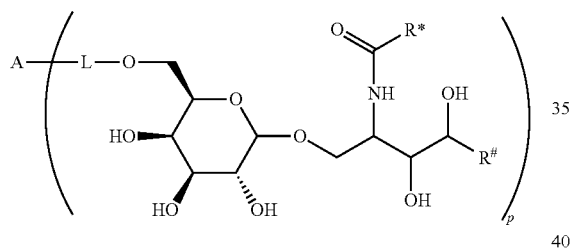

(XIV)

Wherein:

A represents a carbohydrate antigen selected from the group consisting of a bacterial capsular saccharide, a saccharide of a viral glycoprotein, a saccharide antigen of sporozoa or parasites, a saccharide antigen of pathogenic fungi, and a saccharide antigen which is specific to cancer cells, and has a number u of 1 to 10,000 of carbohydrate monomers, p is the number of residues

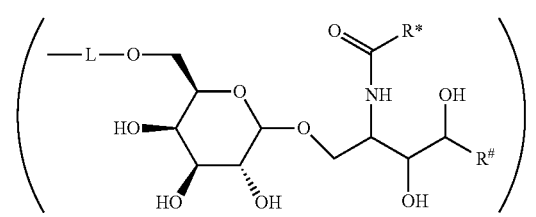

which are bound to the carbohydrate antigen A, and
p is an integer defined as follows:
p is 1 or 2 if u is 1
p is 1, 2, 3 or 4 if u is 2
p is 1, 2, 3, 4, 5 or 6 if u is 3
p is 1, 2, 3, 4, 5, 6, 7 or 8 if u is 4

$1 \leq p \leq 10$ if $5 \leq u \leq 10$ $2 \leq p \leq 50$ if $11 \leq u \leq 100$ $20 \leq p \leq 200$ if $101 \leq u \leq 1000$ $50 \leq p \leq 400$ if $1001 \leq u \leq 10000$ L represents $-L^1-L^2-$, $-L^2-$, $-L^2-L^3-$ or $-L^1-L^2-L^3-$;

$L^1$ represents one of the following residues:

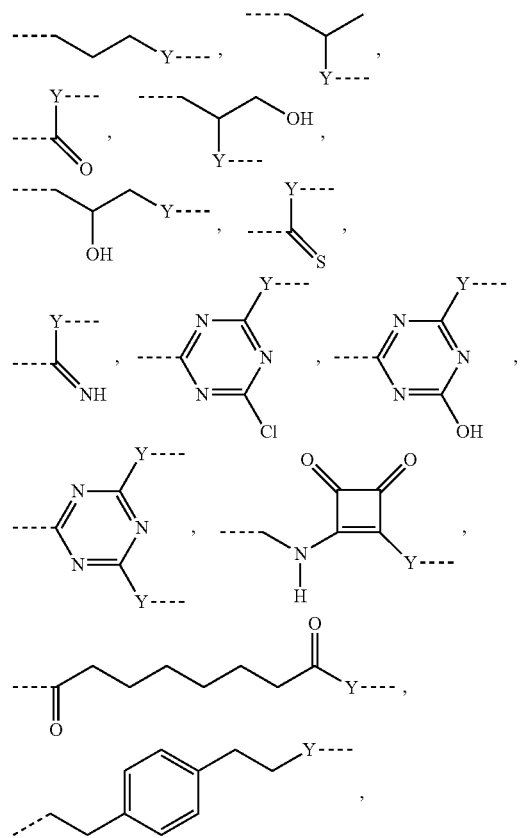

-continued

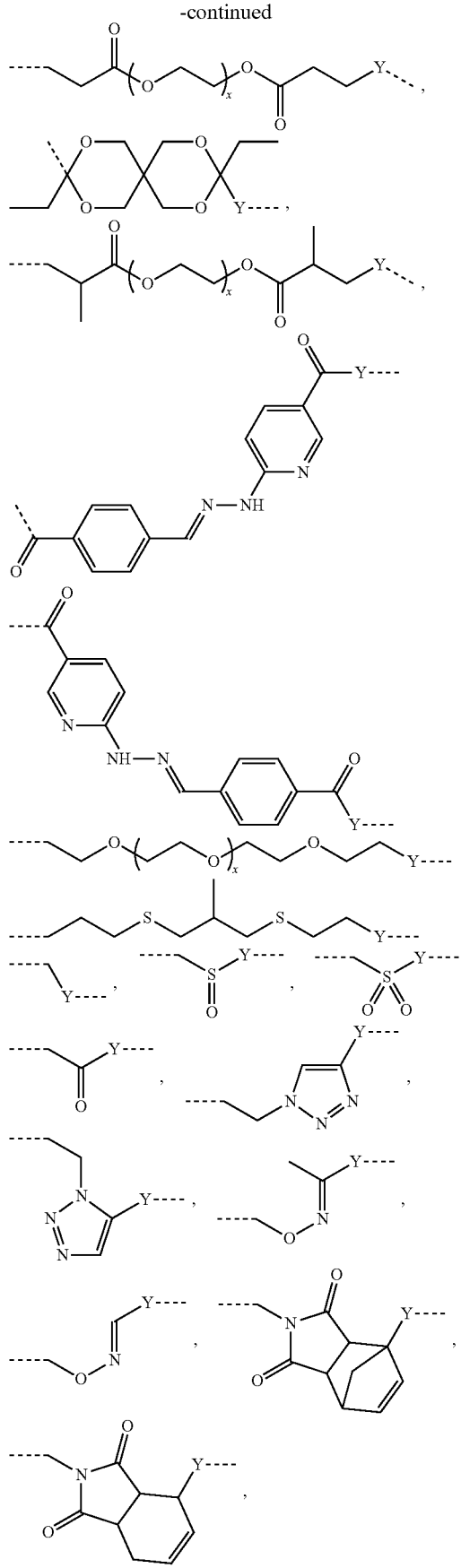

-continued

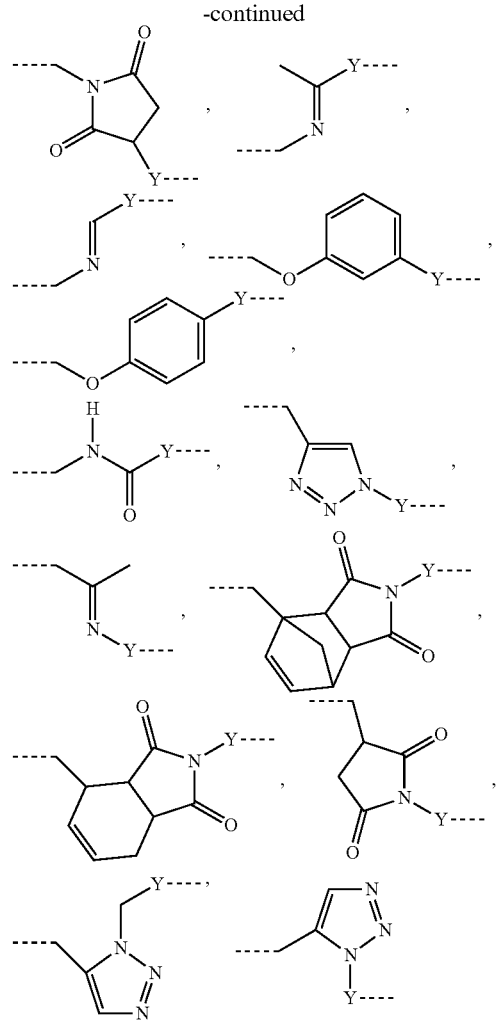

wherein x is an integer from 1 to 60;
Y represents a bond, —NH—, —O—, —S—; —S—S—;
L² represents —CH₂—, —C₂H₄—, —C₃H₆—, —C₄H₈—, —C₅H₁₀—, —C₆H₁₂—, —C₇H₁₄—, —C₈H₁₆—, —C₉H₁₈—, —C₁₀H₂₀—, —CH(CH₃)—, —C[(CH₃)₂]—, —CH₂—CH(CH₃)—, —CH(CH₃)—CH₂—, —CH(CH₃)—C₂H₄—, —CH₂—CH(CH₃)—CH₂—, —C₂H₄—CH(CH₃)—, —CH₂—C[(CH₃)₂]—, —C[(CH₃)₂]—CH₂—, —CH(CH₃)—CH(CH₃)—, —C[(C₂H₅)(CH₃)]—, —CH(C₃H₇)—, —(CH₂—CH₂—O)ₙ—CH₂—CH₂—, —CO—CH₂—, —CO—C₂H₄—, —CO—C₃H₆—, —CO—C₄H₈—, —CO—C₅H₁₀—, —CO—C₆H₁₂—, —CO—C₇H₁₄—, —CO—C₉H₁₆—, —CO—C₉H₁₈—, —CO—C₁₀H₂₀—, —CO—CH(CH₃)—, —CO—C[(CH₃)₂]—, —CO—CH₂—CH(CH₃)—, —CO—CH(CH₃)—CH₂—, —CO—CH(CH₃)—C₂H₄—, —CO—CH₂—CH(CH₃)—CH₂—, —CO—C₂H₄—CH(CH₃)—, —CO—CH₂—C[(CH₃)₂]—, —CO—C[(CH₃)₂]—CH₂—, —CO—CH(CH₃)—CH(CH₃)—, —CO—C[(C₂H₅)(CH₃)]—, —CO—CH(C₃H₇)—, —Oβ—(CH₂—CH₂—O)ₙ—CH₂—CH₂—;
n represents an integer from 1 to 60;
L³ represents —CO—, —O—CO—, —NH—CO—, —NH(C=NH)—, —SO₂—, —O—SO₂—, —NH—, —NH—CO—CH₂—;

R* and R# represent independently of each other a linear or branched or cyclic, substituted or unsubstituted, saturated or unsaturated carbon residue consisting of 1 to 30 carbon atoms.

2. Compound according to claim 1, wherein the carbohydrate monomers of the carbohydrate antigen are selected from the group consisting of:
α-D-ribopyranose, α-D-arabinopyranose, α-D-xylopyranose, α-D-lyxopyranose, α-D-allopyranose, α-D-altropyranose, α-D-glucopyranose, α-D-mannopyranose, α-D-glucopyranose, α-D-idopyranose, α-D-galactopyranose, α-D-talopyranose, α-D-psicopyranose, α-D-fructopyranose, α-D-sorbopyranose, α-D-tagatopyranose, α-D-ribofuranose, α-D-arabinofuranose, α-D-xylofuranose, α-D-lyxofuranose, α-D-allofuranose, α-D-altrofuranose, α-D-glucofuranose, α-D-mannofuranose, α-D-gulofuranose, α-D-idofuranose, α-D-galactofuranose, α-D-talofuranose, α-D-psicofuranose, α-D-fructofuranose, α-D-sorbofuranose, α-D-tagatofuranose, α-D-xylulofuranose, α-D-ribulofuranose, α-D-threofuranose, α-D-rhamnopyranose, α-D-erythrofuranose, α-D-glucosamine, α-D-glucopyranuronic acid, β-D-ribopyranose, β-D-arabinopyranose, β-D-xylopyranose, β-D-lyxopyranose, β-D-allopyranose, β-D-altropyranose, β-D-glucopyranose, β-D-mannopyranose, β-D-glucopyranose, β-D-idopyranose, β-D-galactopyranose, β-D-talopyranose, β-D-psicopyranose, β-D-fructopyranose, β-D-sorbopyranose, β-D-tagatopyranose, β-D-ribofuranose, β-D-arabinofuranose, β-D-xylofuranose, β-D-lyxofuranose, β-D-rhamnopyranose, β-D-allofuranose, β-D-altrofuranose, β-D-glucofuranose, β-D-mannofuranose, β-D-gulofuranose, β-D-idofuranose, β-D-galactofuranose, β-D-talofuranose, β-D-psicofuranose, β-D-fructofuranose, β-D-sorbofuranose, β-D-tagatofuranose, β-D-xylulofuranose, β-D-ribulofuranose, β-D-threofuranose, β-D-erythrofuranose, β-D-glucosamine, β-D-glucopyranuronic acid, α-L-ribopyranose, α-L-arabinopyranose, α-L-xylopyranose, α-L-lyxopyranose, α-L-allopyranose, α-L-altropyranose, α-L-glucopyranose, α-L-mannopyranose, α-L-glucopyranose, α-L-idopyranose, α-L-galactopyranose, α-L-talopyranose, α-L-psicopyranose, α-L-fructopyranose, α-L-sorbopyranose, α-L-tagatopyranose, α-L-rhamnopyranose, α-L-ribofuranose, α-L-arabinofuranose, α-L-xylofuranose, α-L-lyxofuranose, α-L-allofuranose, α-L-altrofuranose, α-L-glucofuranose, α-L-mannofuranose, α-L-gulofuranose, α-L-idofuranose, α-L-galactofuranose, α-L-talofuranose, α-L-psicofuranose, α-L-fructofuranose, α-L-sorbofuranose, α-L-tagatofuranose, α-L-xylulofuranose, α-L-ribulofuranose, α-L-threofuranose, α-L-erythrofuranose, α-L-glucosamine, α-L-glucopyranuronic acid, β-L-ribopyranose, β-L-arabinopyranose, β-L-xylopyranose, β-L-lyxopyranose, β-L-allopyranose, β-L-altropyranose, β-L-glucopyranose, β-L-mannopyranose, β-L-glucopyranose, β-L-idopyranose, β-L-galactopyranose, β-L-talopyranose, β-L-psicopyranose, β-L-fructopyranose, β-L-sorbopyranose, β-L-tagatopyranose, β-L-ribofuranose, β-L-arabinofuranose, β-L-xylofuranose, β-L-lyxofuranose, β-L-allofuranose, β-L-altrofuranose, β-L-glucofuranose, β-L-mannofuranose, β-L-gulofuranose, β-L-idofuranose, β-L-galactofuranose, β-L-talofuranose, β-L-psicofuranose, β-L-fructofuranose, β-L-sorbofuranose, β-L-tagatofuranose, β-L-xylulofuranose, β-L-ribulofuranose, β-L-threofuranose, β-L-erythrofuranose, β-L-glucosamine, β-L-glucopyranuronic acid, β-L-rhamnopyranose,
or N- or O-substituted derivatives of neuraminic acid of the following formula:

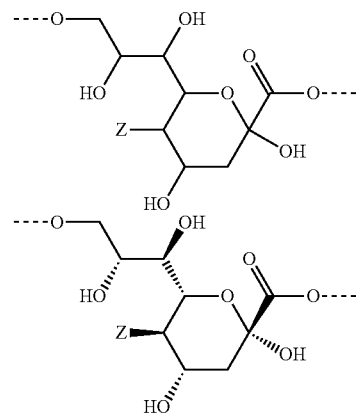

wherein Z represents —NH$_2$, —NHAc, or —OH.

3. A method of increasing immunogenicity of an individual against an infectious disease comprising administering an effective amount of the compound according to claim 1 to the individual.

4. Method according to claim 3, wherein the infectious disease is caused by a pathogen selected from the group consisting of:
Allochromatium vinosum, Acinetobacter baumanii, Bacillus anthracis, Campylobacter jejuni, Clostridium spp., Citrobacter spp., Escherichia coli, Enterobacter spp., Enterococcus faecalis., Enterococcus faecium, Francisella tularensis, Haemophilus influenzae, Helicobacter pylori, Klebsiella spp., Listeria monocytogenes, Moraxella catharralis, Mycobacterium tuberculosis, Neisseria meningitidis, Neisseria gonorrhoeae, Proteus mirabilis, Proteus vulgaris, Pseudomonas aeruginosa, Salmonella spp., Serratia spp., Shigella spp., Stenotrophomonas maltophilia, Staphyloccocus aureus, Staphyloccocus epidermidis, Streptococcus pneumoniae, Streptococcus pyogenes, Streptococcus agalactiae, Yersina pestis, Yersina enterocolitica, influenza virus, human immunodeficiency virus, herpes simplex virus type 1 or 2 human papilloma virus type 16 or 18, human cytomegalovirus and human hepatitis B or C virus.

5. Compound according to claim 1, wherein the bacterial capsular saccharide belongs to bacteria selected from the group consisting of:
Allochromatium vinosum, Acinetobacter baumanii, Bacillus anthracis, Campylobacter jejuni, Clostridium spp., Citrobacter spp., Escherichia coli, Enterobacter spp., Enterococcus faecalis., Enterococcus faecium, Francisella tularensis, Haemophilus influenzae, Helicobacter pylori, Klebsiella spp., Listeria monocytogenes, Moraxella catharralis, Mycobacterium tuberculosis, Neisseria meningitidis, Neisseria gonorrhoeae, Proteus mirabilis, Proteus vulgaris, Pseudomonas aeruginosa, Salmonella spp., Serratia spp., Shigella spp., Stenotrophomonas maltophilia, Staphyloccocus aureus, Staphyloccocus epidermidis, Streptococcus pneumonia, Streptococcus pyogenes, Streptococcus agalactiae, Yersina pestis, and Yersina enterocolitica.

6. Compound according to claim 1, wherein the saccharide of viral glycoproteins belongs to viruses selected from the group consisting of:

Adenoviruses, Ebolavirus, Epstein-Barr-virus, Flavivirus, FSME-virus, Influenza virus, Hanta-virus, human immunodeficiency virus, herpes simplex virus type 1 or 2, human herpes virus 6, human Papilloma virus ("HPV", type 16 or 18), human Cytomegalovirus, human hepatitis B or C virus, Lassavirus, Lassavirus 1 or 2 Marburgvirus, Norovirus, Parvovirus B19, Pestvirus, Poliovirus, Rhinovirus, Rotaviruses, SARS-associated Coronavirus, and Varicella-Zoster virus.

7. Compound according to claims 1, wherein the saccharide antigen of sporozoa or parasites belongs to sporozoa or parasites selected from the group consisting of: Babesia, Balantidium, Besnoitia, Blastocystis, Coccidia, Cryptosporidium, Cytauxzoon, Cyclospora, Dientamoeba, Eimeria, Entamoeba, Enterocytozoon, Enzephalitozoon, Eperythrozoon, Giardia, Hammondia, Isospora, Leishmania, Microsporidia, Naegleria, Plasmodium, Plasmodium falciparum, Plasmodium vivax, Plasmodium ovale, Plasmodium malariae, Plasmodium knowlesi, Pneumocystis, Schistosoma, Sarcocystis, Theileria, Trichinella, Toxoplasma, Trichomonas, Trypanosoma, Unicaria, Cestoda, Dipylidium, Dranunculus, Echinococcus, Fasciola, Fasciolopsis, Taenia, Ancylostoma, Ascaris, Brugia, Enterobius, Loa loa, Mansonella, Necator, Oncocerca, Strongyloides, Strongylus, Toxocara, Toxascaris, Trichuris and Wucheria.

8. Compound according to claim 1, wherein the saccharide antigen of fungi belongs to fungi selected from the group consisting of:

Trichophyton mentagrophytes, Trichophyton rubrum, Trichophyton interdigitale, T. schonleinii, T. verrucosum, T. violaceum, T. tonsurans, *Trichophyton* spp., M. canis, Candida albicans, C. guillermondii, C. krusei, C. parapsilosis, C. tropicalis, C. glabrata, *Candida* spp., *Microsporum* spp., Microsporum canis, Microsporum audonii, Microsporum gypseum, M. ferrugineum, Trichosporum beigelii, Trichosporum inkiin, Aspergillus niger, Alternaria, Acremonium, Fusarium, and Scopulariopsis.

9. Compound according to claim 1, wherein the saccharide antigen which is specific to cancer cells is selected from the group of cancers consisting of: Bladder Cancer, Breast Cancer, Colon and Rectal Cancer, Endometrial Cancer, Kidney (Renal Cell) Cancer, Leukemia, Lung Cancer Melanoma, Non-Hodgkin Lymphoma, Pancreatic Cancer, Prostate Cancer and Thyroid Cancer.

10. Compound according to claim 1, wherein the average ratio of the carbohydrate antigen A to the glycolipid

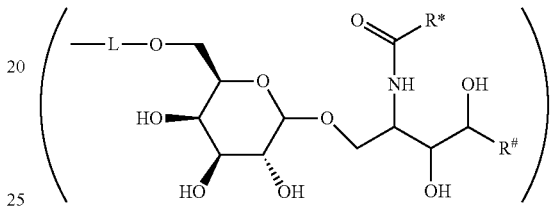

is between 1:4 and 1:100 (n/n).

11. Vaccine formulation comprising at least one compound of claim 1.

12. A method of increasing immunogenicity of an individual against an infectious disease comprising administering the vaccine formulation according to claim 11 to the individual.

* * * * *

SEQUENCE LISTING

<160> NUMBER OF SEQ ID NOS: 57

<210> SEQ ID NO 1
<211> LENGTH: 9
<212> TYPE: PRT

```
<213> ORGANISM: Mus musculus

<400> SEQUENCE: 1

Gly Tyr Ser Ile Thr Ser Gly Tyr Ser
1               5

<210> SEQ ID NO 2
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any amino acid

<400> SEQUENCE: 2

Gly Phe Ser Leu Thr Ser Xaa Tyr Gly
1               5

<210> SEQ ID NO 3
<211> LENGTH: 9
<212> TYPE: PRT
<213> ORGANISM: Mus musculus

<400> SEQUENCE: 3

Gly Tyr Ser Ile Thr Ser Gly Tyr Ser
1               5

<210> SEQ ID NO 4
<211> LENGTH: 9
<212> TYPE: PRT
<213> ORGANISM: Mus musculus

<400> SEQUENCE: 4

Gly Tyr Ser Ile Thr Ser Gly Tyr Ser
1               5

<210> SEQ ID NO 5
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any amino acid

<400> SEQUENCE: 5

Gly Phe Ser Leu Thr Ser Xaa Tyr Gly
1               5

<210> SEQ ID NO 6
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any

<400> SEQUENCE: 6

Gly Phe Ser Leu Thr Ser Xaa Tyr Gly
1               5

<210> SEQ ID NO 7
<211> LENGTH: 9
<212> TYPE: PRT
<213> ORGANISM: Mus musculus
```

```
<220> FEATURE:
<221> NAME/KEY: MOD_RES
<222> LOCATION: (1)..(9)
<223> OTHER INFORMATION: any amino acid

<400> SEQUENCE: 7

Gly Tyr Thr Phe Thr Ser Xaa Tyr Tyr
1               5

<210> SEQ ID NO 8
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any

<400> SEQUENCE: 8

Gly Tyr Ser Phe Thr Gly Xaa Tyr Asn
1               5

<210> SEQ ID NO 9
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any amino acid

<400> SEQUENCE: 9

Gly Phe Thr Phe Ser Ser Xaa Tyr Gly
1               5

<210> SEQ ID NO 10
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any amino acid

<400> SEQUENCE: 10

Gly Phe Ser Leu Thr Ser Xaa Tyr Gly
1               5

<210> SEQ ID NO 11
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any amino acid

<400> SEQUENCE: 11

Gly Phe Ser Leu Thr Ser Xaa Tyr Gly
1               5

<210> SEQ ID NO 12
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any amino acid
```

```
<400> SEQUENCE: 12

Gly Tyr Thr Phe Thr Xaa Asp Tyr Ala
1               5

<210> SEQ ID NO 13
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any amino acid

<400> SEQUENCE: 13

Gly Phe Ser Leu Thr Ser Xaa Tyr Gly
1               5

<210> SEQ ID NO 14
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any amino acid

<400> SEQUENCE: 14

Gly Tyr Thr Phe Thr Ser Xaa Tyr Trp
1               5

<210> SEQ ID NO 15
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any amino acid

<400> SEQUENCE: 15

Gly Phe Ser Leu Thr Asp Xaa Tyr Gly
1               5

<210> SEQ ID NO 16
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any amino acid

<400> SEQUENCE: 16

Gly Tyr Thr Phe Ser Arg Xaa Tyr Trp
1               5

<210> SEQ ID NO 17
<211> LENGTH: 9
<212> TYPE: PRT
<213> ORGANISM: Mus musculus
<220> FEATURE:
<221> NAME/KEY: misc_feature
<222> LOCATION: (7)..(7)
<223> OTHER INFORMATION: Xaa can be any naturally occurring amino acid

<400> SEQUENCE: 17

Gly Tyr Ser Phe Thr Gly Xaa Tyr Asn
```

```
<210> SEQ ID NO 18
<211> LENGTH: 9
<212> TYPE: PRT
<213> ORGANISM: Mus musculus
<220> FEATURE:
<221> NAME/KEY: MOD_RES
<222> LOCATION: (1)..(9)
<223> OTHER INFORMATION: any amino acid

<400> SEQUENCE: 18

Gly Tyr Ser Phe Thr Gly Xaa Tyr Asn
1               5

<210> SEQ ID NO 19
<211> LENGTH: 9
<212> TYPE: PRT
<213> ORGANISM: Mus musculus

<400> SEQUENCE: 19

Gly Tyr Ser Ile Thr Ser Asp Tyr Ala
1               5

<210> SEQ ID NO 20
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 20

Ile Xaa His Tyr Xaa Xaa Ser Gly Tyr Thr
1               5                   10

<210> SEQ ID NO 21
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 21

Ile Xaa Xaa Trp Xaa Ser Asp Gly Ser Thr
1               5                   10

<210> SEQ ID NO 22
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 22

Ile Xaa His Tyr Xaa Xaa Ser Gly Tyr Thr
1               5                   10

<210> SEQ ID NO 23
<211> LENGTH: 10
<212> TYPE: PRT
<213> ORGANISM: Mus musculus
<220> FEATURE:
```

<221> NAME/KEY: MOD_RES
<222> LOCATION: (1)..(10)
<223> OTHER INFORMATION: any amino acid

<400> SEQUENCE: 23

Ile Xaa His Tyr Xaa Xaa Ser Gly Ser Thr
1               5                   10

<210> SEQ ID NO 24
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 24

Ile Xaa Xaa Trp Xaa Ser Gly Gly Ser Thr
1               5                   10

<210> SEQ ID NO 25
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 25

Ile Xaa Xaa Trp Xaa Gly Asp Gly Ser Thr
1               5                   10

<210> SEQ ID NO 26
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 26

Ile Xaa Ile Tyr Pro Gly Asn Val Asn Thr
1               5                   10

<210> SEQ ID NO 27
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 27

Ile Asp Pro Tyr Xaa Xaa Tyr Gly Gly Thr
1               5                   10

<210> SEQ ID NO 28
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

```
<400> SEQUENCE: 28

Ile Xaa Ser Xaa Ser Gly Gly Ser Tyr Thr
1               5                   10

<210> SEQ ID NO 29
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 29

Ile Xaa Xaa Trp Xaa Ser Gly Gly Ser Thr
1               5                   10

<210> SEQ ID NO 30
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 30

Ile Xaa Xaa Trp Xaa Ser Gly Gly Ser Thr
1               5                   10

<210> SEQ ID NO 31
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 31

Ile Ser Thr Tyr Xaa Xaa Tyr Gly Asn Thr
1               5                   10

<210> SEQ ID NO 32
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 32

Ile Xaa Xaa Trp Xaa Ser Gly Gly Ser Thr
1               5                   10

<210> SEQ ID NO 33
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 33

Ile Xaa Xaa Asn Pro Ser Thr Gly Tyr Thr
1               5                   10
```

<210> SEQ ID NO 34
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 34

Ile Xaa Xaa Trp Xaa Gly Gly Gly Ser Thr
1               5                   10

<210> SEQ ID NO 35
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 35

Ile Xaa Xaa Leu Pro Gly Ser Gly Thr Thr
1               5                   10

<210> SEQ ID NO 36
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 36

Ile Asp Pro Tyr Xaa Xaa Tyr Gly Gly Thr
1               5                   10

<210> SEQ ID NO 37
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 37

Ile Asp Pro Tyr Xaa Xaa Tyr Gly Gly Thr
1               5                   10

<210> SEQ ID NO 38
<211> LENGTH: 10
<212> TYPE: PRT
<213> ORGANISM: Mus musculus
<220> FEATURE:
<221> NAME/KEY: MOD_RES
<222> LOCATION: (1)..(10)
<223> OTHER INFORMATION: any amino acid

<400> SEQUENCE: 38

Ile Xaa Ser Tyr Xaa Xaa Ser Gly Ser Thr
1               5                   10

<210> SEQ ID NO 39
<211> LENGTH: 20

```
<212> TYPE: PRT
<213> ORGANISM: Mus musculus
<220> FEATURE:
<221> NAME/KEY: MOD_RES
<222> LOCATION: (1)..(15)
<223> OTHER INFORMATION: any amino acid
<220> FEATURE:
<221> NAME/KEY: MOD_RES
<222> LOCATION: (1)..(20)
<223> OTHER INFORMATION: any amino acid

<400> SEQUENCE: 39

Ala Arg Ser Ala Asn Tyr Gly Pro Met Xaa Xaa Xaa Xaa Xaa Asp Tyr
1               5                   10                  15

Trp Gly Gln Gly
            20

<210> SEQ ID NO 40
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 40

Ala Arg His Ser Lys Leu Gly Gln Phe Xaa Xaa Xaa Xaa Xaa Ala Tyr
1               5                   10                  15

Trp Gly Gln Gly
            20

<210> SEQ ID NO 41
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 41

Ala Arg Ser Ala Asn Tyr Gly Pro Met Xaa Xaa Xaa Xaa Xaa Asp Tyr
1               5                   10                  15

Trp Gly Gln Gly
            20

<210> SEQ ID NO 42
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 42

Ala Arg Ser Ala Asn Tyr Gly Pro Met Xaa Xaa Xaa Xaa Xaa Asp Tyr
1               5                   10                  15

Trp Gly Gln Gly
            20

<210> SEQ ID NO 43
<211> LENGTH: 20
<212> TYPE: PRT
<213> ORGANISM: Mus musculus
<220> FEATURE:
```

-continued

```
<221> NAME/KEY: MOD_RES
<222> LOCATION: (1)..(20)
<223> OTHER INFORMATION: any amino acid

<400> SEQUENCE: 43

Val Arg Asn Gly Val Tyr Arg Asp Phe Xaa Xaa Xaa Xaa Xaa Ala Tyr
1               5                   10                  15

Trp Gly Gln Gly
            20

<210> SEQ ID NO 44
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 44

Ala Lys Ile Tyr Tyr Tyr Gly Arg Asn Xaa Xaa Tyr Ala Met Asp Tyr
1               5                   10                  15

Trp Gly Gln Gly
            20

<210> SEQ ID NO 45
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 45

Ala Arg Gly Gly Asn Tyr Tyr Tyr Xaa Xaa Xaa Ala Met Asp Tyr
1               5                   10                  15

Trp Gly Gln Gly
            20

<210> SEQ ID NO 46
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 46

Ala Arg Ser Thr Gly Thr Ala Trp Phe Xaa Xaa Xaa Xaa Xaa Ala Trp
1               5                   10                  15

Trp Gly Gln Gly
            20

<210> SEQ ID NO 47
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 47

Ala Arg Leu Tyr Asp Xaa Gly Tyr Tyr Xaa Val Ala Trp Phe Ala Tyr
```

-continued

```
1               5                   10                  15

Trp Gly Gln Gly
            20

<210> SEQ ID NO 48
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 48

Ala Arg Asn Ser Gly Thr Gly Trp Tyr Xaa Xaa Xaa Xaa Phe Asp Val
1               5                   10                  15

Trp Gly Ala Gly
            20

<210> SEQ ID NO 49
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 49

Ala Arg Asn Gly Asn Arg Ala Trp Phe Xaa Xaa Xaa Xaa Xaa Ala Tyr
1               5                   10                  15

Trp Gly Gln Gly
            20

<210> SEQ ID NO 50
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 50

Ala Arg Xaa Xaa Xaa Xaa Gly Asp Trp Xaa Xaa Xaa Xaa Glu Asp Tyr
1               5                   10                  15

Trp Gly Gln Gly
            20

<210> SEQ ID NO 51
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 51

Ala Arg Asp Gly Tyr Pro Ala Trp Phe Xaa Xaa Xaa Xaa Xaa Ala Tyr
1               5                   10                  15

Trp Gly Gln Gly
            20

<210> SEQ ID NO 52
```

-continued

```
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 52

Ala Arg Gly Arg Asn Xaa Xaa His Tyr Xaa Xaa Xaa Xaa Phe Asp Tyr
1               5                   10                  15

Trp Gly Gln Gly
            20

<210> SEQ ID NO 53
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 53

Ala Lys Gln Gly Asn Trp Ala Asp Tyr Xaa Xaa Tyr Ala Met Asp Tyr
1               5                   10                  15

Trp Gly Gln Gly
            20

<210> SEQ ID NO 54
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 54

Ala Arg Leu Leu Arg Xaa Xaa Xaa Tyr Xaa Xaa Xaa Xaa Phe Asp Tyr
1               5                   10                  15

Trp Gly Gln Gly
            20

<210> SEQ ID NO 55
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 55

Ala Arg Ser Xaa Asn Trp Thr Tyr Tyr Xaa Xaa Tyr Ala Met Asp Tyr
1               5                   10                  15

Trp Gly Gln Gly
            20

<210> SEQ ID NO 56
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid
```

```
<400> SEQUENCE: 56

Ala Arg Xaa Xaa Xaa Xaa Xaa Gly Tyr Xaa Xaa Xaa Ala Met Asp Tyr
1               5                   10                  15

Trp Gly Gln Gly
            20

<210> SEQ ID NO 57
<211> LENGTH: 20
<212> TYPE: PRT
<213> ORGANISM: Mus musculus
<220> FEATURE:
<221> NAME/KEY: MOD_RES
<222> LOCATION: (1)..(20)
<223> OTHER INFORMATION: any amino acid

<400> SEQUENCE: 57

Ala Arg Ser Leu Xaa Tyr Gly Asn Tyr Gly Asp Tyr Ala Met Asp Tyr
1               5                   10                  15

Trp Gly Gln Gly
            20
```